US012753230B2

(12) United States Patent
Wang et al.

(10) Patent No.: US 12,753,230 B2
(45) Date of Patent: Oct. 6, 2026

(54) ANTI-NECTIN-4 ANTIBODY, CONJUGATE INCLUDING THE SAME, AND APPLICATION THEREOF

(71) Applicant: SICHUAN KELUN-BIOTECH BIOPHARMACEUTICAL CO., LTD., Chengdu (CN)

(72) Inventors: Cheng Wang, Chengdu (CN); Dengnian Liu, Chengdu (CN); Fen Li, Chengdu (CN); Liang Xiao, Chengdu (CN); Tongtong Xue, Chengdu (CN); Junyou Ge, Chengdu (CN); Jingyi Wang, Chengdu (CN); Le Liu, Wuhan (CN); Qi Ren, Wuhan (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 597 days.

(21) Appl. No.: 18/026,576

(22) PCT Filed: Sep. 6, 2021

(86) PCT No.: PCT/CN2021/116651

§ 371 (c)(1),
(2) Date: Mar. 15, 2023

(87) PCT Pub. No.: WO2022/057651

PCT Pub. Date: Mar. 24, 2022

(65) Prior Publication Data

US 2024/0228612 A1 Jul. 11, 2024
US 2025/0026825 A2 Jan. 23, 2025
US 2025/0223352 A2 Jul. 10, 2025

(30) Foreign Application Priority Data

Sep. 16, 2020 (CN) ......................... 202010972365.6
Dec. 31, 2020 (CN) ......................... 202011624826.7

(51) Int. Cl.

| | |
|---|---|
| ***C07K 16/28*** | (2006.01) |
| ***A61K 38/17*** | (2006.01) |
| ***A61K 39/00*** | (2006.01) |
| ***A61K 47/68*** | (2017.01) |
| ***A61P 35/00*** | (2006.01) |
| ***C07K 14/705*** | (2006.01) |
| ***C07K 14/725*** | (2006.01) |
| ***C12N 5/0783*** | (2010.01) |
| ***G01N 33/575*** | (2026.01) |

(52) U.S. Cl.
CPC .......... *C07K 16/2803* (2013.01); *A61K 39/00* (2013.01); *A61K 47/68031* (2023.08); *A61K 47/68037* (2023.08); *A61K 47/6849* (2017.08); *A61K 47/6889* (2017.08); *A61P 35/00* (2018.01); *C07K 14/7051* (2013.01); *C07K 2317/24* (2013.01); *C07K 2317/31* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 2019/0076438 A1 | 3/2019 | Xue et al. |
| 2020/0199214 A1 | 6/2020 | Beckmann et al. |
| 2020/0347075 A1 | 11/2020 | Cai et al. |
| 2021/0324104 A1 | 10/2021 | Lopez |

FOREIGN PATENT DOCUMENTS

| | | | |
|---|---|---|---|
| CN | 106729743 A | 5/2017 |
| CN | 110392697 A | 10/2019 |
| CN | 110903395 A | 3/2020 |
| EP | 3347048 B1 | 4/2020 |
| JP | 2019-502650 | 1/2019 |
| JP | 2020-510432 | 4/2020 |
| JP | 2020-522261 | 7/2020 |
| KR | 20150063847 A | 6/2015 |
| WO | WO 2014/009465 A1 | 6/2014 |
| WO | WO 2015/107015 A1 | 7/2015 |
| WO | WO 2018/037000 A1 | 3/2018 |
| WO | WO 2018/226578 A1 | 12/2018 |
| WO | WO 2019/114666 A1 | 6/2019 |
| WO | WO 2019/154776 A1 | 8/2019 |
| WO | WO 2019215728 A1 | 11/2019 |
| WO | WO 2020/089051 A1 | 5/2020 |

OTHER PUBLICATIONS

Hanna et al., 2020, "Enfortumab vedotin to treat urothelial carcinoma," *Drugs Today* (*Barc*), 56(5):329-335.
International Search Report and Written Opinion mailed Dec. 1, 2021 for PCT Application No. PCT/CN2021/116651 filed Sep. 6, 2021.

*Primary Examiner* — Juliet C Switzer
*Assistant Examiner* — Katherine Ann Holtzman
(74) *Attorney, Agent, or Firm* — Jones Day

(57) ABSTRACT

Provided are an anti-Nectin-4 antibody or antigen-binding fragment thereof, an antibody conjugate comprising the same, and use thereof in the manufacture of a medicament, particularly in the manufacture of a medicament for treating and/or preventing cancer.

35 Claims, 13 Drawing Sheets

Specification includes a Sequence Listing.

ANTI-NECTIN-4 ANTIBODY, CONJUGATE INCLUDING THE SAME, AND APPLICATION THEREOF

The present application is a U.S. National Stage Application under 35 U.S.C. § 371 of International Patent Application No. PCT/CN2021/116651, filed Sep. 6, 2021, which claims the priority of Chinese Application No. 202010972365.6 filed on Sep. 16, 2020 and the priority of Chinese Application No. 202011624826.7 filed on Dec. 31, 2020, and the entire contents of these applications are incorporated herein by reference.

SEQUENCE LISTING

The application incorporates by reference in its entirety the Computer Readable Form (CRF) of a Sequence Listing in ASCII text format submitted via EFS-Web. The sequence Listing text file submitted via EFS-Web, entitled "14463-049-999_SUB_SL.txt", created on Aug. 9, 2023, and is 27,850 bytes in size.

TECHNICAL FIELD

The present invention belongs to the field of biomedicine. In particular, the present invention relates to an anti-Nectin-4 antibody and a conjugate comprising the same, as well as applications thereof, particularly in the treatment and/or prevention of a Nectin-4-related disease.

BACKGROUND ART

Nectin-4, belonging to the Nectin family protein also known as PVRL that belongs to the immunoglobulin superfamily, mainly functions in mediating calcium ion-independent cell adhesion junction. The Nectin family includes members of Nectin-1, Nectin-2, Nectin-3 and Nectin-4, has about 510-550 amino acids in size, and belongs to type I transmembrane protein, the structure of which comprises an extracellular segment formed by three Ig-like domains, a transmembrane region and an intracellular tail region. The three Ig-like domains comprise one IgV domain and two IgC domains, and the C-terminal of the intracellular domain has a conservative region composed of Glu/Ala-X-Tyr-Val, which is used to bind the PDZ domain of Afadin protein. Nectin-4 does not have this protein sequence, but it can still bind to Afadin protein intracellularly.

Nectin-4 can promote tumor cell survival and proliferation by inhibiting anoikis and activating PI3K-AKT signaling pathway. Studies have shown that Nectin-4 is expressed in gastric cancer, hepatocellular carcinoma, non-small cell lung cancer, bladder cancer, breast cancer, pancreatic cancer, ovarian cancer, head and neck cancer and esophageal cancer, and strongly expressed in non-small cell lung cancer, bladder cancer, breast cancer and pancreatic cancer. The high expression of Nectin-4 in tumors is closely related to the poor prognosis of patients. Therefore, Nectin-4 can be used as an ideal target for tumor drug development.

At present, the ADC drug Enfortumab Vedotin (see, for example, WO2012/047724) targeting Nectin-4 is already available for the treatment of urothelial carcinoma. Enfortumab Vedotin is an anti-Nectin-4 fully human antibody conjugated VC-MMAE drug with a DAR value of 4. The phase III clinical data showed that 4 patients achieved complete remission (CR), 41 patients achieved partial response (PR), and the objective response rate (ORR) was 41%; the median OS reached 13.6 months, and the median duration of response was 5.75 months, and the median progression-free survival (PFS) was 5.4 months. The ORR was 40% in the 89 patients in the checkpoint inhibitor treatment group, and the ORR was 44% in the 23 patients in the checkpoint inhibitor-naive group, and the ORR was 39% in the 33 patients in the liver metastasis group. Enfortumab Vedotin has excellent antitumor efficacy.

Nectin-4 was expressed in the placenta, and weakly to moderately expressed in some normal tissues, such as skin, esophagus, breast, and bladder. The main clinical toxic and side effects of Enfortumab Vedotin were fatigue (54%); ≥grade 3 side effects were anemia (8%), hyponatremia (7%), urinary tract infection (7%), hyperglycemia (6%); 4 patients had serious drug-related side effects, including respiratory failure, urinary tract obstruction, diabetic ketoacidosis, and multiple organ failure. This indicates that the toxic and side effects of Enfortumab Vedotin are too serious.

CONTENTS OF THE PRESENT INVENTION

In one general aspect, the present invention provides an antibody or antigen-binding fragment thereof that specifically binds Nectin-4, comprising:

(1a) the following three heavy chain CDRs defined according to the Chothia numbering system: CDR-H1 comprising the sequence as set forth in SEQ ID NO: 3 or a variant thereof, CDR-H2 comprising the sequence as set forth in SEQ ID NO: 4 or a variant thereof, CDR-H3 comprising the sequence as set forth in SEQ ID NO: 5 or a variant thereof, and/or the following three light chain CDRs defined according to the Chothia numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof, or (1b) the following three heavy chain CDRs defined according to the Abm numbering system: CDR-H1 comprising the sequence as set forth in SEQ ID NO: 9 or a variant thereof, CDR-H2 comprising the sequence as set forth in SEQ ID NO: 10 or a variant thereof, CDR-H3 comprising the sequence as set forth in SEQ ID NO: 5 or a variant thereof, and/or the following three light chain CDRs defined according to the Abm numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof, or (1c) the following three heavy chain CDRs defined according to the Kabat numbering system: CDR-H1 comprising the sequence as set forth in SEQ ID NO: 11 or a variant thereof, CDR-H2 comprising the sequence as set forth in SEQ ID NO: 12 or a variant thereof H, CDR-H3 comprising the sequence as set forth in SEQ ID NO: 5 or a variant thereof, and/or the following three light chain CDRs defined according to the Kabat numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof; or the following three heavy chain CDRs defined according to the Kabat numbering system: CDR-H1 comprising the sequence as set forth in SEQ ID NO: 11 or a variant thereof, CDR-H2 comprising the sequence as set forth in SEQ ID NO: 63 or a variant thereof, CDR-H3 comprising the sequence as set forth in SEQ ID NO: 5 or a variant thereof, and/or the following three light chain CDRs defined according to the Kabat numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof; or (1d) the following three heavy chain CDRs defined according to the IMGT numbering system: CDR-H1 comprising the sequence as set forth in SEQ ID NO: 13 or a variant thereof, CDR-H2 comprising the sequence as set forth in SEQ ID NO: 14 or a variant thereof, CDR-H3 comprising the sequence as set forth in SEQ ID NO: 15 or a variant thereof, and/or the following three light chain CDRs defined according to the IMGT numbering system: CDR-L1 comprising the sequence as set forth in SEQ ID NO: 16 or a variant thereof, CDR-L2 comprising the sequence as set forth in SEQ ID NO: 17 or a variant thereof, CDR-L3 comprising the sequence as set forth in SEQ ID NO: 8 or a variant thereof; or (2a) the following three heavy chain CDRs defined according to the Chothia numbering system: CDR-H1 comprising the sequence as set forth in SEQ ID NO: 21 or a variant thereof, CDR-H2 comprising the sequence as set forth in SEQ ID NO: 22 or a variant thereof, CDR-H3 comprising the sequence as set forth in SEQ ID NO: 23 or a variant thereof, and/or the following three light chain CDRs defined according to the Chothia numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or the following three heavy chain CDRs defined according to the Chothia numbering system: CDR-H1 comprising the sequence as set forth in SEQ ID NO: 18 or a variant thereof, CDR-H2 comprising the sequence as set forth in SEQ ID NO: 22 or a variant thereof, CDR-H3 comprising the sequence as set forth in SEQ ID NO: 23 or a variant thereof, and/or the following three light chain CDRs defined according to the Chothia numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (2b) the following three heavy chain CDRs defined according to the Abm numbering system: CDR-H1 comprising the sequence as set forth in SEQ ID NO: 27 or a variant thereof, CDR-H2 comprising the sequence as set forth in SEQ ID NO: 28 or a variant thereof, CDR-H3 comprising the sequence as set forth in SEQ ID NO: 23 or a variant thereof, and/or the following three light chain CDRs defined according to the Abm numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof; or the following three heavy chain CDRs defined according to the Abm numbering system: CDR-H1 comprising the sequence as set forth in SEQ ID NO: 36 or a variant thereof, CDR-H2 comprising the sequence as set forth in SEQ ID NO: 28 or a variant thereof, CDR-H3 comprising the sequence as set forth in SEQ ID NO: 23 or a variant thereof, and/or the following three light chain CDRs defined according to the Abm numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof; or (2c) the following three heavy chain CDRs defined according to the Kabat numbering system: CDR-H1 comprising the sequence as set forth in SEQ ID NO: 29 or a variant thereof, CDR-H2 comprising the sequence as set forth in SEQ ID NO: 30 or a variant thereof, CDR-H3 comprising the sequence as set forth in SEQ ID NO: 23 or a variant thereof, and/or the following three light chain CDRs defined according to the Kabat numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or the following three heavy chain CDRs are defined according to the Kabat numbering system: CDR-H1 comprising the sequence as set forth in SEQ ID NO: 44 or a variant thereof, CDR-H2 comprising the sequence as set forth in SEQ ID NO: 30 or a variant thereof, CDR-H3 comprising the sequence as set forth in SEQ ID NO: 23 or a variant thereof, and/or the following three light chain CDRs defined according to the Kabat numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof; or (2d) the following three heavy chain CDRs defined according to the IMGT numbering system: CDR-H1 comprising the sequence as set forth in SEQ ID NO: 31 or a variant thereof, CDR-H2 comprising the sequence as set forth in SEQ ID NO: 32 or a variant thereof, CDR-H3 comprising the sequence as set forth in SEQ ID NO: 33 or a variant thereof, and/or the following three light chain CDRs defined according to the IMGT numbering system: CDR-L1 comprising the sequence as set forth in SEQ ID NO: 34 or a variant thereof, CDR-L2 comprising the sequence as set forth in SEQ ID NO: 35 or a variant thereof, CDR-L3 comprising the sequence as set forth in SEQ ID NO: 26 or a variant thereof; or the following three heavy chain CDRs defined according to the IMGT numbering system: CDR-H1 comprising the sequence as set forth in SEQ ID NO: 54 or a variant thereof, CDR-H2 comprising the sequence as set forth in SEQ ID NO: 32 or a variant thereof, CDR-H3 comprising the sequence as set forth in SEQ ID NO: 33 or a variant thereof, and/or the following three light chain CDRs defined according to the IMGT numbering system: CDR-L1 comprising the sequence as set forth in SEQ ID NO: 34 or a variant thereof, CDR-L2 comprising the sequence as set forth in SEQ ID NO: 35 or a variant thereof, CDR-L3 comprising the sequence as set forth in SEQ ID NO: 26 or a variant thereof; or (3a) the following three heavy chain CDRs defined according to the Chothia numbering system: CDR-H1 comprising the sequence as set forth in SEQ ID NO: 39 or a variant thereof, CDR-H2 comprising the sequence as set forth in SEQ ID NO: 40 or a variant thereof, CDR-H3 comprising the sequence as set forth in SEQ ID NO: 41 or a variant thereof, and/or the following three light chain CDRs defined according to the Chothia numbering system: CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof, or (3b) the following three heavy chain CDRs defined according to the Abm numbering system: CDR-H1 comprising the sequence as set forth in SEQ ID NO: 45 or a variant thereof, CDR-H2 comprising the sequence as set forth in SEQ ID NO: 46 or a variant thereof, CDR-H3 comprising the sequence as set forth in SEQ ID NO: 41 or a variant thereof, and/or the following three light chain CDRs defined according to the Abm numbering system: CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof; or (3c) the following three heavy chain CDRs defined according to the Kabat numbering system: CDR-H1 comprising the sequence as set forth in SEQ ID NO: 47 or a variant thereof, CDR-H2 comprising the sequence as set forth in SEQ ID NO: 48 or a variant thereof, CDR-H3 comprising the sequence as set forth in SEQ ID NO: 41 or a variant thereof, and/or the following three light chain CDRs defined according to the Kabat numbering system: CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof, or the following three heavy chain CDRs defined according to the Kabat numbering system: CDR-H1 comprising the sequence as set forth in SEQ ID NO: 47 or a variant thereof, CDR-H2 comprising the sequence as set forth in SEQ ID NO: 64 or a variant thereof, CDR-H3 comprising the sequence as set forth in SEQ ID NO: 41 or a variant thereof, and/or the following three light chain CDRs defined according to the Kabat numbering system: CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof; or (3d) the following three heavy chain CDRs defined according to the IMGT numbering system: CDR-H1 comprising the sequence as set forth in SEQ ID NO: 49 or a variant thereof, CDR-H2 comprising the sequence as set forth in SEQ ID NO: 50 or a variant thereof, CDR-H3 comprising the sequence as set forth in SEQ ID NO: 51 or a variant thereof, and/or the following three light chain CDRs defined according to the IMGT numbering system: CDR-L1 comprising the sequence as set forth in SEQ ID NO: 52 or a variant thereof, CDR-L2 comprising the sequence as set forth in SEQ ID NO: 53 or a variant thereof, CDR-L3 comprising the sequence as set forth in SEQ ID NO: 8 or a variant thereof;

wherein the variant has a substitution, deletion or addition of one or more amino acids (e.g., a substitution, deletion or addition of 1, 2 or 3 amino acids) compared to the sequence from which it is derived; preferably, the substitution is a conservative substitution.

In preferred embodiments, the antibody or antigen-binding fragment thereof further comprises a framework region derived from a human or murine immunoglobulin.

In one aspect, the present invention provides an antibody conjugate, comprising the antibody or antigen-binding fragment thereof of the present invention and at least one therapeutic agent.

In yet another aspect, the present invention provides a chimeric antigen receptor (CAR) and an immune effector cell expressing the CAR.

In yet another aspect, the present invention also relates to a fusion protein, comprising the antibody or antigen-binding fragment thereof of the present invention, and an additional biologically active polypeptide.

The present invention also relates to a pharmaceutical composition, comprising the antibody or antigen-binding fragment thereof, antibody conjugate, immune effector cell, multispecific antibody or fusion protein of the present invention, and a pharmaceutically acceptable carrier and/or excipient.

In yet another general aspect, the present invention relates to use of the antibody or antigen-binding fragment thereof, antibody conjugate, immune effector cell, multispecific antibody, fusion protein or pharmaceutical composition of the present invention in the manufacture of a medicament for the treatment of a cancer.

The present invention also relates to use of the antibodies or antigen-binding fragment thereof, antibody conjugate, immune effector cell, multispecific antibody, fusion protein or pharmaceutical composition of the present invention in the treatment and/or prevention of a cancer.

In another general aspect, the present invention also provides a method of treating a cancer in a subject in need thereof, wherein the cancer is associated with Nectin-4. The method comprises administering to the subject a therapeutically effective amount of the antibody or antigen-binding fragment thereof, antibody conjugate, immune effector cell, multispecific antibody, fusion protein or pharmaceutical composition of the present invention.

Preferably, the cancer is selected from gastric cancer, liver cancer, hepatocellular carcinoma, bladder cancer, urothelial cancer, urethral cancer, renal pelvis cancer, ureteral cancer, lung cancer, non-small cell lung cancer, breast cancer, breast ductal cancer, triple-negative breast cancer, pancreatic cancer, ovarian cancer, head and neck cancer, colon cancer, rectal cancer and esophageal cancer.

SPECIFIC MODELS FOR CARRYING OUT THE PRESENT INVENTION

Definition

In the present invention, unless otherwise specified, scientific and technical terms used herein have the meanings commonly understood by those skilled in the art. Moreover, the protein and nucleic acid chemistry, molecular biology, cell and tissue culture, microbiology, immunology related terms and laboratory procedures used herein are the terms and routine procedures widely used in the corresponding fields. Meanwhile, for a better understanding of the present invention, definitions and explanations of related terms are provided below.

As used herein, "at least one (kind)" or "one (kind) or more (kind)" may refer to 1, 2, 3, 4, 5, 6, 7, 8, 9, 10, 11, 12, 13, 14, 15, 16, 17, 18, 19, 20 (kinds) or more (kinds).

The expression "comprising" or its equivalents "including", "containing" and "having" and the like are open-ended and do not exclude additional unrecited elements, steps or components. The expression "consisting of" excludes any element, step or component that is not specified. The expression "consisting essentially of" means that the scope is limited to the specified elements, steps or components, in addition of optional elements, steps or components that do not substantially affect the basic and novel characteristics of the claimed subject matter. It should be understood that the expression "comprising" encompasses the expressions "consisting essentially of" and "consisting of".

The term "optional" or "optionally" means that the subsequently described event or circumstance may or may not occur, and that the description includes both the occurrence of the event or circumstance and the non-occurrence of the event or circumstance.

As used herein, "polypeptide" refers to a polymer formed with two or more amino acids linked by peptide bonds. A "protein" may be formed covalently or non-covalently with one or more polypeptides. Unless otherwise indicated, the terms "polypeptide" and "protein" are used interchangeably herein.

As used herein, "antibody" refers to an immunoglobulin or fragment thereof that specifically binds an antigenic epitope through at least one antigen-binding site. Herein, the definition of antibody encompasses antigen-binding fragment. Thus, the term "antibody" comprises multispecific antibody (e.g., bispecific antibody), human antibody, non-human antibody, humanized antibody, chimeric antibody, single domain antibody, and antigen-binding fragment.

The antibody can be synthetic (e.g., produced by coupling chemically or biologically), enzymatically processed, or recombinantly produced. The antibody provided herein comprises any immunoglobulin type (e.g., IgG, IgM, IgD, IgE, IgA, and IgY), any class (e.g., IgG1, IgG2, IgG3, IgG4, IgA1, and IgA2), or subclass (e.g., IgG2a and IgG2b). In one embodiment, the antibody of the present invention is a murine monoclonal antibody. In yet another embodiment, the antibody of the present invention is a humanized monoclonal antibody.

As used herein, "traditional antibody" or "full-length antibody" typically comprises four polypeptides: two heavy chains (HC) and two light chains (LC). Each light chain comprises a "light chain variable region (VL)" and a "light chain constant region (CL)" from the N-terminal to the C-terminal. Each heavy chain comprises a "heavy chain variable region (VH)" and a "heavy chain constant region (CH)" from the N-terminal to the C-terminal. The heavy chain constant region may comprise CH1, CH2 and CH3 from the N-terminal to the C-terminal. In certain immunoglobulin types (e.g., IgM and IgE), the heavy chain constant region may further comprise CH4. "Fc" fragment refers to a fragment comprising CH2 and CH3, which provides the binding site for a Fc receptor. "Hinge region" refers to a portion of an antibody that connects the Fab and Fc fragment of immunoglobulin. In some instances, the hinge region refers to a portion of a T cell receptor that connects a constant region and a transmembrane domain. Herein, when used in reference to a chimeric antigen receptor, the hinge region may also refer to any functional equivalent. Those skilled in the art can judge the positions of VH, VL, CL, CH1, CH2, CH3 and hinge region in an antibody according to the known algorithms and software, and the description of applicable algorithms and software can be found in, for example, William R. Strohl, Lila M. Strohl, (2012), Antibody structure-function relationships, In Woodhead Publishing Series in Biomedicine, Therapeutic Antibody Engineering, Woodhead Publishing, pp. 37-56.

In general, VL and VH may each comprise three highly variable "complementarity determining regions (CDRs)" and four relatively conservative "framework regions (FRs)", which are connected in the sequence of FR1-CDR1-FR2-CDR2-FR3-CDR3-FR4 from the N-terminal to the C-terminal. Herein, the light chain variable region CDRs (CDRLs) may be referred to as CDR-L1, CDR-L2 and CDR-L3, and the heavy chain variable region CDRs (CDRHs) may be referred to as CDR-H1, CDR-H2 and CDR-H3. It is generally considered that six CDRs comprising a pair of VH and VL can determine the binding specificity of the antigen-binding site, but in some cases, other fragments (e.g., single-domain antibody, also known as nanobody) comprising fewer than six (e.g., three, four, or five) CDRs also have the antigen-binding ability. One skilled in the art can identify CDRs using methods well known in the art, for example using Kabat, Abm or Chothia numbering methods. In this context, multiple CDR numbering systems can be used for the same variable region, for example, Chothia, Abm, Kabat and IMGT. It will be understood by those skilled in the art that, although the CDRs defined by different numbering systems may be different, the CDRs identified in the same numbering system represent efficient antigen binding sites capable of binding antigen epitopes. The description of CDR numbering systems can be found in, for example, for Kabat numbering system: Kabat, E. A. et al. (1991) Sequences of Proteins of Immunological Interest, Fifth Edition, U.S. Department of Health and Human Services, NIH Publication No. 91-3242; for Chothia Numbering system: Chothia, C. et al. (1987) J. Mol. Biol. 196:901-917; or IMGT numbering system: Lefranc, M. P., 2011(6), IMGT, the International ImMunoGeneTics Information System Cold Spring Harb Protoc.; for Abm numbering system: Martin, A. C. R. and J. Allen (2007) "Bioinformatics tools for antibody engineering," in S. Dübel (ed.), Handbook of Therapeutic Antibodies. Weinheim: Wiley-VCH Verlag, pp. 95-118.

Herein, the terms "framework region" and "framework" are used interchangeably. As used herein, the term residues of "framework region", "framework" or "FR" refer to those amino acid residues in the variable region of an antibody other than the CDR residues as defined above.

It is generally considered that a "Fv" fragment consisting of one VH and one VL via non-covalent interaction is the smallest antigen-binding fragment that contains an antigen-binding site. However, the single-domain antibody (VHH, also known as sdAb or nanobody) that only contains the variable region of the heavy chain can also have antigen-binding ability. "Single-chain Fv (scFv)" can be obtained by linking VH and VL via a peptide linker. A "disulfide stabilized Fv (dsFv)" or "single-chain disulfide stabilized Fv (scdsFv or dsscFv)" can be obtained by introducing a disulfide bond into the Fv or scFv, respectively. In some embodiments, for example, the antibody conjugate, multi-specific antibody or antigen-binding fragment in CAR of the present invention preferably uses a scFv or scdsFv.

As used herein, "Fab" comprises one complete antibody light chain (VL-CL) and antibody heavy chain variable region and one heavy chain constant region (VH-CH1, also known as Fd). A single chain "Fab (scFab)" can be obtained by linking CL and CH1 in "Fab" with a peptide linker. "$F(ab')_2$" essentially comprises two Fab fragments linked by a disulfide bond in the hinge region. "Fab'" is half of $F(ab')_2$, which can be obtained by reducing the disulfide bond in the hinge region of $F(ab')_2$.

Antibody or antigen-binding fragment can be "monovalent", "bivalent", "trivalent" or "tetravalent" or more, meaning that they have a plurality of (e.g., 1, 2, 3, or 4 or more) antigen-binding sites.

When the antibody or antigen-binding fragment binds two or more (e.g., 2, 3, 4, 5, or 6) antigens, it may also be referred to as a "multispecific antibody", such as a bispecific antibody, trispecific or tetraspecific antibody, which represent a multispecific antibody capable of binding 2, 3 or 4 antigens, respectively.

As used herein, "diabody" refers to such an antibody that comprises two scFvs with two antigen-binding sites (bivalent), wherein the VH and VL in each scFv are linked by a short peptide linker (approximately 5-10 amino acid residues), such that the VH and VL chains are paired (i.e., the VH of the first scFv and the VL of the second scFv are paired, and the VL of the first scFv and the VH of the second scFv are paired) to form antigen-binding sites. The diabody can be a bispecific antibody.

As used herein, an "antigen-binding fragment" of antibody refers to a portion of a full-length antibody, it is shorter than full-length, but comprises at least a portion of the variable region of the full-length antibody (e.g., comprising one or more CDRs and/or one or more antigen-binding sites), and thus retain at least a portion of the ability of the full-length antibody to specifically bind an antigen. The antigen-binding fragment can include, for example, an antibody derivative produced by enzymatic treatment of full-length antibody, a synthetically produced derivative, or a recombinantly produced derivative. Examples of antigen-binding fragment include, but are not limited to, Fv, scFv, dsFv, scdsFv, Fab, scFab, Fab', $F(ab')_2$, diabody, Fd and Fd' fragments and other fragments (e.g., fragments comprising a modification). The antigen-binding fragment may comprise multiple peptide chains formed by, for example, linking via disulfide bonds and/or peptide linkers and/or non-covalent interaction.

As used herein, the term "monoclonal antibody" refers to a population of highly homogeneous antibodies, wherein the antibody molecules comprised therein are substantially identical except for possible naturally occurring mutations that may be present in minor amounts. Monoclonal antibody typically binds specifically to a single epitope. The monoclonal antibody useful in the present invention can be prepared by any method known in the art, such as production from a transgenic animal (e.g., transgenic mouse), production from an immortalized B cell (e.g., B cell hybridoma), or production from bacterial, eukaryotic or plant cells using recombinant DNA method, or isolation from phage antibody libraries. The antibody or antigen-binding fragment thereof of the present invention is a monoclonal antibody. In one embodiment, the antibody or antigen-binding fragment thereof of the present invention is a humanized monoclonal antibody.

"Chimeric antibody" refers to an antibody in which a portion (e.g., CDR, FR, variable region, constant region, or combination thereof) is identical or homologous to a corresponding sequence of an antibody derived from a particular species, and the remaining portion is identical or homologous to a corresponding sequence of an antibody derived from another species. As used herein, "chimeric antibody" also encompasses an antibody comprising portions belonging to different antibody classes or subclasses. In a specific embodiment, the chimeric antibody has a murine antibody variable region and a human antibody constant region.

As used herein, a "humanized antibody" refers to an antibody that comprises non-human antibody and human antibody sequences. Thus, the humanized antibody is a chimeric antibody that comprises a minimal sequence derived from a non-human immunoglobulin. The non-human antibody can be an antibody derived from any non-human species or an antibody comprising a portion derived from a non-human species (e.g., a chimeric antibody). The non-human species may include, for example, mouse, rat, rabbit, alpaca, or non-human primate. The techniques for obtaining humanized antibody from non-human antibody are well known to those skilled in the art. The humanized antibody can be produced from a non-human antibody (e.g., murine antibody or chimeric antibody), for example, by grafting a CDR sequence of the non-human antibody (e.g., murine antibody) into a human antibody framework region. In some cases, in order to maintain the antigen-binding ability and/or stability of the humanized antibody, the key amino acid residues of the framework sequence of the non-human antibody (e.g., murine antibody) can be retained in the framework region of the human antibody, that is, "back mutation" is performed (see, for example, Morrison et al. (1984) Proc. Natl. Acad. Sci. 81(21): 6851-6855; Neuberger et al. (1984) Nature 312: 604-608).

As used herein, "percent (%) sequence identity", "sequence identity" of amino acid sequence have the definition well-accepted in the art, and refer to a percent identity between two polypeptide sequences determined by sequence alignment (e.g., by manual inspection or well-known algorithm). It can be determined using methods known to those skilled in the art, for example, using publicly available computer software such as BLAST, BLAST-2, Clustal Omega, FASTA software.

"Affinity" or "binding affinity" is used to measure the strength of binding between an antibody and an antigen by non-covalent interaction. The magnitude of "affinity" can usually be reported as equilibrium dissociation constant $K_D$ or $EC_{50}$. $K_D$ can be calculated by measuring equilibrium association constant (ka) and equilibrium dissociation constant (kd): $K_D$=kd/ka.

Affinity can be determined using conventional techniques known in the art, such as biofilm interferometry (e.g., Octet Fortebio detection system can be used), radioimmunoassay, surface plasmon resonance, enzyme-linked immunoassay, or flow cytometry, and the like.

As used herein, "specific binding" between an antibody and an antigen refers to the binding between the antibody and the antigen with a high affinity. Typically, the $K_D$ value between the antibody and the antigen that are specifically bound is from at least about $10^{-6}$ to at least about 10-9 M or less, for example, at least about $10^{-6}$, at least about $10^{-7}$, at least about $10^{-8}$, at least about $10^{-9}$ M or less.

As used herein, an amino acid sequence "from" or "derived from" a reference amino acid sequence is partially or fully identical or homologous to the reference amino acid sequence. For example, the amino acid sequence of a heavy chain constant region derived from a human immunoglobulin has a sequence identity of at least 80%, at least 85%, at least 90%, at least 91%, at least 92%, at least 93%, at least 94%, at least 95%, at least 96%, at least 97%, at least 98%, at least 99% or 100%, as compared to the sequence of the heavy chain constant region of the wild-type human immunoglobulin from which it is derived.

As used herein, a "variant" of a polypeptide or amino acid sequence has a mutation or modification of one or more amino acids compared to the polypeptide or amino acid sequence from which it is derived. The amino acid mutation comprises substitution, deletion or addition of amino acids. Those skilled in the art will appreciate that an amino acid in a non-essential region of a polypeptide or protein can be substituted with an appropriate conservative amino acid which generally does not alter its biological activity (see, for example, Watson et al., Molecular Biology of the Gene, 4th Edition, 1987, The Benjamin/Cummings Pub. co., p. 224). Suitable conservative substitutions are well known to those skilled in the art. Non-limiting examples of some common conservative substitutions of amino acid residues are listed in the table below. In certain cases, the amino acid substitutions are non-conservative substitutions. It will be understood by those skilled in the art that an amino acid mutation or modification can be made to an antibody or antibody fragment to alter its properties, for example, to alter the type of antibody glycosylation modification, to alter the ability to form interchain disulfide bond, or to provide an active group to antibody conjugate. The antibody or antigen-binding fragment thereof comprising such amino acid mutation or modification is also encompassed within the scope of the antibody or antigen-binding fragment thereof of the present invention.

| Original residue | Exemplary conservative substitution | Preferred substitution |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe | Leu |
| Leu (L) | Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala | Leu |

As used herein, the terms "polynucleotide", "nucleic acid" and "nucleic acid molecule" refer to an oligomer or polymer comprising at least two linked nucleotides or nucleotide derivatives, which may generally comprise deoxyribonucleic acid (DNA) and ribonucleic acid (RNA).

As used herein, "isolated" means that a material (e.g., a nucleic acid molecule or polypeptide) is separated from the source or environment in which it exists, that is, it is substantially free of any other components.

As used herein, a "vector" is a vehicle used to introduce an exogenous nucleic acid into a host cell, when the vector is transformed into an appropriate host cell, the exogenous nucleic acid is amplified or expressed. The vector generally remains episomal, but can be designed to integrate a gene or portion thereof into the chromosome of genome. As used herein, the definition of vector encompasses plasmid, linearized plasmid, viral vector, cosmid, phage vector, phagemid, artificial chromosome (e.g., yeast artificial chromosome and mammalian artificial chromosome), and the like.

As used herein, an "expression vector" refers to a vector capable of expressing DNA, wherein the DNA is operably linked to a regulatory sequence (e.g., promoter, ribosome binding site) capable of affecting the DNA expression. The regulatory sequence may comprise promoter and terminator sequences, and optionally, may comprise replication origin, selectable marker, enhancer, polyadenylation signal, and the like. The expression vector may be a plasmid, phage vector, recombinant virus or other vector which, when introduced into an appropriate host cell, results in the expression of a cloned DNA. Appropriate expression vectors are well known to those skilled in the art and include the expression vectors that are replicable in eukaryotic and/or prokaryotic cells as well as the expression vectors that remain episomal or the expression vectors that integrate into the host cell genome.

As used herein, a "host cell" is a cell used to receive, maintain, replicate or amplify a vector. The host cell can also be used to express a polypeptide encoded by the nucleic acid or vector. The host cell can be an eukaryotic cell or prokaryotic cell.

As used herein, the term "treatment" refers to amelioration of a disease/symptom, for example, to reduce or eliminate the disease/symptom, to prevent or delay the occurrence, progression and/or worsening of the disease/symptom. Thus, the treatment comprises prevention, treatment and/or cure.

An "effective amount" refers to a dose sufficient to reduce the severity of a symptom of disease, increase the frequency and duration of asymptomatic period of disease, or prevent damage or disability due to the suffering of disease. The "effective amount" refers to an amount required to prevent, cure, ameliorate, retard or partially retard a disease or symptom. For example, for the treatment of tumor, an "effective amount" of the antibody or antigen-binding fragment thereof, antibody conjugate, immune effector cell, or pharmaceutical composition of the present invention preferably inhibits tumor cell growth or tumor growth by at least about 10%, preferably at least about 20%, more preferably at least about 30%, more preferably at least about 40%, more preferably at least about 50%, more preferably at least about 60%, more preferably at least about 70%, more preferably at least about 80%, relative to untreated subjects. The efficacy of inhibiting tumor growth can be assessed using conventional animal models of tumors in the art, such as animal models for spontaneous tumor, induced tumor, and transplanted tumor. Alternatively, the ability of inhibiting cell growth can also be examined using in vitro assays well known in the art. The effective amount of the antibody or antigen-binding fragment thereof, antibody conjugate, immune effector cell, or pharmaceutical composition of the present invention is capable of reducing tumor size, or otherwise alleviating symptoms in a subject (e.g., preventing and/or treating metastasis or relapse). Those skilled in the art can determine the effective amount based on factors such as the subject's age, physical condition, gender, severity of symptoms, particular composition or administration route, and the like. The effective amount can be administered in one or more administrations.

As used herein, the term "pharmaceutically acceptable carrier and/or excipient" refers to a carrier and/or excipient that is pharmacologically and/or physiologically compatible with the subject and the active ingredient, and it is well known in the art (see, for example, Remington's Pharmaceutical Sciences. Edited by Gennaro AR, 19th ed. Pennsylvania: Mack Publishing Company, 1995) and includes, but is not limited to: pH adjusting agents, surfactants, adjuvants, ionic strength enhancing agents, diluents, agents to maintain osmotic pressure, agents to delay absorption, preservatives. For example, the pH adjusting agents include, but are not limited to, phosphate buffer. The surfactants include, but are not limited to, cationic, anionic, or nonionic surfactant, such as Tween-80. The ionic strength enhancing agents include, but are not limited to, sodium chloride. The preservatives include, but are not limited to, various antibacterial and antifungal agents, such as paraben, chlorobutanol, phenol, sorbic acid, and the like. The agents to maintain osmotic pressure include, but are not limited to, sugar, NaCl, and the like. The agents to delay absorption include, but are not limited to, monostearate salt and gelatin. The diluents include, but are not limited to, water, aqueous buffer (e.g., buffered saline), alcohol and polyol (e.g., glycerol), and the like. The preservatives include, but are not limited to, various antibacterial and antifungal agents such as thimerosal, 2-phenoxyethanol, paraben, chlorobutanol, phenol, sorbic acid, and the like. The stabilizing agents have the meaning commonly understood by those skilled in the art, which can stabilize a desired activity of an active ingredient in a drug, including but not limited to, sodium glutamate, gelatin, SPGA, sugars (e.g., sorbitol, mannitol, starch, sucrose, lactose, glucan, or glucose), amino acids (e.g., glutamic acid, glycine), proteins (e.g., dry whey, albumin or casein) or degradation products thereof (e.g., lactalbumin hydrolyzate) and the like.

As used herein, examples of mammals include, but are not limited to, human, non-human primates, rat, mouse, cow, horse, pig, sheep, dog, cat, and the like. As used herein, the term "object" refers to a mammal, such as a human. In some embodiments, the subject is a human. In some embodiments, the subject is a cancer patient, a human or animal suspected of having a cancer or at risk of developing a cancer. Herein, the terms "object" and "subject" are used interchangeably.

Anti-Nectin-4 Antibodies or Antigen-Binding Fragments Thereof

In one general aspect, the present invention provides an anti-Nectin-4 antibody or antigen-binding fragment thereof that specifically recognizes and binds to Nectin-4.

Nectin-4 can be a protein comprising the full or partial amino acid sequence of human Nectin-4 or non-human Nectin-4. Preferably, the Nectin-4 is human Nectin-4. The human Nectin-4 can have the amino acid sequence, for example, as shown by Uniprot identification number (ID): Q96NY8-1. The non-human Nectin-4, for example, can be mammalian Nectin-4, such as non-human primate cynomolgus monkey Nectin-4, which may have the amino acid sequence, for example, as shown by Uniprot identification number (ID): L0N6D9. The non-human Nectin-4, for example, may also be rat Nectin-4, which may have the amino acid sequence, for example, as shown by Uniprot identification number (ID): D3ZET1. The non-human Nectin-4, for example, may also be mouse Nectin-4, which may have the amino acid sequence, for example, as shown by Uniprot identification number (ID): Q8R007.

In some embodiments, the antibody or antigen-binding fragment thereof is capable of specifically binding to an IgV domain of Nectin-4. In some embodiments, the antibody or antigen-binding fragment thereof is capable of specifically binding to an IgV domain of human Nectin-4.

In some embodiments, the antibody or antigen-binding fragment thereof is capable of specifically binding to Nectin-4 and blocking its interaction with Nectin-1.

In some embodiments, the anti-Nectin-4 antibody comprises a heavy chain variable region (VH) comprising 3 heavy chain CDRs (CDRH): CDR-H1, CDR-H2 and CDR-H3. The CDR-H1, CDR-H2 and CDR-H3 are selected from the CDRH group in Table 1.

TABLE 1

Heavy chain CDRs of anti-Nectin-4 antibody

| Numbering system | Group | CDR-H1 (SEQ ID NO:) | CDR-H2 (SEQ ID NO:) | CDR-H3 (SEQ ID NO:) |
|---|---|---|---|---|
| Chothia | a/e | GYTFTDY (3) | HPSDSE (4) | WDFRIYYAMDY (5) |
| | b | GYSITSDY (21) | SFSGR (22) | GNYDGFDY (23) |
| | c | GYFNSITSDY (18) | SFSGR (22) | GNYDGFDY (23) |
| | d/f | GYTFINY (39) | HPSDSA (40) | WGNFYTVNAWYY FDY (41) |
| Abm | a/e | GYTFTDYWMN (9) | MIHPSDSETR (10) | WDFRIYYAMDY (5) |
| | b | GYSITSDYDWH (27) | YISFSGRTY (28) | GNYDGFDY (23) |
| | c | GYFNSITSDYDWH (36) | YISFSGRTY (28) | GNYDGFDY (23) |
| | d/f | GYTFINYWMN (45) | MIHPSDSATR (46) | WGNFYTVNAWYY FDY (41) |
| Kabat | a | DYWMN (11) | MIHPSDSETRLNQKFKD (12) | WDFRIYYAMDY (5) |
| | b | SDYDWH (29) | YISFSGRTYYNPSLKS (30) | GNYDGFDY (23) |
| | c | ITSDYDWH (44) | YISFSGRTYYNPSLKS (30) | GNYDGFDY (23) |
| | d | NYWMN (47) | MIHPSDSATRLNQKFKD (48) | WGNFYTVNAWYY FDY (41) |

TABLE 1-continued

Heavy chain CDRs of anti-Nectin-4 antibody

| Numbering system | Group | CDR-H1 (SEQ ID NO:) | CDR-H2 (SEQ ID NO:) | CDR-H3 (SEQ ID NO:) |
|---|---|---|---|---|
| | e | DYWMN (11) | MIHPSDSETRLNQKFQG (63) | WDFRIYYAMDY (5) |
| | f | NYWMN (47) | MIHPSDSATRLNQSFQG (64) | WGNFYTVNAWYY FDY (41) |
| IMGT | a/e | GYTFTDYW (13) | IHPSDSET (14) | ARWDFRIYYAMD Y (15) |
| | b | GYSITSDYD (31) | ISFSGRT (32) | ARGNYDGFDY (33) |
| | c | GYFNSITSDYD (54) | ISFSGRT (32) | ARGNYDGFDY (33) |
| | d/f | GYTFINYW (49) | IHPSDSAT (50) | ARWGNFYTVNAW YYFDY (51) |

In some embodiments, the anti-Nectin-4 antibody comprises a light chain variable region (VL) comprising 3 light chain CDRs (CDRL): CDR-L1, CDR-L2 and CDR-L3. The CDR-L1, CDR-L2 and CDR-L3 are selected from the CDRL group in Table 2.

TABLE 2

Light chain CDRs of anti-Nectin-4 antibody

| Numbering system | group | CDR-L1 (SEQ ID NO:) | CDR-L2 (SEQ ID NO:) | CDR-L3 (SEQ ID NO:) |
|---|---|---|---|---|
| Chothia | a/e | KSSQSLLNTNSQKNYLA (6) | FASTRES (7) | QQHYSTPLT (8) |
| | b/c | RASQNIGTSIH (24) | FASESIS (25) | QQSKSWPTYT (26) |
| | d/f | KSSQTLLNSNTQKNYLA (42) | FASTRES (43) | QQHYSTPLT (8) |
| Abm | a/e | KSSQSLLNTNSQKNYLA (6) | FASTRES (7) | QQHYSTPLT (8) |
| | b/c | RASQNIGTSIH (24) | FASESIS (25) | QQSKSWPTYT (26) |
| | d/f | KSSQTLLNSNTQKNYLA (42) | FASTRES (43) | QQHYSTPLT (8) |
| Kabat | a/e | KSSQSLLNTNSQKNYLA (6) | FASTRES (7) | QQHYSTPLT (8) |
| | b/c | RASQNIGTSIH (24) | FASESIS (25) | QQSKSWPTYT (26) |
| | d/f | KSSQTLLNSNTQKNYLA (42) | FASTRES (43) | QQHYSTPLT (8) |
| IMGT | a/e | QSLLNTNSQKNY (16) | FAS (17) | QQHYSTPLT (8) |
| | b/c | QNIGTS (34) | FAS (35) | QQSKSWPTYT (26) |
| | d/f | QTLLNSNTQKNY (52) | FAS (53) | QQHYSTPLT (8) |

Complementarily Determining Regions (CDRs)

In some specific embodiments, the antibody or antigen-binding fragment thereof that specifically binds to Nectin-4 comprises the following three heavy chain CDRs defined according to the Chothia numbering system: CDR-H1 comprising the sequence as set forth in SEQ TD NO: 3 or a variant thereof, CDR-H2 comprising the sequence as set forth in SEQ ID NO: 4 or a variant thereof, CDR-H3 comprising the sequence as set forth in SEQ ID NO: 5 or a variant thereof. In other specific embodiments, the antibody or antigen-binding fragment thereof that specifically binds to Nectin-4 comprises the following three light chain CDRs defined according to the Chothia numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ TD NO: 8 or a variant thereof.

In some specific embodiments, the antibody or antigen-binding fragment thereof that specifically binds to Nectin-4 comprises the following three heavy chain CDRs defined according to the Abm numbering system: CDR-H1 comprising the sequence as set forth in SEQ ID NO: 9 or a variant thereof, CDR-H2 comprising the sequence as set forth in SEQ ID NO: 10 or a variant thereof, CDR-H3 comprising the sequence as set forth in SEQ ID NO: 5 or a variant thereof. In other specific embodiments, the antibody or antigen-binding fragment thereof that specifically binds to Nectin-4 comprises the following three light chain CDRs defined according to the Abm numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof.

In some specific embodiments, the antibody or antigen-binding fragment thereof that specifically binds to Nectin-4 comprises the following three heavy chain CDRs defined according to the Kabat numbering system: CDR-H1 comprising the sequence as set forth in SEQ ID NO: 11 or a variant thereof, CDR-H2 comprising the sequence as set forth in SEQ ID NO: 12 or 63 or a variant thereof, CDR-H3 comprising the sequence as set forth in SEQ ID NO: 5 or a variant thereof. In other specific embodiments, the antibody or antigen-binding fragment thereof that specifically binds to Nectin-4 comprises the following three light chain CDRs defined according to the Kabat numbering system: CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof.

In some specific embodiments, the antibody or antigen-binding fragment thereof that specifically binds to Nectin-4 comprises the following three heavy chain CDRs defined according to the IMGT numbering system: CDR-H1 comprising the sequence as set forth in SEQ ID NO: 13 or a variant thereof, CDR-H2 comprising the sequence as set forth in SEQ ID NO: 14 or a variant thereof, CDR-H3 comprising the sequence as set forth in SEQ ID NO: 15 or a variant thereof. In other specific embodiments, the antibody or antigen-binding fragment thereof that specifically binds to Nectin-4 comprises the following three light chain CDRs defined according to the IMGT numbering system: CDR-L1 comprising the sequence as set forth in SEQ ID NO: 16 or a variant thereof, CDR-L2 comprising the sequence as set forth in SEQ ID NO: 17 or a variant thereof, and CDR-L3 comprising the sequence as set forth in SEQ ID NO: 8 or a variant thereof.

In a specific embodiment, the antibody or antigen-binding fragment thereof that specifically binds to Nectin-4 comprises:

(a) CDRs of the following six heavy and light chains defined according to the Chothia numbering system: CDR-H1 comprising the sequence as set forth in SEQ ID NO: 3 or a variant thereof, CDR-H2 comprising the sequence as set forth in SEQ ID NO: 4 or a variant thereof, CDR-H3 comprising the sequence as set forth in SEQ ID NO: 5 or a variant thereof, CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof; or (b) CDRs of the following six heavy and light chains defined according to the Abm numbering system: CDR-H1 comprising the sequence as set forth in SEQ ID NO: 9 or a variant thereof, CDR-H2 comprising the sequence as set forth in SEQ ID NO: 10 or a variant thereof, CDR-H3 comprising the sequence as set forth in SEQ ID NO: 5 or a variant thereof, CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof, or (c) CDRs of the following six heavy and light chains defined according to the Kabat numbering system: CDR-H1 comprising the sequence as set forth in SEQ ID NO: 11 or a variant thereof, CDR-H2 comprising the sequence as set forth in SEQ ID NO: 12 or 63 or a variant thereof, CDR-H3 comprising the sequence as set forth in SEQ ID NO: 5 or a variant thereof, CDR-L1 comprising the sequence as set forth in SEQ ID NO: 6 or a variant thereof, CDR-L2 comprising the sequence as set forth in SEQ ID NO: 7 or a variant thereof, CDR-L3 comprising the sequence as set forth in SEQ ID NO: 8 or a variant thereof, or (d) CDRs of the following six heavy and light chains defined according to the IMGT numbering system: CDR-H1 comprising the sequence as set forth in SEQ ID NO: 13 or a variant thereof, CDR-H2 comprising the sequence as set forth in SEQ ID NO: 14 or a variant thereof, CDR-H3 comprising the sequence as set forth in SEQ ID NO: 15 or a variant thereof, CDR-L1 comprising the sequence as set forth in SEQ ID NO: 16 or a variant thereof, CDR-L2 comprising the sequence as set forth in SEQ ID NO: 17 or a variant thereof, CDR-L3 comprising the sequence as set forth in SEQ ID NO: 8 or a variant thereof.

In some specific embodiments, the antibody or antigen-binding fragment thereof that specifically binds to Nectin-4 comprises the following three heavy chain CDRs defined according to the Chothia numbering system: CDR-H1 comprising the sequence as set forth in SEQ ID NO: 21 or a variant thereof, CDR-H2 comprising the sequence as set forth in SEQ ID NO: 22 or a variant thereof, CDR-H3 comprising the sequence as set forth in SEQ ID NO: 23 or a variant thereof. In other specific embodiments, the antibody or antigen-binding fragment thereof that specifically binds to Nectin-4 comprises the following three light chain CDRs defined according to the Chothia numbering system: CDR-L1 comprising the sequence as set forth in SEQ ID NO: 24 or a variant thereof, CDR-L2 comprising the sequence as set forth in SEQ ID NO: 25 or a variant thereof, and CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the Abm numbering system: CDR-H1 comprising the sequence as set forth in SEQ ID NO: 27 or a variant thereof, CDR-H2 comprising the sequence as set forth in SEQ ID NO: 28 or a variant thereof, CDR-H3 comprising the sequence as set forth in SEQ ID NO: 23 or a variant thereof. In other specific embodiments, the antibody or antigen-binding fragment thereof that specifically binds to Nectin-4 comprises the following three light chain CDRs defined according to the Abm numbering system: CDR-L1 comprising the sequence as set forth in SEQ ID NO: 24 or a variant thereof, CDR-L2 comprising the sequence as set forth in SEQ ID NO: 25 or a variant thereof, and CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the Kabat numbering system: CDR-H1 comprising the sequence as set forth in SEQ ID NO: 29 or a variant thereof, CDR-H2 comprising the sequence as set forth in SEQ ID NO: 30 or a variant thereof, CDR-H3 comprising the sequence as set forth in SEQ ID NO: 23 or a variant thereof. In other specific embodiments, the antibody or antigen-binding fragment thereof that specifically binds to Nectin-4 comprises the following three light chain CDRs defined according to the Kabat numbering system: CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the IMGT numbering system: CDR-H1 comprising the sequence as set forth in SEQ ID NO: 31 or a variant thereof, CDR-H2 comprising the sequence as set forth in SEQ ID NO: 32 or a variant thereof, CDR-H3 comprising the sequence as set forth in SEQ ID NO: 33 or a variant thereof. In other specific embodiments, the antibody or antigen-binding fragment thereof that specifically binds to Nectin-4 comprises the following three light chain CDRs defined according to the IMGT numbering system: CDR-L1 comprising the sequence as set forth in SEQ ID NO: 34 or a variant thereof, CDR-L2 comprising the sequence as set forth in SEQ ID NO: 35 or a variant thereof, CDR-L3 comprising the sequence as set forth in SEQ ID NO: 26 or a variant thereof.

In a specific embodiment, the antibody or antigen-binding fragment thereof that specifically binds to Nectin-4 comprises:

(a) CDRs of the following six heavy and light chains defined according to the Chothia numbering system: CDR-H1 comprising the sequence as set forth in SEQ ID NO: 21 or a variant thereof, CDR-H2 comprising the sequence as set forth in SEQ ID NO: 22 or a variant thereof, CDR-H3 comprising the sequence as set forth in SEQ ID NO: 23 or a variant thereof, CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (b) CDRs of the following six heavy and light chains defined according to the Abm numbering system: CDR-H1 comprising the sequence as set forth in SEQ ID NO: 27 or a variant thereof, CDR-H2 comprising the sequence as set forth in SEQ ID NO: 28 or a variant thereof, CDR-H3 comprising the sequence as set forth in SEQ ID NO: 23 or a variant thereof, CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (c) CDRs of the following six heavy and light chains defined according to the Kabat numbering system: CDR-H1 comprising the sequence as set forth in SEQ ID NO: 29 or a variant thereof, CDR-H2 comprising the sequence as set forth in SEQ ID NO: 30 or a variant thereof, CDR-H3 comprising the sequence as set forth in SEQ ID NO: 23 or a variant thereof, CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (d) CDRs of the following six heavy and light chains defined according to the IMGT numbering system: CDR-H1 comprising the sequence as set forth in SEQ ID NO: 31 or a variant thereof, CDR-H2 comprising the sequence as set forth in SEQ ID NO: 32 or a variant thereof, CDR-H3 comprising the sequence as set forth in SEQ ID NO: 33 or a variant thereof, CDR-L1 comprising the sequence as set forth in SEQ ID NO: 34 or a variant thereof, CDR-L2 comprising the sequence as set forth in SEQ ID NO: 35 or a variant thereof, CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the Chothia numbering system: CDR-H1 comprising the sequence as set forth in SEQ ID NO: 18 or a variant thereof, CDR-H2 comprising the sequence as set forth in SEQ ID NO: 22 or a variant thereof, CDR-H3 comprising the sequence as set forth in SEQ ID NO: 23 or a variant thereof. In other specific embodiments, the antibody or antigen-binding fragment thereof that specifically binds to Nectin-4 comprises the following three light chain CDRs defined according to the Chothia numbering system: CDR-L1 comprising the sequence as set forth in SEQ ID NO: 24 or a variant thereof, CDR-L2 comprising the sequence as set forth in SEQ ID NO: 25 or a variant thereof, and CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the Abm numbering system: CDR-H1 comprising the sequence as set forth in SEQ ID NO: 36 or a variant thereof, CDR-H2 comprising the sequence as set forth in SEQ ID NO: 28 or a variant thereof, CDR-H3 comprising the sequence as set forth in SEQ ID NO: 23 or a variant thereof. In other specific embodiments, the antibody or antigen-binding fragment thereof that specifically binds to Nectin-4 comprises the following three light chain CDRs defined according to the Abm numbering system: CDR-L1 comprising the sequence as set forth in SEQ ID NO: 24 or a variant thereof, CDR-L2 comprising the sequence as set forth in SEQ ID NO: 25 or a variant thereof, and CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the Kabat numbering system: CDR-H1 comprising the sequence as set forth in SEQ ID NO: 44 or a variant thereof, CDR-H2 comprising the sequence as set forth in SEQ ID NO: 30 or a variant thereof, CDR-H3 comprising the sequence as set forth in SEQ ID NO: 23 or a variant thereof. In other specific embodiments, the antibody or antigen-binding fragment thereof that specifically binds to Nectin-4 comprises the following three light chain CDRs defined according to the Kabat numbering system: CDR-L1 comprising the sequence as set forth in SEQ ID NO: 24 or a variant thereof, CDR-L2 comprising the sequence as set forth in SEQ ID NO: 25 or a variant thereof, and CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the IMGT numbering system: CDR-H1 comprising the sequence as set forth in SEQ ID NO: 54 or a variant thereof, CDR-H2 comprising the sequence as set forth in SEQ ID NO: 32 or a variant thereof, CDR-H3 comprising the sequence as set forth in SEQ ID NO: 33 or a variant thereof. In other specific embodiments, the antibody or antigen-binding fragment thereof that specifically binds to Nectin-4 further comprises the following three light chain CDRs defined according to the IMGT numbering system: CDR-L1 comprising the sequence as set forth in SEQ ID NO: 34 or a variant thereof, CDR-L2 comprising the sequence as set forth in SEQ ID NO: 35 or a variant thereof, and CDR-L3 comprising the sequence as set forth in SEQ ID NO: 26 or a variant thereof.

In a specific embodiment, the antibody or antigen-binding fragment thereof that specifically binds to Nectin-4 comprises:

(a) CDRs of the following six heavy and light chains defined according to the Chothia numbering system: CDR-H1 comprising the sequence as set forth in SEQ ID NO: 18 or a variant thereof, CDR-H2 comprising the sequence as set forth in SEQ ID NO: 22 or a variant thereof, CDR-H3 comprising the sequence as set forth in SEQ ID NO: 23 or a variant thereof, CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (b) CDRs of the following six heavy and light chains defined according to the Abm numbering system: CDR-H1 comprising the sequence as set forth in SEQ ID NO: 36 or a variant thereof, CDR-H2 comprising the sequence as set forth in SEQ ID NO: 28 or a variant thereof, CDR-H3 comprising the sequence as set forth in SEQ ID NO: 23 or a variant thereof, CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (c) CDRs of the following six heavy and light chains defined according to the Kabat numbering system: CDR-H1 comprising the sequence as set forth in SEQ ID NO: 44 or a variant thereof, CDR-H2 comprising the sequence as set forth in SEQ ID NO: 30 or a variant thereof, CDR-H3 comprising the sequence as set forth in SEQ ID NO: 23 or a variant thereof, CDR-L1 comprising the sequence as set forth in SEQ ID NO: 24 or a variant thereof, CDR-L2 comprising the sequence as set forth in SEQ ID NO: 25 or a variant thereof, CDR-L3 comprising the sequence as set forth in SEQ ID NO: 26 or a variant thereof, or (d) CDRs of the following six heavy and light chains defined according to the IMGT numbering system: CDR-H1 comprising the sequence as set forth in SEQ ID NO: 54 or a variant thereof, CDR-H2 comprising the sequence as set forth in SEQ ID NO: 32 or a variant thereof, CDR-H3 comprising the sequence as set forth in SEQ ID NO: 33 or a variant thereof, CDR-L1 comprising the sequence as set forth in SEQ ID NO: 34 or a variant thereof, CDR-L2 comprising the sequence as set forth in SEQ ID NO: 35 or a variant thereof, CDR-L3 comprising the sequence as set forth in SEQ ID NO: 26 or a variant thereof.

In some specific embodiments, the antibody or antigen-binding fragment thereof that specifically binds to Nectin-4 comprises the following three heavy chain CDRs defined according to the Chothia numbering system: CDR-H1 comprising the sequence as set forth in SEQ ID NO: 39 or a variant thereof, CDR-H2 comprising the sequence as set forth in SEQ ID NO: 40 or a variant thereof, CDR-H3 comprising the sequence as set forth in SEQ ID NO: 41 or a variant thereof. In other specific embodiments, the antibody or antigen-binding fragment thereof that specifically binds to Nectin-4 comprises the following three light chain CDRs defined according to the Chothia numbering system: CDR-L1 comprising the sequence as set forth in SEQ ID NO: 42 or a variant thereof, CDR-L2 comprising the sequence as set forth in SEQ ID NO: 43 or a variant thereof, and CDR-L3 comprising the sequence as set forth in SEQ ID NO: 8 or a variant thereof.

In some specific embodiments, the antibody or antigen-binding fragment thereof that specifically binds to Nectin-4 comprises the following three heavy chain CDRs defined according to the Abm numbering system: CDR-H1 comprising the sequence as set forth in SEQ ID NO: 45 or a variant thereof, CDR-H2 comprising the sequence as set forth in SEQ ID NO: 46 or a variant thereof, CDR-H3 comprising the sequence as set forth in SEQ ID NO: 41 or a variant thereof. In other specific embodiments, the antibody or antigen-binding fragment thereof that specifically binds to Nectin-4 comprises the following three light chain CDRs defined according to the Abm numbering system: CDR-L1 comprising the sequence as set forth in SEQ ID NO: 42 or a variant thereof, CDR-L2 comprising the sequence as set forth in SEQ ID NO: 43 or a variant thereof, and CDR-L3 comprising the sequence as set forth in SEQ ID NO: 8 or a variant thereof.

In some specific embodiments, the antibody or antigen-binding fragment thereof that specifically binds to Nectin-4 comprises the following three heavy chain CDRs defined according to the Kabat numbering system: CDR-H1 comprising the sequence as set forth in SEQ ID NO: 47 or a variant thereof, CDR-H2 comprising the sequence as set forth in SEQ ID NO: 48 or 64 or a variant thereof, CDR-H3 comprising the sequence as set forth in SEQ ID NO: 41 or a variant thereof. In other specific embodiments, the antibody or antigen-binding fragment thereof that specifically binds to Nectin-4 comprises the following three light chain CDRs defined according to the Kabat numbering system: CDR-L1 comprising the sequence as set forth in SEQ ID NO: 42 or a variant thereof, CDR-L2 comprising the sequence as set forth in SEQ ID NO: 43 or a variant thereof, and CDR-L3 comprising the sequence as set forth in SEQ ID NO: 8 or a variant thereof.

In some specific embodiments, the antibody or antigen-binding fragment thereof that specifically binds to Nectin-4 comprises the following three heavy chain CDRs defined according to the IMGT numbering system: CDR-H1 comprising the sequence as set forth in SEQ ID NO: 49 or a variant thereof, CDR-H2 comprising the sequence as set forth in SEQ ID NO: 50 or a variant thereof, CDR-H3 comprising the sequence as set forth in SEQ ID NO: 51 or a variant thereof. In other specific embodiments, the antibody or antigen-binding fragment thereof that specifically binds to Nectin-4 comprises the following three light chain CDRs defined according to the IMGT numbering system: CDR-L1 comprising the sequence as set forth in SEQ ID NO: 52 or a variant thereof, CDR-L2 comprising the sequence as set forth in SEQ ID NO: 53 or a variant thereof, and CDR-L3 comprising the sequence as set forth in SEQ ID NO: 8 or a variant thereof.

In a specific embodiment, the antibody or antigen-binding fragment thereof that specifically binds to Nectin-4 comprises:

(a) CDRs of the following six heavy and light chains defined according to the Chothia numbering system: CDR-H1 comprising the sequence as set forth in SEQ ID NO: 39 or a variant thereof, CDR-H2 comprising the sequence as set forth in SEQ ID NO: 40 or a variant thereof, CDR-H3 comprising the sequence as set forth in SEQ ID NO: 41 or a variant thereof, CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof, or (b) CDRs of the following six heavy and light chains defined according to the Abm numbering system: CDR-H1 comprising the sequence as set forth in SEQ ID NO: 45 or a variant thereof, CDR-H2 comprising the sequence as set forth in SEQ ID NO: 46 or a variant thereof, CDR-H3 comprising the sequence as set forth in SEQ ID NO: 41 or a variant thereof, CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof, or (c) CDRs of the following six heavy and light chains defined according to the Kabat numbering system: CDR-H1 comprising the sequence as set forth in SEQ ID NO: 47 or a variant thereof, CDR-H2 comprising the sequence as set forth in SEQ ID NO: 48 or 64 or a variant thereof, CDR-H3 comprising the sequence as set forth in SEQ ID NO: 41 or a variant thereof, CDR-L1 comprising the sequence as set forth in SEQ ID NO: 42 or a variant thereof, CDR-L2 comprising the sequence as set forth in SEQ ID NO: 43 or a variant thereof, CDR-L3 comprising the sequence as set forth in SEQ ID NO: 8 or a variant thereof, or (d) CDRs of the following six heavy and light chains defined according to the IMGT numbering system: CDR-H1 comprising the sequence as set forth in SEQ ID NO: 49 or a variant thereof, CDR-H2 comprising the sequence as set forth in SEQ ID NO: 50 or a variant thereof, CDR-H3 comprising the sequence as set forth in SEQ ID NO: 51 or a variant thereof, CDR-L1 comprising the sequence as set forth in SEQ ID NO: 52 or a variant thereof, CDR-L2 comprising the sequence as set forth in SEQ ID NO: 53 or a variant thereof, CDR-L3 comprising the sequence as set forth in SEQ ID NO: 8 or a variant thereof.

In some embodiments of the antibody or antigen-binding fragment thereof that specifically binds to Nectin-4 as described above, the variant has a sequence identity of at least 80%, at least 85%, at least 90%, at least 91%, at least 92%, at least 93%, at least 94%, at least 95%, at least 96%, at least 97%, at least 98%, at least 99%, or 100% as compared to the sequence from which it is derived, or has a substitution, deletion or addition of one or more amino acids (e.g., substitution, deletion or addition of 1, 2 or 3 amino acids) as compared to the sequence from which it is derived; preferably, the substitution is a conservative substitution.

Framework Region (FR)

In some embodiments, the VH further comprises a heavy chain framework region (FR). In other embodiments, the VL further comprises a light chain framework region (FR). The heavy chain framework region and/or light chain framework region may each independently be derived from the framework regions of immunoglobulin of any species. Preferably, the heavy chain framework region and light chain framework region are each independently derived from the heavy chain framework region and light chain framework region of a human or murine immunoglobulin. In one embodiment, the heavy chain framework region and light chain framework region each independently comprise the heavy chain framework region and light chain framework region derived from a murine immunoglobulin, the heavy chain framework region and light chain framework region of a human immunoglobulin, or amino acid sequences derived from combinations thereof. In one embodiment, the heavy chain framework region and light chain framework region each independently comprise the amino acid sequences derived from the heavy chain framework region and light chain framework region of a human germline antibody.

In certain preferred embodiments, the VH of the antibody or antigen-binding fragment thereof of the present invention comprises a heavy chain framework region derived from a human immunoglobulin, and/or the VL of the antibody or antigen-binding fragment thereof comprises a light chain framework region derived from a human immunoglobulin. Accordingly, in certain preferred embodiments, the antibody or antigen-binding fragment thereof of the present invention is humanized. In such embodiments, the heavy chain framework region and/or light chain framework region of the antibody or antigen-binding fragment thereof of the present invention may comprise one or more non-human (e.g., murine) amino acid residues, for example, the heavy chain framework region and/or the light chain framework region may comprise one or more amino acid backmutations, and there are corresponding murine amino acid residues in these backmutations.

In a preferred embodiment, the antibody or antigen-binding fragment thereof that specifically binds to Nectin-4 comprises: a VH having the sequence as set forth in SEQ ID NO: 1 or a variant thereof. In yet another preferred embodiment, the antibody or antigen-binding fragment thereof that specifically binds to Nectin-4 comprises: a VL having the sequence as set forth in SEQ ID NO: 2 or a variant thereof.

In a preferred embodiment, the antibody or antigen-binding fragment thereof that specifically binds to Nectin-4 comprises: a VH having the sequence as set forth in SEQ ID NO: 1 or a variant thereof, and a VL having the sequence as set forth in SEQ ID NO: 2 or a variant thereof.

In a preferred embodiment, the antibody or antigen-binding fragment thereof that specifically binds to Nectin-4 comprises: a VH having the sequence as set forth in SEQ ID NO: 55 or a variant thereof. In yet another preferred embodiment, the antibody or antigen-binding fragment thereof that specifically binds to Nectin-4 comprises: a VL having the sequence as set forth in SEQ ID NO: 56 or a variant thereof.

In a preferred embodiment, the antibody or antigen-binding fragment thereof that specifically binds to Nectin-4 comprises: a VH having the sequence as set forth in SEQ ID NO: 55 or a variant thereof, and a VL having the sequence as set forth in SEQ ID NO: 56 or a variant thereof.

In yet another preferred embodiment, the antibody or antigen-binding fragment thereof that specifically binds to Nectin-4 comprises: a VH having the sequence as set forth in SEQ ID NO: 19 or a variant thereof. In yet another preferred embodiment, the antibody or antigen-binding fragment thereof that specifically binds to Nectin-4 comprises: a VL having the sequence as set forth in SEQ ID NO: 20 or a variant thereof.

In yet another preferred embodiment, the antibody or antigen-binding fragment thereof that specifically binds to Nectin-4 comprises: a VH having the sequence as set forth in SEQ ID NO: 19 or a variant thereof, and a VL having the sequence as set forth in SEQ ID NO: 20 a variant thereof.

In yet another preferred embodiment, the antibody or antigen-binding fragment thereof that specifically binds to Nectin-4 comprises: a VH having the sequence as set forth in SEQ ID NO: 57 or a variant thereof. In yet another preferred embodiment, the antibody or antigen-binding fragment thereof that specifically binds to Nectin-4 comprises: a VL having the sequence as set forth in SEQ ID NO: 58 or a variant thereof.

In yet another preferred embodiment, the antibody or antigen-binding fragment thereof that specifically binds to Nectin-4 comprises: a VH having the sequence as set forth in SEQ ID NO: 57 or a variant thereof, and a VL having the sequence as set forth in SEQ ID NO: 58 or a variant thereof.

In another preferred embodiment, the antibody or antigen-binding fragment thereof that specifically binds to Nectin-4 comprises: a VH having the sequence as set forth in SEQ ID NO: 37 or a variant thereof. In yet another preferred embodiment, the antibody or antigen-binding fragment thereof that specifically binds to Nectin-4 comprises: a VL having the sequence as set forth in SEQ ID NO: 38 or a variant thereof.

In another preferred embodiment, the antibody or antigen-binding fragment thereof that specifically binds to Nectin-4 comprises: a VH having the sequence as set forth in SEQ ID NO: 37 or a variant thereof, and a VL having the sequence as set forth in SEQ ID NO: 38 or a variant thereof.

In another preferred embodiment, the antibody or antigen-binding fragment thereof that specifically binds to Nectin-4 comprises: a VH having the sequence as set forth in SEQ ID NO: 59 or a variant thereof. In yet another preferred embodiment, the antibody or antigen-binding fragment thereof that specifically binds to Nectin-4 comprises: a VL having the sequence as set forth in SEQ ID NO: 60 or a variant thereof.

In another preferred embodiment, the antibody or antigen-binding fragment thereof that specifically binds to Nectin-4 comprises: a VH having the sequence as set forth in SEQ ID NO: 59 or a variant thereof, and a VL having the sequence as set forth in SEQ ID NO: 60 or a variant thereof.

In specific embodiments, the antibody or antigen-binding fragment thereof comprises: (1) a VH having the sequence as set forth in SEQ ID NO: 1 or a variant thereof and/or a VL having the sequence as set forth in SEQ ID NO: 2 or a variant thereof, or (2) a VH having the sequence as set forth in SEQ ID NO: 19 or a variant thereof and/or a VL having the sequence as set forth in SEQ ID NO: 20 or a variant thereof, or (3) a VH having the sequence as set forth in SEQ ID NO: 37 or a variant thereof and/or a VL having the sequence as set forth in SEQ ID NO: 38 or a variant thereof, or (4) a VH having the sequence as set forth in SEQ ID NO: 55 or a variant thereof and/or a VL having the sequence as set forth in SEQ ID NO: 56 or a variant thereof, or (5) a VH having the sequence as set forth in SEQ ID NO: 57 or a variant thereof and/or a VL having the sequence as set forth in SEQ ID NO: 58 or a variant thereof, or (6) VH having the sequence as set forth in SEQ ID NO: 59 or a variant thereof and/or VL having the sequence as set forth in SEQ ID NO: 60 or a variant thereof.

In an embodiment as described above, the variant has a sequence identity of at least 80%, at least 85%, at least 90%, at least 91%, at least 92%, at least 93%, at least 94%, at least 95%, at least 96%, at least 97%, at least 98%, at least 99% or 100% compared to the sequence from which it is derived. Alternatively, the variant has a substitution, deletion or addition of one or more amino acids (e.g., substitution, deletion or addition of 1, 2, 3, 4 or 5 amino acids) compared to the sequence from which it is derived. Preferably, the substitution is a conservative substitution.

Constant Region

In some embodiments, the anti-Nectin-4 antibody further comprises a heavy chain constant region. In another embodiment, the anti-Nectin-4 antibody further comprises a light chain constant region. The heavy chain constant region and light chain constant region can each be independently derived from the heavy chain constant region and light chain constant region of an immunoglobulin of any species. In a preferred embodiment, the heavy chain constant region and the light chain constant region are each independently derived from the heavy chain constant region or a variant thereof and the light chain constant region or a variant thereof of a murine immunoglobulin. In a more preferred embodiment, the heavy chain constant region and the light chain constant region are each independently derived from a heavy chain constant region or a variant thereof and a light chain constant region or a variant thereof of a human immunoglobulin. The variant has a substitution, deletion or addition of one or more amino acids (e.g., substitution, deletion or addition of up to 20, up to 15, up to 10, or up to 5 amino acids; for example, substitution, deletion or addition of 1, 2, 3, 4 or 5 amino acids) as compared to the wild-type sequence from which it is derived.

The heavy chain constant region may comprise an amino acid sequence selected from at least a portion of hinge region, CH1, CH2, CH3, or a combination thereof. In one embodiment, the heavy chain constant region comprises CH1. In one embodiment, the heavy chain constant region comprises CH1-hinge region-CH2. In one embodiment, the heavy chain constant region comprises CH1-hinge region-CH2-CH3. In some embodiments, the heavy chain constant region further comprises CH4. The heavy chain constant region can be derived from a heavy chain constant region of an immunoglobulin of any subtype (e.g., IgA, IgD, IgE, IgG, and IgM), any class (e.g., IgG1, IgG2, IgG3, IgG4, IgA1, and IgA2), or any subclass (e.g., IgG2a and IgG2b), or a combination thereof. Preferably, the heavy chain constant region is derived from an IgG (e.g., IgG1, IgG2, IgG3, IgG4) heavy chain constant region. In a preferred embodiment, the heavy chain constant region is derived from a human IgG1 heavy chain constant region.

The light chain constant region can be derived from a λ (Lambda) light chain or a κ (Kappa) light chain constant region. In a preferred embodiment, the light chain constant region is a human κ light chain constant region.

In a specific embodiment, the heavy chain constant region comprises the sequence as set forth in SEQ ID NO: 61 or a variant thereof. In a specific embodiment, the light chain constant region comprises the sequence as set forth in SEQ ID NO: 62 or a variant thereof. In these embodiments, the variant has a sequence identity of at least 80%, at least 85%, at least 90%, at least 91%, at least 92%, at least 93%, at least 94%, at least 95%, at least 96%, at least 97%, at least 98%, at least 99%, or 100% as compared to the sequence from which it was derived. Alternatively, the variant has a conservative substitution of up to 20 amino acids (e.g., a conservative substitution of up to 15, up to 10, or up to 5 amino acids; for example, a conservative substitution of 1, 2, 3, 4 or 5 amino acids) as compared to the sequence from which it is derived.

In a specific embodiment, the antibody or antigen-binding fragment thereof comprises a heavy chain and a light chain, wherein:

(a) the heavy chain comprises: a VH having the sequence as set forth in SEQ ID NO: 1 or a variant thereof and a heavy chain constant region having the sequence as set forth in SEQ ID NO: 61 or a variant thereof, and the light chain comprises: a VL having the sequence as set forth in SEQ ID NO: 2 or a variant thereof and a light chain constant region having the sequence as set forth in SEQ ID NO: 62 or a variant thereof, or (b) the heavy chain comprises: a VH having the sequence as set forth in SEQ ID NO: 19 or a variant thereof and a heavy chain constant region having the sequence as set forth in SEQ ID NO: 61 or a variant thereof, and the light chain comprises: a VL having the sequence as set forth in SEQ ID NO: 20 or a variant thereof and a light chain constant region having the sequence as set forth in SEQ ID NO: 62 or a variant thereof, or (c) the heavy chain comprises: a VH having the sequence as set forth in SEQ ID NO: 37 or a variant thereof and a heavy chain constant region having the sequence as set forth in SEQ ID NO: 61 or a variant thereof, and the light chain comprises: a VL having the sequence as set forth in SEQ ID NO: 38 or a variant thereof and a light chain constant region having the sequence as set forth in SEQ ID NO: 62 or a variant thereof, or (d) the heavy chain comprises: a VH having the sequence as set forth in SEQ ID NO: 55 or a variant thereof and a heavy chain constant region having the sequence as set forth in SEQ ID NO: 61 or a variant thereof, and the light chain comprises: a VL having the sequence as set forth in SEQ ID NO: 56 or a variant thereof and a light chain constant region having the sequence as set forth in SEQ ID NO: 62 or a variant thereof, or (e) the heavy chain comprises: a VH having the sequence as set forth in SEQ ID NO: 57 or a variant thereof and a heavy chain constant region having the sequence as set forth in SEQ ID NO: 61 or a variant thereof, and the light chain comprises: a VL having the sequence as set forth in SEQ ID NO: 58 or a variant thereof and a light chain constant region having the sequence as set forth in SEQ ID NO: 62 or a variant thereof, or (f) the heavy chain comprises: a VH having the sequence as set forth in SEQ ID NO: 59 or a variant thereof and a heavy chain constant region having the sequence as set forth in SEQ ID NO: 61 or a variant thereof, and the light chain comprises: a VL having the sequence as set forth in SEQ ID NO: 60 or a variant thereof and a light chain constant region having the sequence as set forth in SEQ ID NO: 62 or a variant thereof.

In one embodiment, the antibody or antigen-binding fragment thereof of the present invention is selected from the group consisting of scFv, Fab, Fab', $F(ab')_2$, Fv fragment, disulfide stabilized Fv (dsFv), diabody, bispecific antibody and multispecific antibody.

In some embodiments, the antibody or antigen-binding fragment thereof of the present invention is a murine, chimeric, or humanized antibody.

Murine Antibody

In one embodiment, the anti-Nectin-4 antibody of the present invention is a murine antibody, which comprises a VH and a VL, wherein the VH comprises the heavy chain CDR and heavy chain framework region as described above, and the VL comprises the light chain CDR and light chain framework region as described above, wherein the heavy chain framework region and the light chain framework region each independently comprises an amino acid sequences derived from a murine immunoglobulin framework region. In one embodiment, the anti-Nectin-4 antibody of the present invention is a monoclonal antibody produced from a mouse hybridoma cell.

In a specific embodiment, the murine antibody comprises a VH, which comprises the CDR-H1, CDR-H2, CDR-H3 as described in Group a of Table 1 and a heavy chain framework region, wherein the heavy chain framework region comprises an amino acid sequence derived from a murine immunoglobulin framework region. In a preferred embodiment, the murine antibody comprises a VH having the sequence as set forth in SEQ ID NO: 1 or a variant thereof. In yet another specific embodiment, the murine antibody further comprises a VL, which comprises the CDR-L1, CDR-L2, CDR-L3 as described in Group a of Table 2 and a light chain framework region, wherein the light chain framework region comprises an amino acid sequence derived from a murine immunoglobulin framework region. In a preferred embodiment, the murine antibody comprises a VL having the sequence as set forth in SEQ ID NO: 2 or a variant thereof.

In another specific embodiment, the murine antibody comprises a VH, which comprises the CDR-H1, CDR-H2, CDR-H3 as described in Group b of Table 1 and a heavy chain framework region, wherein the heavy chain framework region comprises an amino acid sequence derived from a murine immunoglobulin framework region. In a preferred embodiment, the murine antibody comprises a VH having the sequence as set forth in SEQ ID NO: 19 or a variant thereof.

In yet another specific embodiment, the murine antibody further comprises a VL, which comprises comprises CDR-L1, CDR-L2, CDR-L3 as described in Group b of Table 2 and a light chain framework region, wherein the light chain framework region comprises an amino acid sequence derived from a murine immunoglobulin framework region. In a preferred embodiment, the murine antibody comprises a VL having the sequence as set forth in SEQ ID NO: 20 or a variant thereof.

In yet another specific embodiment, the murine antibody comprises a VH, which comprises the CDR-H1, CDR-H2, CDR-H3 as described in Group c of Table 1 and a heavy chain framework region, wherein the heavy chain framework region comprises an amino acid sequence derived from a murine immunoglobulin framework region. In a preferred embodiment, the murine antibody comprises a VH having the sequence as set forth in SEQ ID NO: 37 or a variant thereof.

In yet another specific embodiment, the murine antibody further comprises a VL, which comprises the CDRL1, CDR-L2, CDR-L3 as described in Group c of Table 2 and a light chain framework region, wherein the light chain framework region comprises an amino acid sequence derived from a murine immunoglobulin framework region. In a preferred embodiment, the murine antibody comprises a VL having the sequence as set forth in SEQ ID NO: 38 or a variant thereof.

In an embodiment as described above, the variant has a sequence identity of at least 80%, at least 85%, at least 90%, at least 91%, at least 92%, at least 93%, at least 94%, at least 95%, at least 96%, at least 97%, at least 98%, at least 99% or 100% as compared to the sequence from which it is derived. Alternatively, the variant has a substitution, deletion or addition of one or more amino acids (e.g., a substitution, deletion or addition of 1, 2, 3, 4 or 5 amino acids) as compared to the sequence from which it is derived. Preferably, the substitution is a conservative substitution.

In a specific embodiment, the murine antibody comprises a VH having the sequence as set forth in SEQ ID NO:1 and a VL having the sequence as set forth in SEQ ID NO:2.

In another specific embodiment, the murine antibody comprises a VH having the sequence as set forth in SEQ ID NO:19 and a VL having the sequence as set forth in SEQ ID NO:20.

In yet another specific embodiment, the murine antibody comprises a VH having the sequence as set forth in SEQ ID NO:37 and a VL having the sequence as set forth in SEQ ID NO:38.

Chimeric Antibody

In one embodiment, the anti-Nectin-4 antibody of the present invention is a chimeric antibody. In some embodiments, the chimeric antibody comprises the heavy chain CDR and/or light chain CDR of murine antibody as described above. In some embodiments, the chimeric antibody comprises the heavy chain variable region and/or the light chain variable region of murine antibody as described above. In some embodiments, the chimeric antibody comprises the heavy chain variable region and the light chain variable region of murine antibody as described above, and a heavy chain constant region and/or a light chain constant region, wherein the heavy chain constant region is derived from a heave chain constant region of a non-murine immunoglobulin, and/or the light chain constant region is derived from a light chain constant region of a non-murine immunoglobulin. In a preferred embodiment, the heavy chain constant region is derived from a human immunoglobulin heavy chain constant region, and/or the light chain constant region is derived from a human immunoglobulin light chain constant region. In a preferred embodiment, the heavy chain constant region is derived from a human immunoglobulin heavy chain constant region and the light chain constant region is derived from a human immunoglobulin light chain constant region.

In some embodiments, the chimeric antibody comprises the CDR-H1, CDR-H2, CDR-H3 of murine antibody as described in Group a of Table 1. In some embodiments, the chimeric antibody further comprises the CDR-L1, CDR-L2, CDR-L3 of murine antibody as described in Group a of Table 2.

In a specific embodiment, the chimeric antibody comprises a VH having the sequence as set forth in SEQ ID NO: 1 or a variant thereof. In a specific embodiment, the chimeric antibody further comprises a VL having the sequence as set forth in SEQ ID NO: 2 or a variant thereof.

In another specific embodiment, the chimeric antibody comprises a VH having the sequence as set forth in SEQ ID NO: 19 or a variant thereof. In a specific embodiment, the chimeric antibody further comprises a VL having the sequence as set forth in SEQ ID NO: 20 or a variant thereof.

In yet another specific embodiment, the chimeric antibody comprises a VH having the sequence as set forth in SEQ ID NO: 37 or a variant thereof. In a specific embodiment, the chimeric antibody further comprises a VL having the sequence as set forth in SEQ ID NO: 38 or a variant thereof.

In an embodiment as described above, the variant has a sequence identity of at least 80%, at least 85%, at least 90%, at least 91%, at least 92%, at least 93%, at least 94%, at least 95%, at least 96%, at least 97%, at least 98%, at least 99% or 100% as compared to the sequence from which it is derived. Alternatively, the variant has a substitution, deletion or addition of one or more amino acids (e.g., a substitution, deletion or addition of 1, 2, 3, 4 or 5 amino acids) as compared to the sequence from which it is derived. Preferably, the substitution is a conservative substitution.

In some embodiments, the chimeric antibody as described above further comprises a heavy chain constant region and/or a light chain constant region. In a preferred embodiment, the heavy chain constant region is derived from a human immunoglobulin heavy chain constant region and the light chain constant region is derived from a human immunoglobulin light chain constant region. In one embodiment, the heavy chain constant region is derived from a human IgG1, IgG2, IgG3 or IgG4 heavy chain constant region. In one embodiment, the heavy chain constant region is derived from a human IgG1 heavy chain constant region. In one embodiment, the light chain constant region is derived from a human λ or κ light chain constant region. In one embodiment, the light chain constant region is derived from a human κ light chain constant region. In a specific embodiment, the heavy chain constant region comprises the amino acid sequence as set forth in SEQ ID NO: 61 or a variant thereof. In a specific embodiment, the light chain constant region comprises the amino acid sequence as set forth in SEQ ID NO: 62 or a variant thereof. In these embodiments, the variant has a sequence identity of at least 80%, at least 85%, at least 90%, at least 91%, at least 92%, at least 93%, at least 94%, at least 95%, at least 96%, at least 97%, at least 98%, at least 99%, or 100% as compared to the sequence from which it was derived. Alternatively, the variant has a conservative substitution of up to 20 amino acids (e.g., a conservative substitution of up to 15, up to 10, or up to 5 amino acids; for example, a conservative substitution of 1, 2, 3, 4 or 5 amino acids) as compared to the sequence from which it is derived.

In a specific embodiment, the chimeric antibody comprises a heavy chain and a light chain, the heavy chain comprising: a VH having the sequence as set forth in SEQ ID NO: 1 and a heavy chain constant region having the sequence as set forth in SEQ ID NO: 61, the light chain comprising: a VL having the sequence as set forth in SEQ ID NO:2 and a light chain constant region having the sequence as set forth in SEQ ID NO:62.

In another specific embodiment, the chimeric antibody comprises a heavy chain and a light chain, the heavy chain comprising: a VH having the sequence as set forth in SEQ ID NO: 19 and a heavy chain constant region having the sequence as set forth in SEQ ID NO: 61, the light chain comprising: a VL having the sequence as set forth in SEQ ID NO:20 and a light chain constant region having the sequence as set forth in SEQ ID NO:62.

In yet another specific embodiment, the chimeric antibody comprises a heavy chain and a light chain, the heavy chain comprising: a VH having the sequence as set forth in SEQ ID NO:37 and a heavy chain constant region having the sequence as set forth in SEQ ID NO:61, the light chain comprising: a VL having the sequence as set forth in SEQ ID NO:38 and a light chain constant region having the sequence as set forth in SEQ ID NO:62.

Humanized Antibody

In one embodiment, the anti-Nectin-4 antibody of the present invention is a humanized antibody, which comprises a VH and a VL, wherein the VH comprises the above-described heavy chain CDR and a heavy chain framework region, and the VL comprises the above-described light chain CDR and a light chain framework region, wherein the heavy chain framework region and the light chain framework region each independently comprises an amino acid sequence derived from human immunoglobulin heavy chain framework region and light chain framework region. In such embodiments, the heavy chain framework region and/or the light chain framework region may comprise one or more non-human (e.g., murine) amino acid residues, for example, the heavy chain framework region and/or the light chain framework region may comprise one or more amino acid back mutations, and there are corresponding murine amino acid residues in these backmutations. The humanized antibody can be generated from a non-human antibody (e.g., murine or chimeric antibody). In one embodiment, the humanized antibody is prepared from the anti-Nectin-4 murine antibody of the present invention as described in the Examples of the present invention.

In a specific embodiment, the humanized antibody comprises the CDR-H1 or a variant thereof, CDR-H2 or a variant thereof, CDR-H3 or a variant thereof of murine antibody as described above. In a specific embodiment, the humanized antibody further comprises the CDR-L1 or a variant thereof, CDR-L2 or a variant thereof, CDR-L3 or a variant thereof of murine antibody as described above.

In a specific embodiment, the humanized antibody comprises a VH, which comprises the CDR-H1 or a variant thereof, CDR-H2 or a variant thereof, CDR-H3 or a variant thereof of murine antibody as described above, and a heavy chain framework region, wherein the heavy chain framework region comprises an amino acid sequence derived from a human immunoglobulin heavy chain framework region. In yet another specific embodiment, the humanized antibody further comprises a VL, which comprises the CDR-L1 or a variant thereof, CDR-L2 or a variant thereof, CDR-L3 or a variant thereof of murine antibody as described above, and a light chain framework region, wherein the light chain framework region comprises an amino acid sequence derived from a human immunoglobulin light chain framework region.

In a specific embodiment, the humanized antibody comprises a VH, as defined by the Chothia numbering system, which comprises the CDR-H1 as set forth in SEQ ID NO: 3, CDR-H2 as set forth in SEQ ID NO: 4, CDR-H3 as set forth in SEQ ID NO: 5, and a heavy chain framework region, wherein the heavy chain framework region comprises an amino acid sequence derived from a human immunoglobulin heavy chain framework region. In yet another specific embodiment, the humanized antibody further comprises a VL, as defined by the Chothia numbering system, which comprises the CDR-L1 as set forth in SEQ ID NO: 6, CDR-L2 as set forth in SEQ ID NO: 7, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VH, as defined by the Abm numbering system, which comprises the CDR-H1 as set forth in SEQ ID NO: 9, CDR-H2 as set forth in SEQ ID NO: 10, CDR-H3 as set forth in SEQ ID NO: 5, and a heavy chain framework region, wherein the heavy chain framework region comprises an amino acid sequence derived from a human immunoglobulin heavy chain framework region. In yet another specific embodiment, the humanized antibody further comprises a VL, as defined by the Abm numbering system, which comprises the CDR-L1 as set forth in SEQ ID NO: 6, CDR-L2 as set forth in SEQ ID NO: 7, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VH, as defined by the Kabat numbering system, which comprises the CDR-H1 as set forth in SEQ ID NO: 11, CDR-H2 as set forth in SEQ ID NO: 12 or 63, CDR-H3 as set forth in SEQ ID NO: 5, and a heavy chain framework region, wherein the heavy chain framework region comprises an amino acid sequence derived from a human immunoglobulin heavy chain framework region. In yet another specific embodiment, the humanized antibody further comprises a VL, as defined by the Kabat numbering system, which comprises the CDR-L1 as set forth in SEQ ID NO: 6, CDR-L2 as set forth in SEQ ID NO: 7, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VH, as defined by the IMGT numbering system, which comprises the CDR-H1 as set forth in SEQ ID NO: 13, CDR-H2 as set forth in SEQ ID NO: 14, CDR-H3 as set forth in ID NO: 15, and a heavy chain framework region, wherein the heavy chain framework region comprises an amino acid sequence derived from a human immunoglobulin heavy chain framework region. In yet another specific embodiment, the humanized antibody further comprises a VL, as defined by the IMGT numbering system, which comprises the CDR-L1 as set forth in SEQ ID NO: 16, CDR-L2 as set forth in SEQ ID NO: 17, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VL having the sequence as set forth in SEQ ID NO: 56 or a variant thereof. In one embodiment, the humanized antibody comprises a VH having the sequence as set forth in SEQ ID NO: 55 or a variant thereof.

In a specific embodiment, the humanized antibody comprises a VH, as defined by the Chothia numbering system, which comprises the CDR-H1 as set forth in SEQ ID NO: 21 or 18, CDR-H2 as set forth in SEQ ID NO: 22, CDR-H3 as set forth in SEQ ID NO: 23, and a heavy chain framework region, wherein the heavy chain framework comprises an amino acid sequence derived from a human immunoglobulin heavy chain framework region. In yet another specific embodiment, the humanized antibody further comprises a VL, as defined by the Chothia numbering system, which comprises the CDR-L1 as set forth in SEQ ID NO: 24, CDR-L2 as set forth in SEQ ID NO: 25, CDR-L3 as set forth in SEQ ID NO: 26, and a light chain framework region, wherein the light chain framework region comprises an amino acid sequence derived from a human immunoglobulin light chain framework region.

In a specific embodiment, the humanized antibody comprises a VH, as defined by the Abm numbering system, which comprises the CDR-H1 as set forth in SEQ ID NO: 27 or 36, CDR-H2 as set forth in SEQ ID NO: 28, CDR-H3 as set forth in SEQ ID NO: 23, and a heavy chain framework region, wherein the heavy chain framework region comprises an amino acid sequence derived from a human immunoglobulin heavy chain framework region. In yet another specific embodiment, the humanized antibody further comprises a VL, as defined by the Abm numbering system, which comprises the CDR-L1 as set forth in SEQ ID NO: 24, CDR-L2 as set forth in SEQ ID NO: 25, CDR-L3 as set forth in SEQ ID NO: 26, and a light chain framework region, wherein the light chain framework region comprises an amino acid sequence derived from a human immunoglobulin light chain framework region.

In a specific embodiment, the humanized antibody comprises a VH, as defined by the Kabat numbering system, which comprises the CDR-H1 as set forth in SEQ ID NO: 29 or 44, CDR-H2 as set forth in SEQ ID NO: 30, CDR-H3 as set forth in SEQ ID NO: 23, and a heavy chain framework region, wherein the heavy chain framework region comprises an amino acid sequence derived from a human immunoglobulin heavy chain framework region. In yet another specific embodiment, the humanized antibody further comprises a VL, as defined by the Kabat numbering system, which comprises the CDR-L1 as set forth in SEQ ID NO: 24, CDR-L2 as set forth in SEQ ID NO: 25, CDR-L3 as set forth in SEQ ID NO: 26, and a light chain framework region, wherein the light chain framework region comprises an amino acid sequence derived from a human immunoglobulin light chain framework region.

In a specific embodiment, the humanized antibody comprises a VH, as defined by the IMGT numbering system, which comprises the CDR-H1 as set forth in SEQ ID NO: 31 or 54, CDR-H2 as set forth in SEQ ID NO: 32, CDR-H3 as set forth in SEQ ID NO: 33, and a heavy chain framework region, wherein the heavy chain framework region comprises an amino acid sequence derived from a human immunoglobulin heavy chain framework region. In yet another specific embodiment, the humanized antibody further comprises a VL, as defined by the IMGT numbering system, which comprises the CDR-L1 as set forth in SEQ ID NO: 34, CDR-L2 as set forth in SEQ ID NO: 35, CDR-L3 as set forth in SEQ ID NO: 26, and a light chain framework region, wherein the light chain framework region comprises an amino acid sequence derived from a human immunoglobulin light chain framework region.

In a specific embodiment, the humanized antibody comprises a VL having the sequence as set forth in SEQ ID NO: 58 or a variant thereof. In one embodiment, the humanized antibody comprises a VH having the sequence as set forth in SEQ ID NO: 57 or a variant thereof.

In a specific embodiment, the humanized antibody comprises a VH, as defined by the Chothia numbering system, which comprises the CDR-H1 as set forth in SEQ ID NO: 39, CDR-H2 as set forth in SEQ ID NO: 40, CDR-H3 as set forth in SEQ ID NO: 41, and a heavy chain framework region, wherein the heavy chain framework region comprises an amino acid sequence derived from a human immunoglobulin heavy chain framework region. In yet another specific embodiment, the humanized antibody further comprises a VL, as defined by the Chothia numbering system, which comprises the CDR-L1 as set forth in SEQ ID NO: 42, CDR-L2 as set forth in SEQ ID NO: 43, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VH, as defined by the Abm numbering system, which comprises the CDR-H1 as set forth in SEQ ID NO: 45, CDR-H2 as set forth in SEQ ID NO: 46, CDR-H3 as set forth in SEQ ID NO: 41, and a heavy chain framework region, wherein the heavy chain framework region comprises an amino acid sequence derived from a human immunoglobulin heavy chain framework region. In yet another specific embodiment, the humanized antibody further comprises a VL, as defined by the Abm numbering system, which comprises the CDR-L1 as set forth in SEQ ID NO: 42, CDR-L2 as set forth in SEQ ID NO: 43, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VH, as defined by the Kabat numbering system, which comprises the CDR-H1 as set forth in SEQ ID NO: 47, CDR-H2 as as set forth in SEQ ID NO: 48 or 64, CDR-H3 as set forth in SEQ ID NO: 41, and a heavy chain framework region, wherein the heavy chain framework region comprises an amino acid sequence derived from a human immunoglobulin heavy chain framework region. In yet another specific embodiment, the humanized antibody further comprises a VL, as defined by the Kabat numbering system, which comprises the CDR-L1 as set forth in SEQ ID NO: 42, CDR-L2 as set forth in SEQ ID NO: 43, CDR-L3 as set forth in SEQ ID NO: 8, and a light chain framework region, wherein the light chain framework region comprises an amino acid sequence derived from a human immunoglobulin light chain framework region.

In a specific embodiment, the humanized antibody comprises a VH, as defined by the IMGT numbering system, which comprises the CDR-H1 as set forth in SEQ ID NO: 49, CDR-H2 as set forth in SEQ ID NO: 50, CDR-H3 as set forth in SEQ ID NO: 51, and a heavy chain framework region, wherein the heavy chain framework region comprises an amino acid sequence derived from a human immunoglobulin heavy chain framework region. In yet another specific embodiment, the humanized antibody further comprises a VL, as defined by the IMGT numbering system, which comprises the CDR-L1 as set forth in SEQ ID NO: 52, CDR-L2 as set forth in SEQ ID NO: 53, CDR-L3 as set forth in SEQ ID NO: 8, and a light chain framework region, wherein the light chain framework region comprises an amino acid sequence derived from a human immunoglobulin light chain framework region.

In one embodiment, the humanized antibody comprises a VL having the sequence as set forth in SEQ ID NO: 60 or a variant thereof. In one embodiment, the humanized antibody comprises a VH having the sequence as set forth in SEQ ID NO: 59 or a variant thereof.

In an embodiment as described above, the variant has a sequence identity of at least 80%, at least 85%, at least 90%, at least 91%, at least 92%, at least 93%, at least 94%, at least 95%, at least 96%, at least 97%, at least 98%, at least 99% or 100% as compared to the sequence from which it is derived. Alternatively, the variant has a substitution, deletion or addition of one or more amino acids (e.g., a substitution, deletion or addition of 1, 2, 3, 4 or 5 amino acids) as compared to the sequence from which it is derived. Preferably, the substitution is a conservative substitution.

In certain embodiments, the antibody or antigen-binding fragment thereof of the present invention comprise a heavy chain variable region (VH) and/or a light chain variable region (VL), wherein, as compared to the heavy chain variable region and/or light chain variable region described in the aforementioned humanized antibody, at least one CDR and/or framework region comprises an amino acid mutation, wherein the amino acid mutation is a substitution, deletion or addition of one or more amino acids, or any combination thereof (e.g., substitution, deletion or addition of 1, 2 or 3 amino acids, or any combination thereof). Preferably, the substitution is a conservative substitution.

In some embodiments, the anti-Nectin-4 humanized antibody further comprises a heavy chain constant region. In one embodiment, the heavy chain constant region is derived from a human IgG1, IgG2, IgG3 or IgG4 heavy chain constant region. In one embodiment, the heavy chain constant region is derived from a human IgG1 heavy chain constant region. In one embodiment, the heavy chain constant region comprises the amino acid sequence as set forth in SEQ ID NO: 61 or a variant thereof.

In some embodiments, the anti-Nectin-4 humanized antibody further comprises a light chain constant region. In one embodiment, the light chain constant region is derived from a human λ or κ light chain constant region. In one embodiment, the light chain constant region is derived from a human κ light chain constant region. In one embodiment, the light chain constant region comprises the amino acid sequence as set forth in SEQ ID NO: 62 or a variant thereof.

In an embodiment as described above, the variant has a sequence identity of at least 80%, at least 85%, at least 90%, at least 91%, at least 92%, at least 93%, at least 94%, at least 95%, at least 96%, at least 97%, at least 98%, at least 99% or 100% as compared to the sequence from which it is derived. Alternatively, the variant has a conservative substitution of up to 20 amino acids (e.g., a conservative substitution of up to 15, up to 10, or up to 5 amino acids; for example, a conservative substitution of 1, 2, 3, 4 or 5 amino acids) as compared to the sequence from which it is derived.

In a specific embodiment, the humanized antibody comprises a heavy chain and a light chain, the heavy chain comprising: a VH having the sequence as set forth in SEQ ID NO:55 and a heavy chain constant region having the sequence as set forth in SEQ ID NO:61, the light chain comprising: a VL having the sequence as set forth in SEQ ID NO: 56 and a light chain constant region having the sequence as set forth in SEQ ID NO: 62.

In a specific embodiment, the humanized antibody comprises a heavy chain and a light chain, the heavy chain comprising: a VH having the sequence as set forth in SEQ ID NO:57 and a heavy chain constant region having the sequence as set forth in SEQ ID NO:61, the light chain comprising: a VL with the sequence as set forth in SEQ ID NO: 58 and a light chain constant region with the sequence as set forth in SEQ ID NO: 62.

In a specific embodiment, the humanized antibody comprises a heavy chain and a light chain, the heavy chain comprising: a VH having the sequence as set forth in SEQ ID NO:59 and a heavy chain constant region having the sequence as set forth in SEQ ID NO:61, the light chain comprising: a VL having the sequence as set forth in SEQ ID NO: 60 and a light chain constant region having the sequence as set forth in SEQ ID NO: 62.

The anti-Nectin-4 antibody or antigen-binding fragment thereof of the present invention can be prepared and produced using methods known in the art. Such methods can comprise, for example, preparing and isolating the antibody or antigen-binding fragment from a phage display library, yeast display library, immortalized B cell (e.g., mouse B cell hybridoma cell or EBV immortalized B cell). Methods for immunizing animals, for example, immunizing an animal (e.g., mouse) with an antigen or DNA encoding the antigen, can also be used, and an antibody-expressing B cell can be isolated from the immunized animals. Preferably, the antibody-expressing B cell is immortalized, for example, prepared as a hybridoma or EBV immortalized B cell. A host cell can also be transformed with a nucleic acid molecule or expression vector encoding the antibody or antigen-binding fragment thereof of the present invention, and then the anti-Nectin-4 or antigen-binding fragment thereof of the present invention is expressed from the host cell. In some embodiments, the anti-Nectin-4 antibody of the present invention is obtained from an immunized animal, for example, from a mouse immunized with human Nectin-4 protein.

Multispecific Antibody

In one aspect, the present invention provides a multispecific antibody, which comprises the anti-Nectin-4 antibody or antigen-binding fragment thereof of the present invention and at least one other antibody or antigen-binding fragment or antibody analog thereof, such that the multispecific antibody is capable of binding to Nectin-4 as well as at least one other antigen.

In one embodiment, the multispecific antibody is a bispecific antibody, trispecific antibody or tetraspecific antibody. In one embodiment, the multispecific antibody is a bispecific diabody, which comprises a first scFv (or scdsFv) and a second scFv (or scdsFv), wherein the first scFv (or scdsFv) comprises the VH of the present invention and a VL of other antibody that are linked by a short peptide linker, the second scFv (or scdsFv) comprises the VL of the present invention and a VH of the other antibody that are linked by a shorter peptide linker, the other antibody binds to an antigen other than Nectin-4, and the short peptide linkers comprise 5-10 amino acid residues.

In one embodiment, the other antigen is a cell surface protein, receptor or receptor subunit. The cell surface protein can be, for example, an immune cell receptor. The immune cell can be, for example, an immune effector cell, such as natural killer (NK) cell, natural killer T (NKT) cell, cytotoxic T (CTL) cell. In a preferred embodiment, the bispecific antibody can bind to both Nectin-4 and PD-1.

The multispecific antibody is a multivalent antibody, for example, which can be bivalent, trivalent, tetravalent or more.

In a preferred embodiment, the multispecific antibody comprises an antigen-binding fragment selected from the group consisting of scFv, dsFv, scdsFv, Fab, scFab, Fab', $F(ab')_2$.

The multispecific antibody may also comprise an antibody heavy chain constant region and/or a light chain constant region. The heavy chain constant region may comprise an amino acid sequence selected from at least a portion of hinge region, CH1, CH2, CH3, or a combination thereof. Preferably, the heavy chain constant region has CH1.

Methods for constructing multispecific antibodies using antibodies or antibody fragments of interest are well known to those skilled in the art (see, for example, International Patent Application Publication No. WO 93/08829; Suresh et al., (1986) Methods in Enzymology, 121: 210; Traunecker et al., (1991) EMBO, 10: 3655-3659).

The multispecific antibody can be produced and isolated using various techniques known in the art. For example, recombinant DNA techniques can be used to obtain a nucleic acid molecule encoding the multispecific antibody, optionally the nucleic acid molecule is cloned into an expression vector, then a host cell is transformed with the nucleic acid molecule or expression vector, the transformed host cell is cultured under suitable conditions to allow the expression of the nucleic acid or expression vector, and finally the multi-specific antibody is isolated and purified from the host cell or a culture medium thereof.

Fusion Protein

In yet another aspect, the present invention provides a fusion protein, which comprises the antibody or antigen-binding fragment thereof of the present invention, and an additional biologically active polypeptide.

In preferred embodiments, the additional biologically active polypeptide is a polypeptide or protein having a therapeutic activity, binding activity or enzymatic activity. Non-limiting examples of the biologically active polypeptide can include, but are not limited to, protein toxin (e.g., diphtheria toxin, ricin), enzyme (e.g., urease, horseradish peroxidase), cytokine.

Nucleic Acid, Vector and Host Cell

In another aspect, the present invention provides a nucleic acid molecule, which comprises a polynucleotide sequence encoding the anti-Nectin-4 antibody or antigen-binding fragment of the present invention. The nucleic acid can be obtained using methods known in the art, for example, by isolation from phage display library, yeast display library, immunized animal, immortalized cell (e.g., mouse B cell hybridoma cell, EBV-mediated immortalized B cell) or by chemical synthesis. The nucleic acid molecule of the present invention may be codon-optimized for the host cell used for expression. The nucleic acid molecule can be isolated.

In yet another aspect, the present invention also provides a vector comprising the nucleic acid molecule. In one embodiment, the nucleic acid molecule of the present invention is prepared as a recombinant nucleic acid. In one embodiment, the nucleic acid molecule of the present invention is cloned into an expression vector. The expression vector may further comprise an additional polynucleotide sequence, such as regulatory sequence and antibiotic resistance gene. The recombinant nucleic acid comprising the nucleic acid of the present invention can be prepared using techniques well known in the art, such as chemical synthesis, recombinant DNA techniques (e.g., polymerase chain reaction (PCR) techniques), etc. (see, Sambrook, J., E. F. Fritsch, and T. Maniatis. (1989). Molecular cloning: a laboratory manual, 2nd ed. Cold Spring Harbor Laboratory, Cold Spring Harbor, N.Y.). The expression vector may also comprise a polynucleotide sequence encoding a polypeptide or protein, wherein the polypeptide or protein can facilitate the detection and/or isolation of the expressed antibody or antigen-binding fragment. Such polypeptide or protein may include, but be not limited to, affinity tag (e.g., biotin, polyhistidine tag ($His_6$), or glutathione S-transferase (GSH) tag), polypeptide comprising protease cleavage site, and reporter protein (e.g., fluorescent protein). The nucleic acid molecule of the present invention may be present in one or more vectors. In some embodiments, the expression vector is a DNA plasmid, for example, a DNA plasmid for expression in bacterial, yeast, or mammalian cells. In other embodiments, the expression vector is a viral vector. In other embodiments, the expression vector is a phage vector or a phagemid vector.

The present invention also provides a host cell, which comprises at least one nucleic acid or vector as described above. In a preferred embodiment, the host cell herein is used to express the anti-Nectin-4 antibody or antigen-binding fragment thereof of the present invention. Examples of the host cell include, but are not limited to, prokaryotic cells (e.g., bacteria, for example, *E. coli*), eukaryotic cells (e.g., yeast, insect cells, mammalian cells).

Bacteria (e.g., *E. coli* BL21(DE3)) are particularly advantageous for expressing smaller antigen-binding fragments such as Fv, scFv, Fab and Fab' fragments. In some embodiments, the nucleic acid molecule encoding the heavy chain variable region and light chain variable region is cloned into a single vector and introduced into BL21(DE3). Mammalian host cells suitable for antibody expression include, but are not limited to, myeloma cell, HeLa cell, HEK cell (e.g., HEK 293 cell), Chinese hamster ovary (CHO) cell, and other mammalian cells suitable for antibody expression.

The present invention also provides a method for producing the anti-Nectin-4 antibody or antigen-binding fragment of the present invention in a host cell, wherein the method comprises the following steps:

(I) transforming the host cell with at least one nucleic acid or expression vector described herein, (II) culturing the transformed host cell under suitable conditions to permit the expression of the nucleic acid or expression vector, and (III) isolating and purifying the antibody or antigen-binding fragment of the present invention from the host cells or a culture medium thereof.

In some embodiments, a single vector that comprises the polynucleotide sequence encoding the heavy chain and the light chain is used. In some embodiments, two vectors are used, wherein one encodes the antibody light chain and the other encodes the antibody heavy chain. In some embodiments, the host cell further comprises a partner plasmid, which can help increase the solubility, stability and/or folding of the antibody or antibody fragment. Techniques for isolating and purifying antibody from host cells are well known to those skilled in the art.

Antibody Conjugate

The present invention also provides an antibody conjugate, which comprises the antibody or antigen-binding fragment thereof of the present invention conjugated to at least one therapeutic agent. Antibody drug conjugate (ADC) is a typical type of antibody conjugate, wherein the therapeutic agent can be, for example, a cytotoxic agent.

In some preferred embodiments, the antibody conjugate of the present invention is capable of targeting a Nectin-4 positive target cell and tracking or killing the target cell. In some more preferred embodiments, the antibody conjugate of the present invention selectively kills a Nectin-4 positive cancer cell. In some embodiments, the cancer cell is selected from gastric cancer cell, breast cancer cell, bladder cancer cell, lung cancer cell, liver cancer cell, colon cancer cell, rectal cancer cell, head and neck cancer cell, and ovarian cancer cell.

The therapeutic agent may be selected from the group consisting of cytotoxic agent, therapeutic antibody (e.g., antibody or antigen-binding fragment thereof that specifically binds to an additional antigen), radioisotope, oligonucleotide and analog thereof (e.g., interfering RNA), biologically active peptide, protein toxin (e.g., diphtheria toxin, ricin) and enzyme (e.g., urease). The cytotoxic agent refers to a substance that inhibits or reduces the cell's activity or function, and/or kills the cell. Examples of the cytotoxic agent may include, but are not limited to: maytansinoids (e.g., maytansine), auristatins (e.g., MMAF, MMAE, MMAD), duostatin, cryptophycin, *vinca* alkaloids (e.g., vinblastine, vincristine), colchicines, dolastatins, taxanes, paclitaxel, docetaxel, cabazitaxel, enediynes antibiotics, cytochalasins, camptothecins, anthracyclines (e.g., daunorubicin, dihydroxyanthraquinone, doxorubicin), cytotoxic antibiotics (e.g., mitomycin, actinomycin, duocarmycin (e.g., CC-1065), aureomycin, duomycin, calicheamicin, endomycin, phenomycin), doxorubicin, daunorubicin, calicheamicin, cisplatin, ethidium bromide, bleomycin, mitomycin, mithramycin, pladienolide, podophyllotoxin, etoposide, mitoxantrone, 5-fluorouracil, cytarabine, gemcitabine, mercaptopurine, pentostatin, fludarabine, cladribine, nelarabine, carmustine, lomustine, methotrexate, melphalan, teniposide, glucocorticoid, etc.

The radioisotope may be selected from, for example, $^{212}$Bi, $^{213}$Bi, $^{131}$I, $^{125}$I, $^{111}$In, $^{177}$Lu, $^{186}$Re, $^{188}$Re, $^{153}$Sm, $^{90}$Y. The radioisotopically labeled antibody may also be referred to as radio immunoconjugate.

In one embodiment, the therapeutic agent is a molecule with anti-tumor biological activity. The molecule with anti-tumor biological activity includes, but is not limited to, cytotoxic agent, chemotherapeutic agent, radioisotope, immune checkpoint inhibitor, antibody targeting tumor-specific antigen, and other anti-tumor drugs. In a preferred embodiment, the therapeutic agent is a cytotoxic agent. In yet another preferred embodiment, the therapeutic agent is a radioisotope.

In a Specific Embodiment, the Therapeutic Agent is,

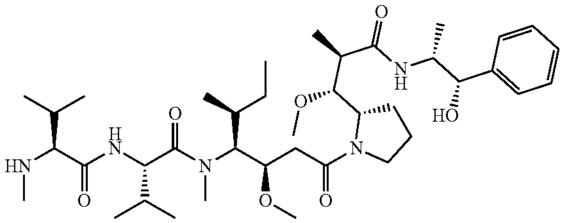

,

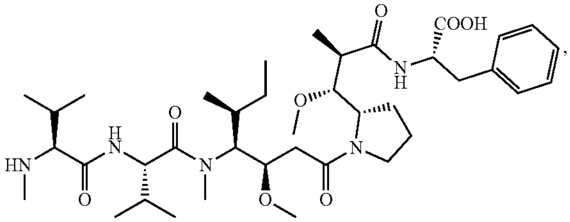

,

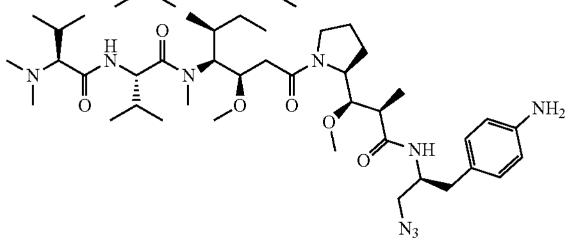

or

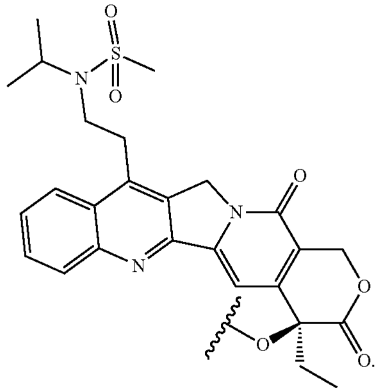

.

The therapeutic agent can be conjugated to the antibody or antigen-binding fragment of the present invention through a linker using any technique known in the art. The linker may comprise a reactive group for covalent conjugation, such as amine, hydroxylamine, maleimide, carboxyl, phenyl, thiol, sulfhydryl, or hydroxyl group. The linker can be cleavable or non-cleavable. The cleavable linker is, for example, an enzymatically cleavable linker (e.g., peptide containing protease cleavage site), pH sensitive linker (e.g., hydrazone-type linker), or reducible linker (e.g., disulfide bond).

In one embodiment, the linker comprises a reactive group selected from the group consisting of amine, hydroxylamine, maleimide, carboxyl, phenyl, thiol, sulfhydryl, and hydroxyl groups. In one embodiment, the linker is a chemical bond. In one embodiment, the linker comprises an amino acid or a peptide consisting of 2-10 amino acids. The amino acid can be a natural or non-natural amino acid.

In a preferred embodiment, the linker is selected from the group consisting of Val, Cit, Phe,

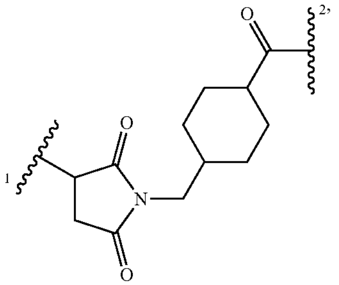,
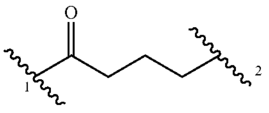,
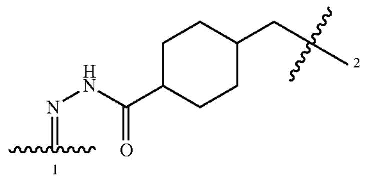,
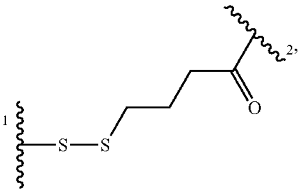,
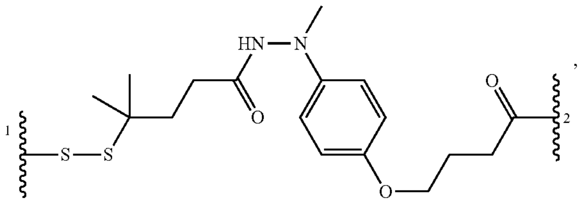,
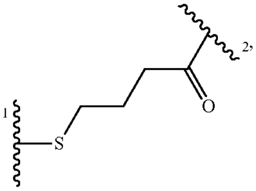,
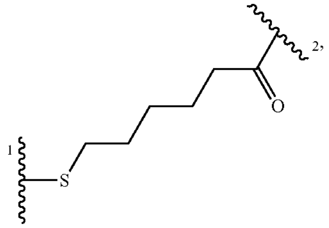,
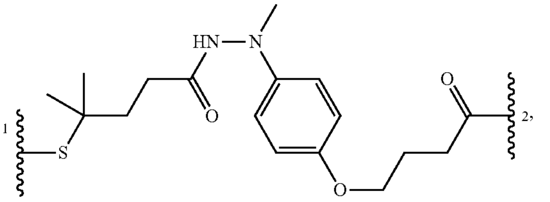,
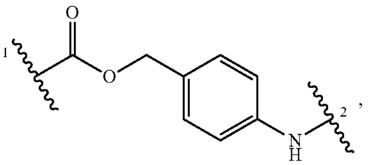,
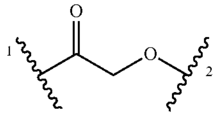 or
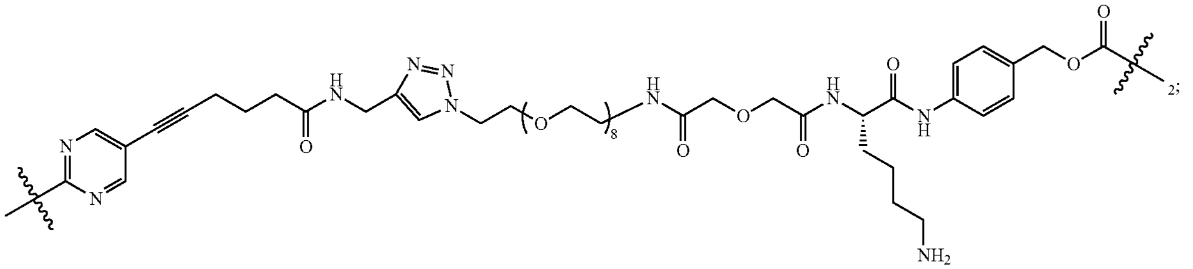;

wherein one of position 1 and position 2 represents a position at which the linker is attached to the antibody or antigen-binding fragment thereof of the present invention, and the other is a position at which the linker is attached to the therapeutic agent.

In some embodiments, the therapeutic agent and the linker are conjugated to form an intermediate prior to the conjugation of the antibody or antigen-binding fragment of the present invention. In some embodiments, the intermediate is linked by forming a thioether bond with a sulfhydryl group on the antibody or antigen-binding fragment of the present invention. The structure and preparation method of such intermediate and the method of using the same to prepare antibody conjugate are described, for example, in the international patent application publication No. WO2019/114666, and the relevant contents of which are incorporated herein by reference in their entirety.

In one embodiment, the antibody conjugate has the structure of Formula (I), $$A\text{-}(L\text{-}D)_{\gamma} \qquad (I)$$

wherein, A is the antibody or antigen-binding fragment thereof of the present invention;

L is a linker; preferably, L comprises an amino acid or a peptide consisting of 2-10 amino acids; further preferably, L is selected from Val, Cit, Phe, Lys, D-Val, Leu, Gly, Ala, Asn,

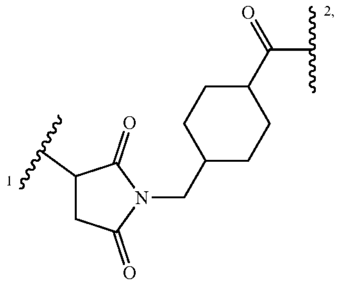
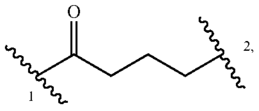
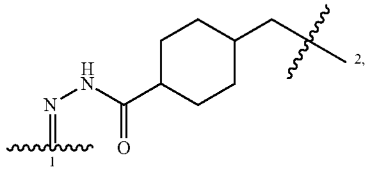
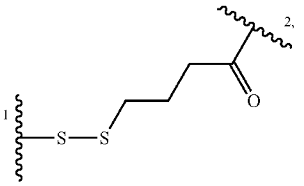
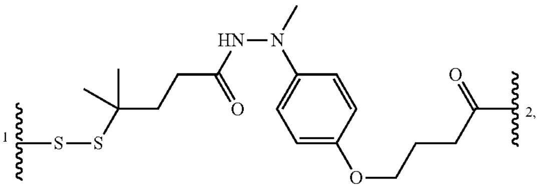
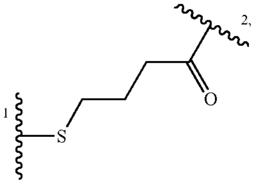
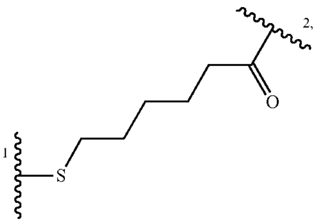
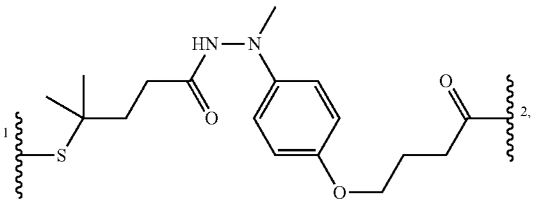
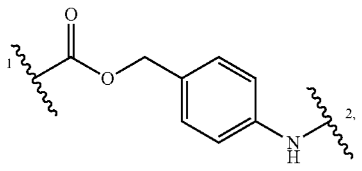
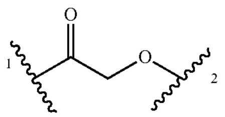
or
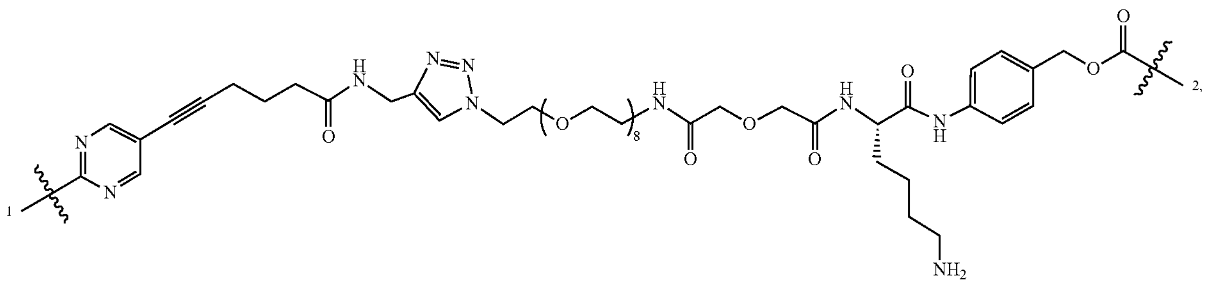
wherein one of position 1 and position 2 represents a position where L and A are connected, and the other represents a position where L and D are connected;
D is a therapeutic agent; preferably, D is selected from the group consisting of cytotoxic agents, therapeutic antibodies, radioisotopes, oligonucleotides and analogs thereof, biologically active peptides, protein toxins and enzymes; more preferably, D is an anti-tumor biologically active molecule; further preferably, D is

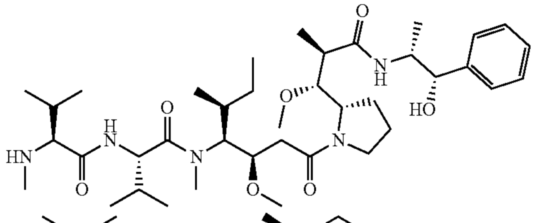

,

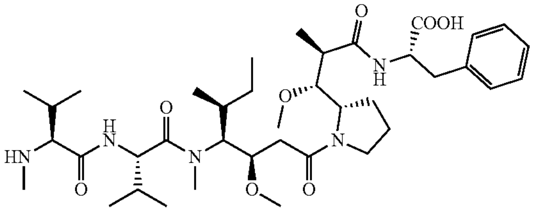

,

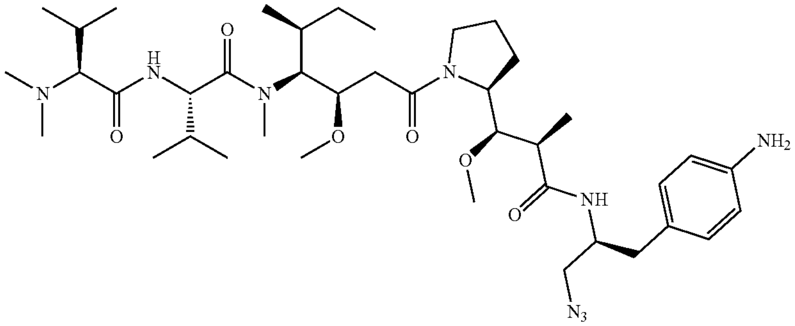

or

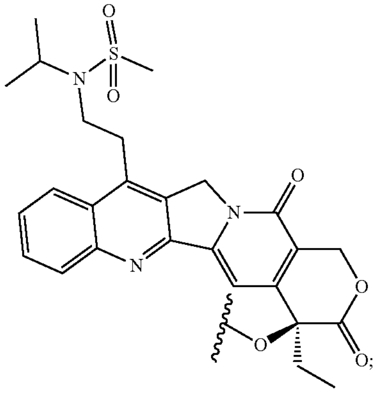

γ represents the number of (L-D) moieties linked to A, which is an integer from 1 to 10.

In a specific embodiment, the (L-D) moiety has the structure of Formula (1), which is linked by forming a thioether bond between the antibody or antigen-binding fragment thereof of the present invention and a sulfhydryl group on a compound of Formula (1), Formula (1)

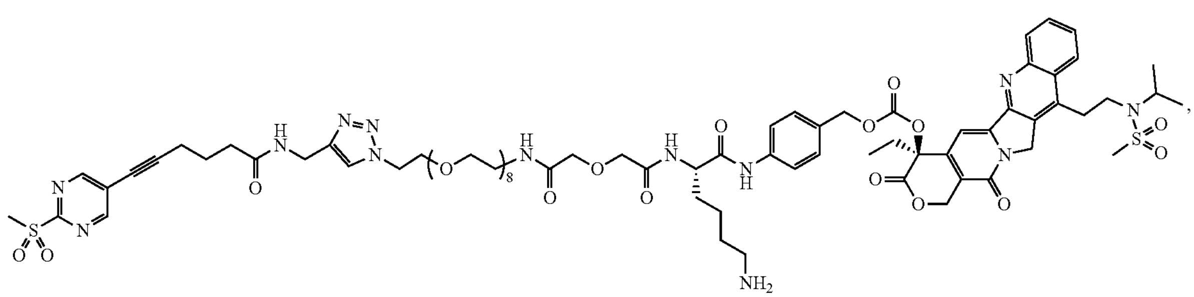

, and the antibody conjugate of the present invention has the structure of formula (2):

(2)

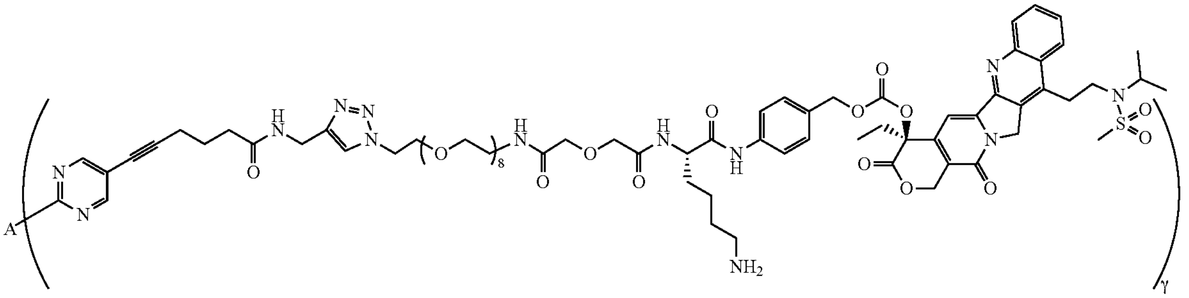

wherein A is the antibody or antigen-binding fragment of the present invention, and γ represents the number of (L-D) moieties linked to A by forming a thioether bond with the sulfhydryl group of A, which is an integer from 1 to 10. In a specific embodiment, A is an anti-human Nectin-4 humanized monoclonal antibody of the present invention.

In yet another aspect, the present invention provides a composition, which comprises the antibody conjugate of the present invention. In one embodiment, the molar ratio (DAR value) of the therapeutic agent to the anti-Nectin-4 antibody or antigen-binding fragment thereof of the present invention in the composition is a decimal or integer between 1 and 10, such as a decimal or integer between 1 and 8, such as 1.0, 1.5, 2.0, 2.5, 3.0, 3.1, 3.2, 3.3, 3.4, 3.5, 3.6, 3.7, 3.79, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 6.95, 7.0, 7.03, 7.1, 7.12, 7.2, 7.3, 7.4, 7.5, 7.6, 7.7, 7.8, 7.9 or 8.0.

CAR and CAR-Expressing Immune Effector Cell

The antibody or antigen-binding fragment thereof of the present invention can be used to construct a chimeric antigen receptor (CAR). Therefore, in another aspect, the present invention also provides a chimeric antigen receptor (CAR).

As used herein, the term "chimeric antigen receptor (CAR)" is an artificial receptor that specifically recognizes and binds to a target (e.g., an antigen expressed on the surface of a cancer cell), for example, by an antigen-binding fragment specifically binding to an antigen on the surface of a cancer cell, and that can confer target specificity to a cell (e.g., immune effector cell) that expresses the CAR on its surface. Preferably, the recognition of target by the CAR results in the activation and/or expansion of the CAR-expressing immune effector cell.

In some embodiments, the chimeric antigen receptor comprises the antibody or antigen-binding fragment thereof (e.g., scFv) of the present invention that specifically binds to Nectin-4, a transmembrane domain, and one or more intracellular T cell signal domains. In such embodiments, the present invention also provides a nucleic acid molecule, wherein the nucleic acid molecule may comprise a nucleotide sequence encoding a chimeric antigen receptor, the nucleotide sequence of the chimeric antigen receptor further comprises a nucleotide sequence encoding the antibody or antigen-binding fragment thereof (e.g., ScFv) of the present invention. In certain embodiments, the nucleic acid molecule of the present invention encodes a chimeric antigen receptor comprising an antigen-binding fragment (e.g., ScFv) of antibody of the present invention. The nucleic acid molecule can be isolated.

In yet another aspect, the present invention also provides an immune effector cell, which is genetically modified to express the CAR of the present invention on the surface. Preferably, the immune effector cell is selected from the group consisting of T lymphocytes (e.g., cytotoxic T cells (CTLs)), natural killer cells (NKs) and natural killer T cells (NKTs). The immune effector cell targets a Nectin-4-positive diseased cell (e.g., a Nectin-4-positive cancer cell) and is activated to initiate effector function, for example, causing the death of the Nectin-4-positive cancer cell.

In yet another aspect, the present invention also relates to a nucleic acid molecule encoding the CAR, an expression vector comprising the nucleic acid molecule, and an immune cell (e.g., CTL) expressing the CAR.

Pharmaceutical Composition

The present invention also provides a pharmaceutical composition, which comprises the antibody or antigen-binding fragment, antibody conjugate, composition, CAR-expressing immune effector cell, multispecific antibody or fusion protein of the present invention, and a pharmaceutically acceptable carrier and/excipient.

The pharmaceutical composition provided herein can be in a variety of dosage forms including, but not limited to, solid, semi-solid, liquid, powder, or lyophilized form.

Depending on the dosage form, the pharmaceutically acceptable carrier and/or excipient may include, but is not limited to, diluents, binders and adhesives, lubricants, disintegrants, preservatives, vehicles, dispersing agents, flow promoting agents, sweeteners, coatings, structure-forming excipients, preservatives, antioxidants (e.g., ascorbic acid, cysteine hydrochloride, sodium bisulfate, sodium metabisulfite, sodium sulfite, ascorbyl palmitate, butylated hydroxyanisole (BHA), butylated hydroxytoluene (BHT), lecithin, propyl gallate, α-tocopherol, citric acid, ethylenediaminetetraacetic acid (EDTA), sorbitol, tartaric acid, phosphoric acid, etc.), solubilizers, gelling agents, softeners, solvents (e.g., water, alcohol, acetic acid, and syrup), buffers (e.g., phosphate buffer, histidine buffer, and acetate buffer), surfactants (e.g., nonionic surfactant, such as polysorbate 80, polysorbate 20, poloxamer or polyethylene glycol), antibacterial agents, antifungal agents, isotonic agents (e.g., trehalose, sucrose, mannitol, sorbitol, lactose, glucose), absorption delaying agents, chelating agents and emulsifiers.

Preferably, the pharmaceutical composition is suitable for intravenous, intramuscular, subcutaneous, parenteral, spinal or epidermal administration (e.g., by injection or infusion). For compositions comprising antibody or antigen-binding fragment thereof or antibody conjugate, preferred dosage forms may generally be, for example, injectable solutions, lyophilized powders. For compositions comprising antibody or antigen-binding fragment thereof or antibody conjugate, suitable carrier and/or excipient may be selected from buffers (e.g., citrate buffer, acetate buffer, phosphate buffer, histidine buffer, histidine salt buffer), isotonic agents (e.g., trehalose, sucrose, mannitol, sorbitol, lactose, glucose), non-ionic surfactants (e.g. polysorbate 80, poly sorbate 20, poloxamer) or a combination thereof.

The pharmaceutical composition is generally sterile and stable under the conditions of manufacture and storage. By mixing the active substances (e.g., the antibody or antibody conjugate of the present invention) in the desired amount in a suitable solvent, and adding one or a combination of the above-listed carriers and/or excipients as needed, followed by sterile microfiltration, a sterile injectable solution can be prepared. Generally, the dispersion is prepared by incorporating the active substance into a sterile carrier and/or excipient containing a basic dispersion medium and the required other ingredients as listed above. In the case of sterile powder for the preparation of a sterile injectable solution, the preferred preparation method comprises vacuum drying and freeze-drying (lyophilization) a previously sterile-filtered solution thereof to obtain a powder of the active ingredient in combination with any desired additional ingredients.

The pharmaceutical composition provided herein can be administered to a subject by any method known in the art, for example, by systemic or topical administration. Routes of administration include, but are not limited to, parenteral (e.g., intravenous, intraperitoneal, intradermal, intramuscular, subcutaneous, or intracavitary), topical, epidural, or mucosal (e.g., intranasal, oral, vaginal, rectal, sublingual or local) administration. It will be understood by those of skill in the art that the exact dosage administered will depend on various factors, such as the metabolic properties of the pharmaceutical composition, the duration of treatment, the rate of excretion of the particular compound, the purpose of the treatment, the route of administration and the subject conditions, such as the patient's age, health, weight, gender, diet, medical history, and other factors well known in the medical arts. The method of administration can be, for example, injection or infusion.

As a general guide, the antibody conjugate of the present invention may be administered in a dosage range of about 0.0001 to 100 mg/kg, more typically 0.01 to 20 mg/kg body weight of subject. For example, the administration dosage can be 0.3 mg/kg body weight, 1 mg/kg body weight, 3 mg/kg body weight, 5 mg/kg body weight, 10 mg/kg body weight or 20 mg/kg body weight, or in the range of 1 to 20 mg/kg body weight. Exemplary treatment regimens required can be once per week, once every two weeks, once every three weeks, once every four weeks, once per month, once every 3 months, once every 3-6 months, or slightly shortened initial dosing interval and lengthened later dosing interval. The mode of administration can be intravenous drip.

Nectin-4 Related Disease

The antibody or antigen-binding fragment thereof, antibody conjugate, immune effector cell, multispecific antibody, fusion protein or pharmaceutical composition of the present invention, or the medicament prepared therefrom, can be used for the treatment and/or prevention of a disease. The disease is associated with Nectin-4. Preferably, the disease is associated with abnormal expression of Nectin-4. The term "abnormal expression" refers to an expression of a protein that is too high or too low in a sample, as compared to a sample in normal state (or a standard sample, for example, a sample from a subject not suffering from a disease associated with abnormal expression of Nectin-4).

Preferably, the disease is characterized by high expression of Nectin-4. For example, Nectin-4 is highly expressed in the tissue (e.g., bladder) of a subject with or suspected of having a disease (e.g., bladder cancer), while Nectin-4 is not expressed or at a low level in the tissue of a subject not has the disease.

Preferably, the disease is a cancer. Preferably, the cancer is selected from the group consisting of gastric cancer, liver cancer, hepatocellular carcinoma, bladder cancer, urothelial cancer, urethral cancer, renal pelvis cancer, ureteral cancer, lung cancer, non-small cell lung cancer, breast cancer, breast ductal cancer, triple-negative breast cancer, pancreatic cancer, ovarian cancer, head and neck cancer, colon cancer, rectal cancer and esophageal cancer.

Cancer therapy can be assessed by, for example, but not limited to, the degree of tumor regression, changes in tumor weight or size, progression time, survival time, progression-free survival, overall response rate, duration of response, quality of life, protein expression and/or activity, etc.

Use for Diagnosis and Treatment

The anti-Nectin-4 antibody or antigen-binding fragment thereof or antibody conjugate of the present invention can be used for diagnostic purposes to detect, diagnose or monitor a disease and/or disorder associated with Nectin-4. For example, the anti-Nectin-4 antibody or antigen-binding fragment thereof or antibody conjugate provided herein can be used in in situ, in vivo, ex vivo and in vitro diagnostic assay or imaging assay.

In some embodiments, to detect the expression level of Nectin-4 in a subject and/or to track a Nectin-4 expressing cell, the antibody or antigen-binding fragment of the present invention can be conjugated to at least one label to obtain a labeled antibody. Such labeled antibody is also encompassed within the scope of the antibody or antigen-binding fragment of the present invention. Preferably, the label is selected from the group consisting of enzyme (e.g., horseradish peroxidase), fluorescent dye, radioisotope, biotin and colloidal gold. Techniques for conjugating label to antibody are well known to those skilled in the art.

In one aspect, the present invention provides a method of detecting the presence or determining the expression level of Nectin-4 in a sample, comprising:

(a) contacting the sample with the antibody or antigen-binding fragment or labeled antibody of the present invention;
(b) detecting the formation or determining the amount of an immune complex of the antibody or antigen-binding fragment and Nectin-4 in the sample, so as to detect the presence or determine the expression of Nectin-4 in the sample.

The present invention also provides a method of diagnosing a disease related to Nectin-4 in a subject, comprising:

(a) obtaining a sample of the subject;
(b) using the antibody or antigen-binding fragment or labeled antibody of the present invention to detect the expression level of Nectin-4 in the sample;
(c) comparing the expression level of Nectin-4 with the expression level of a reference protein, wherein the increase or decrease of the expression level of Nectin-4 compared with the expression level of the reference protein indicates abnormal expression of Nectin-4.

The reference protein can be Nectin-4 in a standard sample, and the standard sample can be, for example, a sample from a subject not suffering from a disease associated with abnormal expression of Nectin-4. The sample can be in any form, such as cell, tissue, body fluid. The above detection can be performed using techniques known in the art, including, but not limited to, Western blotting, flow cytometry, immunohistochemical assay (IHC), ELISA assay.

The present invention also relates to a use of the antibody or antigen-binding fragment thereof, antibody conjugate, immune effector cell, multispecific antibody, fusion protein or pharmaceutical composition of the present invention in the treatment and/or prevention of a disease.

The present invention also relates to a use of the antibody or antigen-binding fragment thereof, antibody conjugate, immune effector cell, multispecific antibody, fusion protein or pharmaceutical composition of the present invention in the manufacture of a medicament, wherein the medicament is used for the treatment and/or prevention of a disease. In one embodiment, the disease is a cancer as described herein.

The antibody or antigen-binding fragment thereof, antibody conjugate, immune effector cell, multispecific antibody, fusion protein or pharmaceutical composition of the present invention can be administered in combination with at least one or more of the therapeutic agents described herein.

The mode of combined administration is not limited. For example, the above therapeutic agents can be administered all at one time or separately. When administered separately (in the case of mutually different administration regimens), they may be administered continuously without interruption or at a predetermined interval.

Treatment Method

The present invention also provides a method of treating a disease associated with Nectin-4 in a subject in need thereof. In one embodiment, the disease is a cancer as described herein.

The method comprises administering to the subject a therapeutically effective amount of the antibody or antigen-binding fragment thereof, antibody conjugate, composition, immune effector cell, multispecific antibody, fusion protein or pharmaceutical composition of the present invention.

In certain embodiments, the method of the present invention further comprises administering a treatment regimen selected from the group consisting of: surgery, radiotherapy, chemotherapy, targeted therapy, immunotherapy, hormone therapy, angiogenesis inhibition, and palliative care.

In certain embodiments, the method of the present invention further comprises administering one or more therapeutic agents selected from the group consisting of: chemotherapeutic agents, radioisotopes, immune checkpoint inhibitors, antibody targeting other antigens, and other anti-tumor drugs. The chemotherapeutic agents may include, for example, antimetabolites, alkylating agents, cytotoxic agents, topoisomerase inhibitors, microtubule inhibitors. The other anti-tumor drugs may include, for example: angiogenesis inhibitors, deacetylase (HDAC) inhibitors, Hedgehog signaling pathway blockers, mTOR inhibitors, p53/mdm2 inhibitors, PARP inhibitors, proteasome inhibitors (e.g., bortezomib, carfilzomib, ixazomib, Marizomib, Oprozomib) and tyrosine kinase inhibitors (e.g., BTK inhibitor). Examples of the chemotherapeutic agents include, but are not limited to: cyclophosphamide, ifosfamide, melphalan, busulfan, chlormethine, chlorambucil, Lomustine, carmustine (BCNU), CCNU, cisplatin (DDP), carboplatin (CBP), oxaliplatin (OXA), methotrexate (MTX), 6-mercaptopurine (6-MP), 5-fluorouracil (5-FU), cytarabine, gemcitabine, vinblastine, vincristine, vindesine, camptothecin, irinotecan, topotecan, rubitecan, etoposide, teniposide, paclitaxel, taxane, docetaxel, paclitaxel liposome, actinomycin D, idarubicin, doxorubicin, epirubicin, mitomycin, bleomycin, doxorubicin, epirubicin. The immune checkpoint inhibitors includes, but are not limited to, antibodies or antigen-binding fragments thereof that specifically binds to PD-1, PD-L1, CTLA4, LAG-3, TIM-3 or VISTA. The radioisotopes can include, for example, $^{212}$Bi, $^{213}$Bi, $^{131}$I, $^{125}$I, $^{111}$In, $^{177}$Lu, $^{186}$Re, $^{188}$Re, $^{153}$Sm, $^{90}$Y.

In some embodiments, the antibody or antigen-binding fragment thereof, antibody conjugate, immune effector cell, multispecific antibody, fusion protein or pharmaceutical composition of the present invention is used in combination with a chemotherapeutic agent. In one embodiment, the chemotherapeutic agent is selected from the group consisting of: cisplatin, oxaliplatin, gemcitabine, cyclophosphamide, 5-fluorouracil, and combinations thereof. In other embodiments, the antibody conjugate of the present invention is used in combination with an immune checkpoint inhibitor. In one embodiment, the immune checkpoint inhibitor is selected from the group consisting of anti-PD-L1 antibody or antigen-binding fragment thereof, anti-PD-1 antibody or antigen-binding fragment thereof, and combination thereof. In yet other embodiments, the antibody or antigen-binding fragment thereof, antibody conjugate, immune effector cell, multispecific antibody, fusion protein or pharmaceutical composition of the present invention is used in combination with a radioisotope.

Kit

The present invention also provides a kit, which comprises the antibody or antigen-binding fragment, antibody conjugate, labeled antibody, multispecific antibody, fusion protein, pharmaceutical composition or immune effector cell of the present invention, and an instruction for use. The kit may also comprise a suitable container. In certain embodiments, the kit further comprises a device for administration. Typically, the kit also comprises a label, which is used for indicating the intended use and/or method of use of the content in the kit. The term "label" intends to comprise any written or recorded material on or with the kit or otherwise provided with the kit.

Beneficial Effect

In a specific aspect, the present invention provides an anti-Nectin-4 antibody or antigen-binding fragment thereof, particularly an anti-Nectin-4 humanized monoclonal antibody. The antibody of the present invention has a high affinity for Nectin-4: in the Examples, various methods such as ELISA, biofilm interference technology and flow cytometry are used to detect the binding affinity of the antibody of the present invention to Nectin-4, and the results show that the anti-Nectin-4 antibody of the present invention has high affinity for both in vitro purified Nectin-4 and cell surface Nectin-4. Surprisingly, the dynamic affinities of the humanized monoclonal antibodies 31 HZ, 56 HZ and 74 HZ to human Nectin-4 and cynomolgus monkey Nectin-4 are all better than those of the prior art Enfortumab, indicating that the antibody of the present invention has higher affinity to Nectin-4 in terms of in vivo binding activity; and this is also confirmed by the higher endocytic activity of antibodies 31

HZ, 56 HZ and 74 HZ. Furthermore, the antibody of the present invention has high specificity for Nectin-4: 31 HZ, 56 HZ and 74 HZ all specifically recognize human Nectin-4, but do not recognize Nectin-1, Nectin-2 and Nectin-3. In addition, the antibody of the present invention blocks the binding of Nectin-4 to Nectin-1, and the competitive binding ability of 31 HZ, 56 HZ and 74 HZ to Nectin-4 is comparable to that of Enfortumab.

In another specific aspect, the present invention also provides an anti-Nectin-4 antibody conjugate that can target a Nectin-4 positive cell. The antibody conjugate of the present invention can target a Nectin-4 positive cell with high affinity and high specificity, which is very beneficial for the treatment of a cancer or in vivo diagnosis, because the high affinity and specificity can reduce off-target toxic effects and reduce side effects. The Examples also confirm this point. The ADC of the present invention has strong killing activity against various tumor cell lines such as human breast ductal cancer cells, human gastric cancer cells and human breast cancer cells that endogenously express human Nectin-4. Furthermore, in the mouse non-small cell lung cancer xenograft model, the ADC of the present invention exhibits significant tumor inhibitory activity and has good safety.

EXAMPLES

The following examples are intended to be illustrative of the present invention only, and therefore should not be construed as limiting the present invention in any way. In the following examples, the experimental methods without specific conditions were carried out according to conventional methods and conditions, or according to product instructions.

Example 1: Preparation of Anti-Human Nectin-4 Humanized Monoclonal Antibody 1.1 Construction of Human Nectin-4 Overexpressing Cell Line In order to verify the specificity and function of human Nectin-4 antibodies, the complete coding sequence of human Nectin-4 (Uniprot ID: Q96NY8-1) (synthesized by Nanjing GenScript Biotechnology Co., Ltd.) was cloned into lentiviral vector pLVX-IRES-puro, and the virus was prepared by the lentiviral packaging system described in the literature (Mohammadi Z et al., Mol Biotechnol. 2015 September; 57(9): 793-800), and the obtained virus was used to infect A549 non-small cell lung cancer cells (ATCC) and T24 human bladder transitional cell carcinoma cells (ATCC), respectively, and by puromycin screening and monoclonal selection, the monoclonal A549-Nectin-4 stable cell line and T24-Nectin-4 stable cell line overexpressing human Nectin-4 were obtained.

1.2 Detection of Human Nectin-4 Overexpressing Cell Lines

Figure 1A:
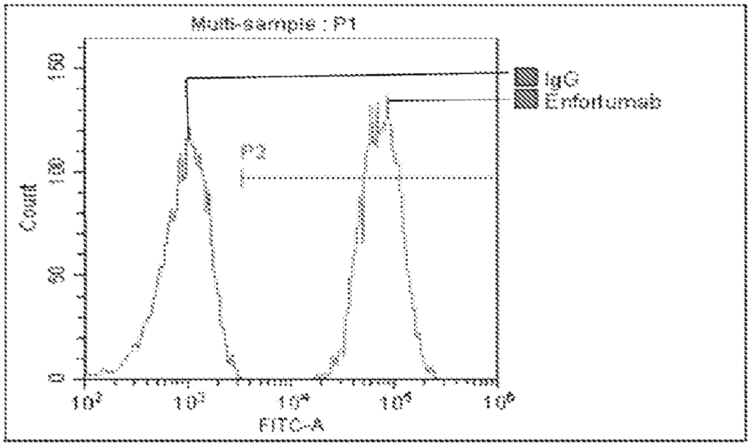
FIG. 1A shows the results of flow cytometry of A549-Nectin-4 stable cell line.
Figure 1B:
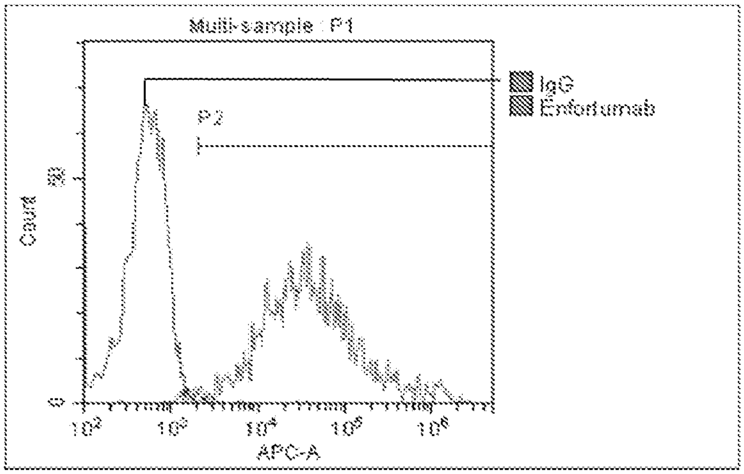
FIG. 1B shows the results of flow cytometry of T24-Nectin-4 stable cell line.

The A549-Nectin-4 and T24-Nectin-4 stable cell lines were identified by flow cytometry (flow cytometer: Beckman, CytoFlex; detection antibody Enfortumab, with sequence indicated in the international patent application publication No.: WO2012/047724), and it was confirmed that the cells correctly expressed human Nectin-4. As shown in FIGS. 1A and 1B, the flow cytometry results showed that both A549-Nectin-4 and T24-Nectin-4 had high positive rates (close to 100%), indicating that both A549-Nectin-4 and T24-Nectin-4 were well-homogenous stable cell lines that could be used for subsequent experiments.

1.3 Preparation of Anti-Human Nectin-4 Murine Monoclonal Antibody

Wild-type mice were immunized by protein immunization to obtain anti-human Nectin-4 murine monoclonal antibody. Complete Freund's adjuvant (CFA) emulsified human Nectin-4 protein (Sino Biological, Cat: 19771-H08H) was used to immunize 2 Babl/c and 2 C57 mice, 5-6 weeks old each. Specifically, 50 μg of the protein was used to perform subcutaneous primary immunization, then 25 μg of incomplete Freund's adjuvant (IFA) emulsified Nectin-4 protein was used to perform intraperitoneal booster immunization every 2 weeks, after 3 times of booster, Nectin-4-endogenously expressing tumor cell T47D $5\times10^6$ cells (a kind of human breast duct cancer cell) was used to perform the final intraperitoneal booster, and 3-5 days later, spleen cells were taken to perform hybridoma fusion. The mouse spleen cells were fused with Sp2/0 (ATCC, Cat #CRL-1581) mouse myeloma cell line by PEG using standard fusion procedures, then HAT was used to perform pressurization screening, and after 10-14 days, ELISA screening was performed, and about 200 positive clones that bound to Nectin-4 protein were obtained. Through further screening by flow cytometry, 3 positive hybridoma clones that could recognize T47D tumor cells were obtained for subcloning, and finally subclonal sorting was performed by limiting dilution method to obtain monoclones, and their numbers were: 31 #, 56 # and 74 #, respectively.

1.4 Affinity Detection of Anti-Human Nectin-4 Mouse Antibody

The affinity of candidate molecules to human Nectin-4 was detected by ELISA method. The hybridoma monoclones 31 #, 56 # and 74 # were cultured without serum to obtain 3-10 mL of supernatants, and then purified by Protein A (MabSelect SuRe, GE) to obtain murine antibodies.

The affinity of the murine monoclonal antibodies isolated and purified from the culture supernatants of the hybridoma cell lines 31 #, 56 # and 74 # was determined by ELISA. Human Nectin-4 (Sino Biological, Cat: 19771-H08H) was diluted to 1 μg/mL with carbonate (CBS) buffer, added to a 96-well plate at a volume of 100 μL/well, and placed at 4° C. for 16-20 h. The CBS buffer in the 96-well plate was discarded by pipetting, the plate was washed once with PBST (pH 7.4, PBS containing 0.05% Tween 20) buffer, added with 200 μL/well of skim milk powder (blocking solution) containing 2% PBST, incubated for 1 h at room temperature for blocking. The blocking solution was removed, and the plate was washed three times with PBST buffer. The anti-Nectin-4 mouse antibody to be tested was diluted with PBST/2% skim milk powder to an appropriate concentration, then added to the plate at a volume of 100 μL/well, and incubated at room temperature for 1.5 h. The reaction system was removed, and the plate was washed three times with PBST, and 50 μL/well of HRP-labeled goat anti-mouse IgG secondary antibody (purchased from the Jackson Laboratory) diluted with PBST/1% skim milk powder (dilution ratio 1:5000) was added, and incubated at room temperature for 1 h. After the plate was washed 3 times with PBST, 100 μL/well of TMB was added, and incubated at room temperature for 5-10 min for color development. The color development was stopped by adding 50 μL/well of 0.2 M sulfuric acid. Microplate reader was used to detect optical density (O.D.) at dual wavelengths 450/620 nm.

Figure 2:
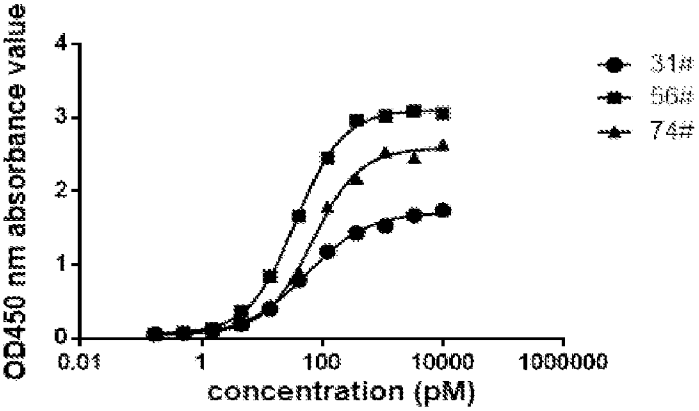
FIG. 2 shows the results of affinity detection of anti-human Nectin-4 murine antibody.
Figure 3A:
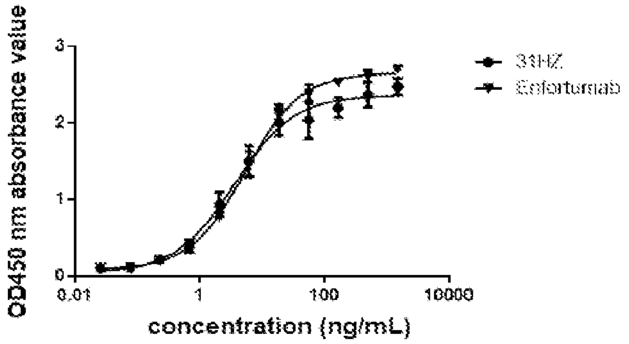
FIG. 3A shows the results of ELISA detection for the affinity between anti-human Nectin-4 humanized monoclonal antibody 31 HZ and human Nectin-4 protein.
Figure 3B:
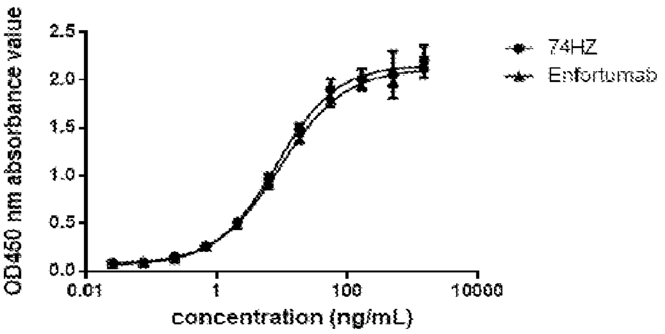
FIG. 3B shows the results of ELISA detection for the affinity between anti-human Nectin-4 humanized monoclonal antibody 74 HZ and human Nectin-4 protein.
Figure 3C:
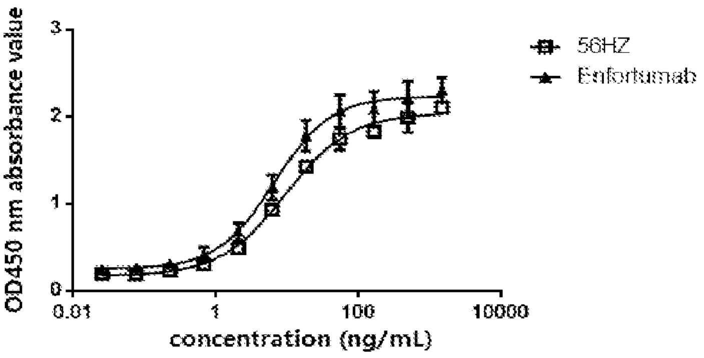
FIG. 3C shows the results of ELISA detection for the affinity between anti-human Nectin-4 humanized monoclonal antibody 56 HZ and human Nectin-4 protein.
Figure 3D:
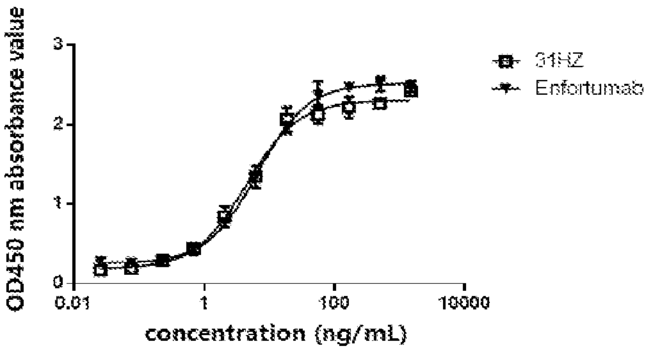
FIG. 3D shows the results of ELISA detection for the affinity between anti-human Nectin-4 humanized monoclonal antibody 31 HZ and cynomolgus monkey Nectin-4 protein.
Figure 3E:
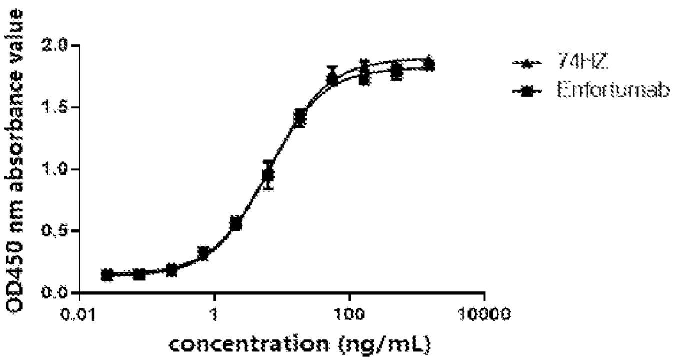
FIG. 3E shows the results of ELISA detection for the affinity between anti-human Nectin-4 humanized monoclonal antibody 74 HZ and cynomolgus monkey Nectin-4 protein.
Figure 3F:
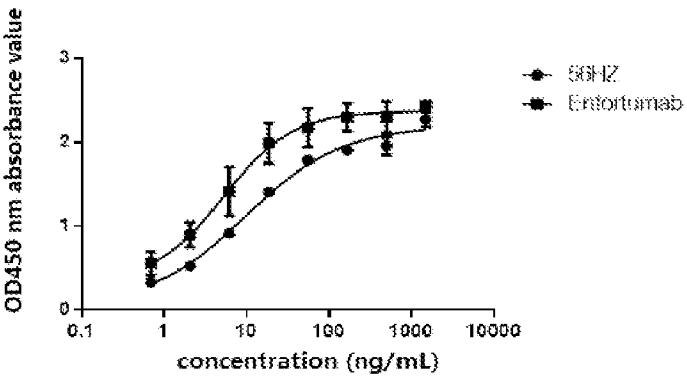
FIG. 3F shows the results of ELISA detection for the affinity between anti-human Nectin-4 humanized monoclonal antibody 56 HZ and cynomolgus monkey Nectin-4 protein.

The detection results were shown in FIG. 2 and Table 3. All 3 anti-human Nectin-4 murine antibodies were able to bind human Nectin-4 protein with high affinity, with $EC_{50}$ ranging from 30 to 70 pM.

TABLE 3

Anti-human Nectin-4 affinity detection

| Clone No. | $EC_{50}$ (pM) |
|---|---|
| 31# | 54.95 |
| 56# | 36.33 |
| 74# | 69.39 |

1.5 Amplification of Variable Region of the Anti-Nectin-4 Murine Monoclonal Antibodies The hybridoma cells were cultured to about 8,000-10,000 cells, then the cells were lysed and the first-strand cDNA was synthesized using a cDNA reverse transcription kit (Thermo Fisher Sci. Cat #18080-200). The VH and VK genes were amplified by PCR from cDNA using primers, and the PCR products were purified by DNA purification kit (Qiagen, Cat #28104) and ligated to PUC57 vector. Approximately 5 clones were picked for each ligation reaction and sequenced. Sequences were analyzed by Vector NTI 11.5 (Thermo Fisher Sci.) and Sequencer 5.4.6 (Genecodes). The variable region sequences and CDR sequences of the anti-human Nectin-4 murine antibodies were obtained by IMGT and abYsis and shown in Table 4 below.

TABLE 4

| Amino acid sequences of variable regions and CDRs of anti-human Nectin-4 murine antibodies | | | | | | | | | |
|---|---|---|---|---|---|---|---|---|---|
| Clone No. | VH | VL | Numbering system | CDR-H1 | CDR-H2 | CDR-H3 | CDR-L1 | CDR-L2 | CDR-L3 |
| 31# | 1 | 2 | Chothia | 3 | 4 | 5 | 6 | 7 | 8 |
| | | | Abm | 9 | 10 | 5 | 6 | 7 | 8 |
| | | | Kabat | 11 | 12 | 5 | 6 | 7 | 8 |
| | | | IMGT | 13 | 14 | 15 | 16 | 17 | 8 |
| 56# | 19 | 20 | Chothia | 21 | 22 | 23 | 24 | 25 | 26 |
| | | | Abm | 27 | 28 | 23 | 24 | 25 | 26 |
| | | | Kabat | 29 | 30 | 23 | 24 | 25 | 26 |
| | | | IMGT | 31 | 32 | 33 | 34 | 35 | 26 |
| 74# | 37 | 38 | Chothia | 39 | 40 | 41 | 42 | 43 | 8 |
| | | | Abm | 45 | 46 | 41 | 42 | 43 | 8 |
| | | | Kabat | 47 | 48 | 41 | 42 | 43 | 8 |
| | | | IMGT | 49 | 50 | 51 | 52 | 53 | 8 |

Note:
The numbers in the columns of VH, VL, CDR-H1, CDRH2, CDR-H3, CDR-L1, CDR-L2 and CDR-L3 represent their corresponding SEQ ID NOs, for example, for the antibody 31#, its VH corresponds to SEQ ID NO: 1, and its VL corresponds to SEQ ID NO: 2.

1.6 Humanization of Anti-Human Nectin-4 Murine Antibody

The murine antibodies 31 #, 56 #, and 74 # were humanized by the CDR-grafting. In short, the humanization comprised the following steps: the amino acid sequence of the murine monoclonal antibody was aligned with the amino acid sequence of human germline antibody to find sequences with high homology and better physicochemical properties as human germline framework sequences; HLA-DR affinity was analyzed and investigated, and human germline framework sequences with low affinity were selected; and then the six CDRs of the murine antibodies were transplanted to the selected heavy chain and light chain framework sequences, respectively.

Furthermore, a computer simulation technology was used, and molecular docking was used to analyze the framework amino acid sequences of the variable region and surrounding regions thereof, and the spatial three-dimensional binding mode thereof was investigated. By calculating electrostatic force, van der Waals force, hydrophilicity and hydrophobicity, and entropy value, the key amino acids in the murine antibody amino acid sequences that could interact with Nectin-4 protein and maintain the spatial framework were analyzed, and these murine amino acids were retained in the transplanted antibody. That was, a series of back-mutations were performed on the amino acid residues in the FR region of the humanized template, so as to retain the antigen-binding ability of the murine antibody in the humanized antibody as much as possible.

According to the above method, the humanized antibodies were constructed based on the CDRs of the murine antibodies 31 #, 56 # and 74 #, which were named as 31 HZ, 56 HZ and 74 HZ, respectively; wherein, the heavy chain constant regions of each antibody were human IgG1 heavy chain constant region (SEQ ID NO: 61), the light chain constant regions of each antibody were human κ light chain constant region (SEQ ID NO: 62). The light chain CDR amino acid sequences of the constructed humanized antibodies 31 HZ, 56 HZ and 74 HZ were identical to the light chain CDRs of 31 #, 56 # and 74 #, respectively. The amino acid sequences of the heavy chain CDRs of the constructed humanized antibodies 31 HZ, 56 HZ and 74 HZ were shown in Table 5.1:

TABLE 5.1

| Amino acid sequences of heavy chain CDRs of anti-human Nectin-4 humanized antibodies | | | | |
|---|---|---|---|---|
| CDRH group | Numbering system | CDR-H1 (SEQ ID NO:) | CDR-H2 (SEQ ID NO:) | CDR-H3 (SEQ ID NO:) |
| 56HZ CDRH-a | Chothia | GYFNSITSDY (18) | SFSGR (22) | GNYDGFDY (23) |
| 56HZ CDRH-b | Abm | GYFNSITSDYDWH (36) | YISFSGRTY (28) | |
| 56HZ CDRH-c | Kabat | ITSDYDWH (44) | YISFSGRTYYNPS LKS (30) | |
| 56HZ CDRH-d | IMGT | GYFNSITSDYD (54) | ISFSGRT (32) | ARGNYDGFDY (33) |
| 31HZ CDRH-a | Chothia | GYTFTDY (3) | HPSDSE (4) | WDFRIYYAMD Y (5) |
| 31HZ CDRH-b | Abm | GYTFTDYWMN (9) | MIHPSDSETR (10) | |
| 31HZ CDRH-c | Kabat | DYWMN (11) | MIHPSDSETRLN QKFQG (63) | |

TABLE 5.1-continued

| Amino acid sequences of heavy chain CDRs of anti-human Nectin-4 humanized antibodies | | | | |
|---|---|---|---|---|
| CDRH group | Numbering system | CDR-H1 (SEQ ID NO:) | CDR-H2 (SEQ ID NO:) | CDR-H3 (SEQ ID NO:) |
| 31HZ CDRH-d | IMGT | GYTFTDYW (13) | IHPSDSET (14) | ARWDFRIYYA MDY (15) |
| 74HZ CDRH-a | Chothia | GYTFINY (39) | HPSDSA (40) | |
| 74HZ CDRH-b | Abm | GYTFINYWMN (45) | MIHPSDSATR (46) | WGNFYTVNAW YYFDY (41) |
| 74HZ CDRH-c | Kabat | NYWMN (47) | MIHPSDSATRLN QSFQG(64) | |
| 74HZ CDRH-d | IMGT | GYTFINYW (49) | IHPSDSAT (50) | ARWGNFYTVN AWYYFDY (51) |

Furthermore, the amino acid sequences of the variable and constant regions of the humanized antibodies 31 HZ, 56 HZ and 74 HZ were shown in Table 5.2:

TABLE 5.2

| Amino acid sequences of variable and constant regions of anti-human Nectin-4 humanized antibodies | | | | |
|---|---|---|---|---|
| Antibody name | Heavy chain variable region (SEQ ID NO:) | Light chain variable region (SEQ ID NO:) | Heavy chain constant region (SEQ ID NO:) | Light chain constant region (SEQ ID NO:) |
| 31HZ | 55 | 56 | 61 | 62 |
| 56HZ | 57 | 58 | | |
| 74HZ | 59 | 60 | | |

1.7 Preparation of Anti-Human Nectin-4 Humanized Antibodies

The heavy chain and light chain amino acid sequences of the above anti-human Nectin-4 humanized antibodies were synthesized by codon optimization and ligated into plasmid ptt5 (entrusted to Nanjing GenScript Biotechnology Co., Ltd.). The plasmids corresponding to the heavy and light chains were simultaneously transfected into CHO-E cells, and the supernatants were purified by protein A (MabSelect SuRe, GE) to obtain anti-human Nectin-4 humanized antibodies.

Example 2: Detection of Affinity of Anti-Human Nectin-4 Humanized Monoclonal Antibodies 2.1 Detection of Affinity of Anti-Human Nectin-4 Humanized Monoclonal Antibodies to Nectin-4 Protein of Different Species The affinity of anti-human Nectin-4 humanized monoclonal antibodies to Nectin-4 protein of different species was detected by ELISA. The specific steps were as follows: human Nectin-4 or cynomolgus monkey Nectin-4 antigen was diluted to 1 μg/mL with CBS coating solution (0.32 g $Na_2CO_3$ and 0.59 g $NaHCO_3$ were weighed, dissolved in deionized water, and made up to 200 mL), and was coated on an ELISA plate with 100 μL per well, and standed overnight at 4° C.; the liquid in the well was discarded on the next day, washed once with 300 μL of PBS; 100 μL of PBS (containing 2% BSA, purchased from BOVOGEN, Cat. No. BSAS 1.0) was added, blocked for 2 hours at 37° C.; the 31 HZ, 56 HZ, 74 HZ and Enfortumab antibody were diluted (starting at 1500 ng/mL, 3-fold dilution, 11 concentration points) with PBS (containing 2% BSA), and 100 μL was taken and added to the corresponding well, incubated at 37° C. for 2 hours; washed 3 times with 300 μL of PBST; HRP-labeled goat anti-human secondary antibody (purchased from Jackson, 109-035-00) was diluted at 1:10000 with PBS (containing 2% BSA), 100 μL was taken and added to the corresponding well, incubated at 37° C. for 1 hour; washed 5 times with 300 μL of PBST; 100 μL of TMB color development solution (purchased from InnoReagents, TMB-S-004) was added to the corresponding well, color development was performed at room temperature for 5-20 minutes; 50 μL of 2N $H_2SO_4$ was added for stopping, OD450 nm readings were collected on a microplate reader (purchased from MD, SpectraMax M2) and imported into Graphpad Prism for curve fitting.

The experimental results were shown in FIGS. 3A to 3F and Table 6, indicating that the affinity of 31 HZ to human Nectin-4 protein and cynomolgus monkey Nectin-4 protein was better than that of Enfortumab; and the affinity of 56 HZ and 74 HZ to human Nectin-4 protein and cynomolgus monkey Nectin-4 protein was basically comparable to that of Enfortumab.

TABLE 6

| Detection of affinity of anti-human Nectin-4 humanized monoclonal antibodies to Nectin-4 protein of different species | | |
|---|---|---|
| | $EC_{50}$ (ng/mL) | |
| Antibody name | Human Nectin-4 protein | Cynomolgus monkey Nectin-4 protein |
| 31HZ | 3.60 | 4.45 |
| 56HZ | 9.48 | 9.85 |
| 74HZ | 8.34 | 6.73 |
| Enfortumab | 7.10 ± 2.00 (n = 3) | 6.00 ± 0.66 (n = 3) |

2.2 Detection of Dynamic Affinity of Anti-Human Nectin-4 Humanized Monoclonal Antibodies to Nectin-4 Protein of Different Species The dynamic affinity of anti-human Nectin-4 humanized monoclonal antibodies was detected using Octet Fortebio®. The main steps comprised: firstly, the anti-human Nectin-4 humanized monoclonal antibody (concentration of 5 μg/mL) was immobilized on ProA sensor, then subjected to binding reaction with human or cynomolgus monkey Nectin-4 (gradiently diluted to 400 nM, 200 nM, 100 nM, 50 nM, 25 nM, 12.5 nM, 6.25 nM, 0 nM), and the anchored product in the solid phase obtained through fully reaction was subjected to dissociation reaction in PBST buffer. After the completion of the experiment, the results were analyzed by using Data Analysis 11.0 software at 1:1 mode to perform global fitting, thereby obtaining the affinity constant of antibody to antigen.

The experimental results were shown in Table 7. The dynamic affinity of 31 HZ, 56 HZ and 74 HZ to human Nectin-4 protein and cynomolgus monkey Nectin-4 protein was better than that of Enfortumab.

TABLE 7

Detection of dynamic affinity of anti-human Nectin-4 humanized monoclonal antibody to Nectin-4 protein of different species

| Antibody name | $K_D$ ($\times 10^{-9}$ M) Human Nectin-4 protein | Cynomolgus monkey Nectin-4 protein |
|---|---|---|
| 31HZ | 22.50 | 14.50 |
| 56HZ | 19.60 | 18.40 |
| 74HZ | 12.10 | 9.540 |
| Enfortumab | 28.30 ± 2.90 (n = 2) | 33.60 ± 3.50 (n = 2) |

2.3 Detection of Affinity of Anti-Human Nectin-4 Humanized Monoclonal Antibody to Human Nectin-4 on Tumor Cell Membrane Surface T47D cells were used to detect the affinity of 31 HZ and 74 HZ to human Nectin-4 on cell membrane surface. The specific steps were as follows: T47D cells were digested, resuspended by centrifugation, and washed twice with PBS; the cells were resuspended in PBS (containing 1% BSA), and spread into a 96-well tip-bottom plate at $3\times10^5$ cells/well, with a volume of 50 μl per well; 50 μL of the antibody to be tested was added to each well, starting at a final concentration of g/mL, 4-fold gradient dilution, a total of 10 concentration points; Human IgG was used as a negative control; after being mixed well, the resulting mixture was reacted in the dark at 4° C. for 1 hour; washing was performed 3 times with PBS, FITC-labeled anti-human Fc secondary antibody (brand: BioLegend, product number: 409322) was added, incubated at 4° C. for 0.5 hours in the dark; washing was performed 3 times with PBS, and detection was carried out using a flow cytometer (flow cytometer brand: Beckman, model: Cytoflex).

The same method was used to detect the affinity of 56 HZ to human Nectin-4 on NCI-N87 cell (a kind of human gastric cancer cell, ATCC) membrane surface. The antibody was started at 3.33 μg/mL, 3-fold dilution, a total of 10 concentration points.

Figure 4A:
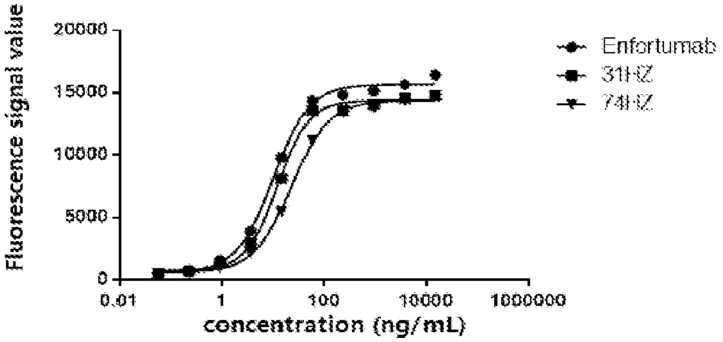
FIG. 4A shows the results of flow cytometry for the affinity of anti-human Nectin-4 humanized monoclonal antibodies 31 HZ, 74 HZ to T47D cells.
Figure 4B:
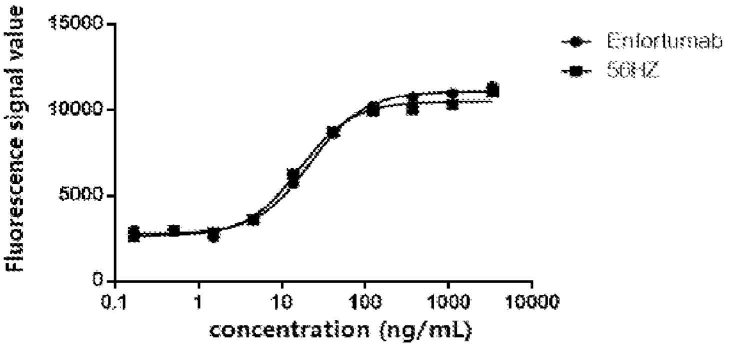
FIG. 4B shows the results of flow cytometry for the affinity between anti-human Nectin-4 humanized monoclonal antibody 56 HZ to NCI-N87 cells.
Figure 5A:
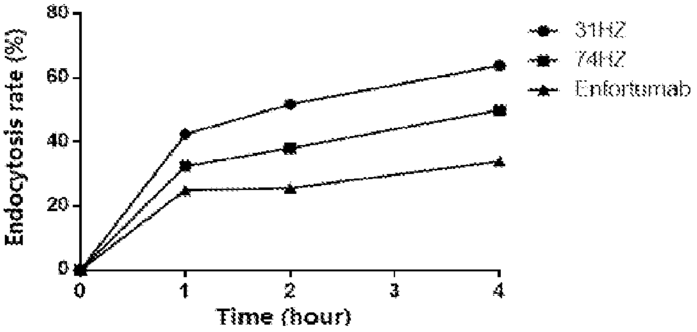
FIG. 5A shows the detection results of endocytosis activity of anti-human Nectin-4 humanized monoclonal antibody 31 HZ and 74 HZ on T47D cells.
Figure 5B:
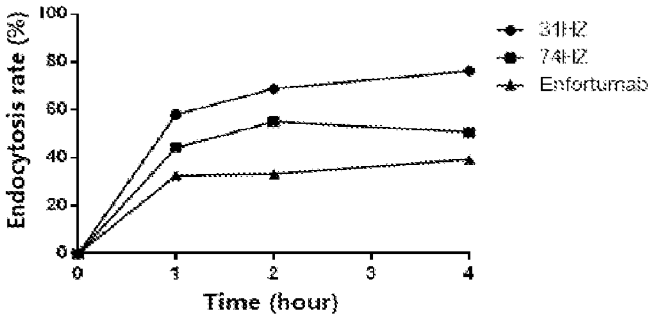
FIG. 5B shows the detection results of endocytosis activity of anti-human Nectin-4 humanized monoclonal antibody 31 HZ and 74 HZ on MDA-MB-468 cells.
Figure 5C:
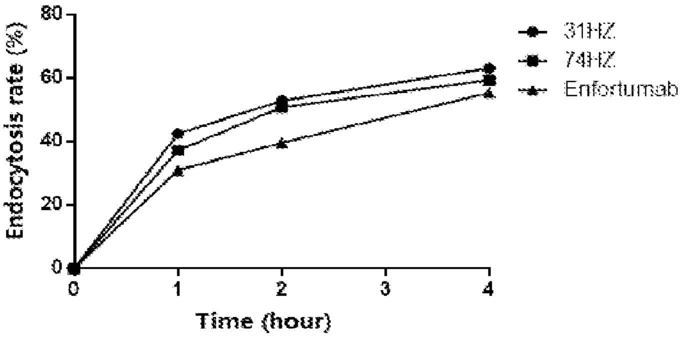
FIG. 5C shows the detection results of endocytosis activity of anti-human Nectin-4 humanized monoclonal antibody 31 HZ and 74 HZ on A549-Nectin-4 cells.
Figure 5D:
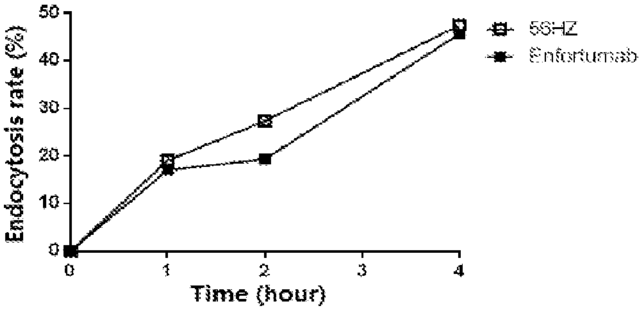
FIG. 5D shows the detection results of endocytosis activity of anti-human Nectin-4 humanized monoclonal antibody 56 HZ on T24-Nectin-4 cells.

The experimental results were shown in FIGS. 4A, 4B and Table 8, indicating that the affinity of 31 HZ and 56 HZ to Nectin-4 on cell membrane surface was comparable to that of Enfortumab.

TABLE 8

Detection of affinity of anti-human Nectin-4 humanized monoclonal antibodies to human Nectin-4 on tumor cell membrane surface

| Antibody name | $EC_{50}$ (ng/mL) T47D | NCI-N87 |
|---|---|---|
| 31HZ | 12.29 | / |
| 56HZ | / | 16.39 |
| 74HZ | 22.28 | / |
| Enfortumab | 10.11 | 22.07 |

Note:
/: not detected.

Example 3: Detection of Endocytic Activity of Anti-Human Nectin-4 Humanized Monoclonal Antibodies The endocytic activity of anti-human Nectin-4 humanized monoclonal antibodies was detected by flow cytometry. The specific steps were as follows: T47D, MDA-MB-468 (a kind of human breast cancer cell, ATCC) or A549-Nectin-4 cells were digested by trypsin and counted, the cells were resuspended in PBS (containing 1% BSA), the cell density was adjusted to $3\times10^6$/mL; 31 HZ, 56 HZ, or 74 HZ antibodies to be tested was added to 100 μL of the resuspended cells at a final concentration of 10 μg/mL, isotype Human IgG was used as a negative control, and incubated on ice for 1 hour; after being washed 3 times with pre-cooled PBS after the incubation, the cells were resuspended with a cell culture medium and divided into two parts, one part was placed in a 37° C. cell incubator and incubated for 1, 2 and 4 hours (endocytosis group), and the other part was kept on ice and incubated for 1, 2 and 4 hours (affinity group); after incubation, washing was performed 3 times with pre-cooled PBS, the cells were resuspended with 50 μL PBS (containing 1% BSA), anti-human fluorescent secondary antibody (BioLegend) was added, and incubated at 4° C. for half an hour; after the incubation, washing was performed 3 times with pre-cooled PBS, and then fluorescent signal (expressed as mean fluorescence intensity (MFI)) on the cells was detected by flow cytometer (Beckman), and antibody endocytosis rate was calculated according to the following formula: endocytosis ratio (%)=[1−(MFI antibody group at 37° C.−MFI control group at 37° C.)/(MFI antibody group on ice−MFI control group on ice)]×100%.

The endocytic activity of 56 HZ on T24-Nectin-4 cells was detected by the same method.

The experimental results were shown in FIGS. 5A to 5D, indicating that the endocytic activities of 31 HZ, 56 HZ and 74 HZ were better than that of Enfortumab.

Example 4: Detection of the Binding Domain of Anti-Human Nectin-4 Humanized Monoclonal Antibodies to Human Nectin-4

Human Nectin-4 contains one IgV domain and two IgC domains. To determine the binding domain of the anti-human Nectin-4 humanized monoclonal antibodies, an A549 stable cell line A549-Nectin-4-IgV overexpressing Nectin-4 IgV domain, and an A549 stable cell line A549-Nectin-4-IgCC overexpressing two IgC domains of Nectin-4 were constructed, and the binding domains of the antibody to be tested were detected by flow cytometry. The specific steps were as follows: A549-Nectin-4-IgV and A549-Nectin-4-IgCC cells were digested, resuspended by centrifugation, washed twice with PBS; the cells were resuspended with PBS (containing 1% BSA), and spread at 300,000 cells/well into a 96-well tip-bottom plate, 50 μl per well; 50 μL of the antibody to be tested at a final concentration of 40 μg/mL was added to each well, and Human IgG was used as a negative control; after being mixed well, the resulting mixture was reacted in the dark at 4° C. for 1 hour; washing was performed 3 times with PBS, FITC-labeled anti-human Fc secondary antibody (brand: BioLegend, product number: 409322) was added, incubated at 4° C. for 0.5 hours in the dark; washing was performed 3 times with PBS, and detection was carried out using a flow cytometer (flow cytometer brand: Beckman, model: Cytoflex).

Figure 6A:
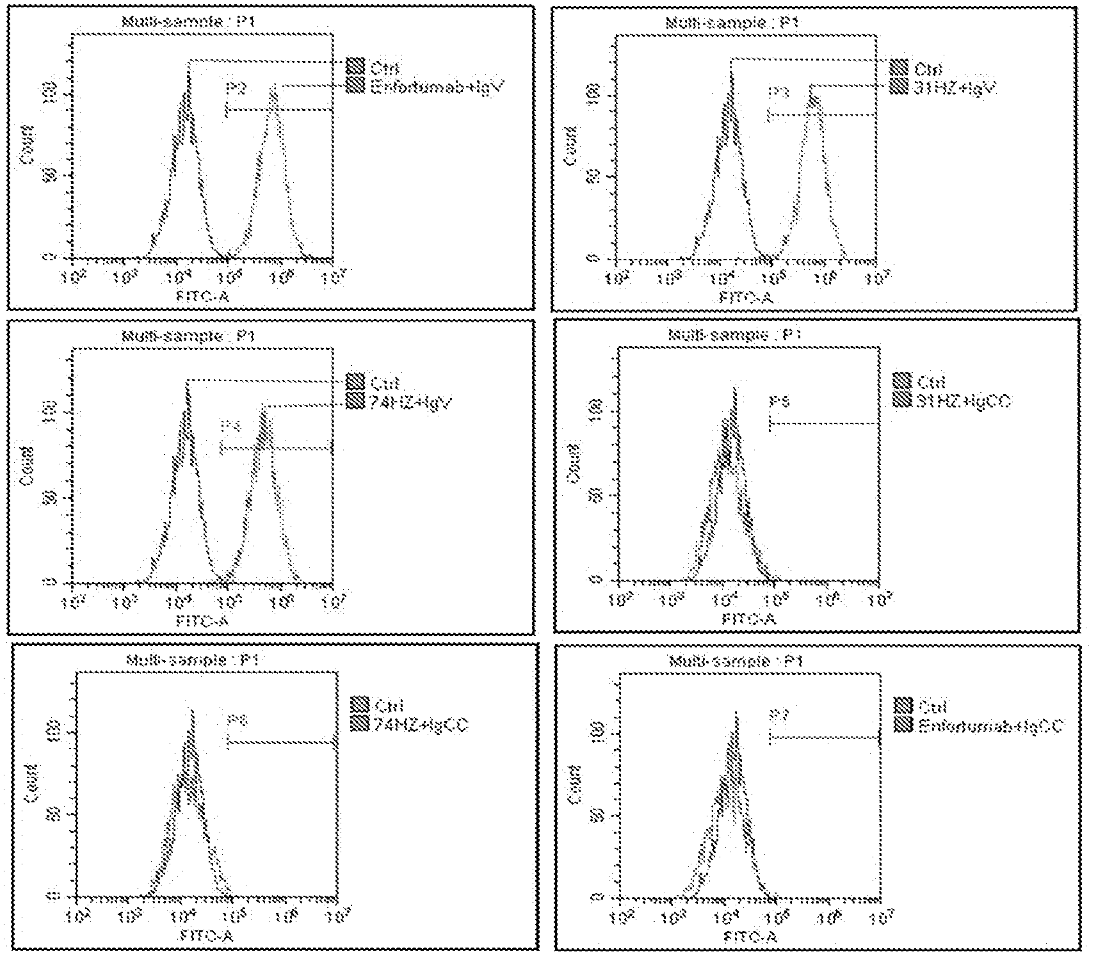
FIG. 6A shows the detection results of anti-human Nectin-4 humanized monoclonal antibody 31 HZ and 74 HZ recognizing human Nectin-4 domain.
Figure 6B:
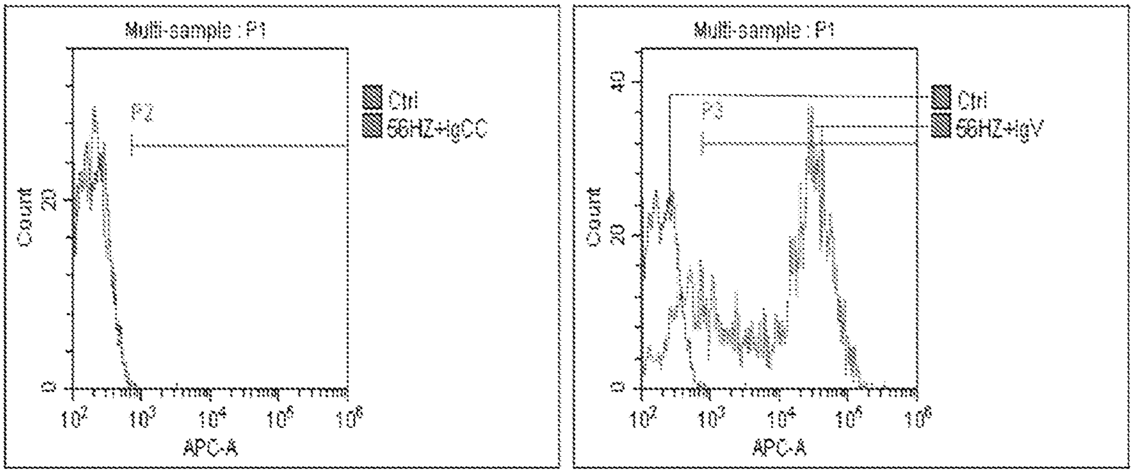
FIG. 6B shows the detection results of anti-human Nectin-4 humanized monoclonal antibody 56 HZ recognizing human Nectin-4 domain.

The experimental results were shown in FIGS. 6A and 6B, indicating that 31 HZ, 56 HZ, 74 HZ and Enfortumab only bound to the IgV domain of human Nectin-4, not to the IgC domain.

Example 5: Detection of Competitive Activity of Anti-Human Nectin-4 Humanized Monoclonal Antibodies Human Nectin-4 is linked to another Nectin-4 molecule or Nectin-1 molecule through the IgV domain. Because 31 HZ, 56 HZ and 74 HZ all bind to the IgV domain of Nectin-4, the competitive activity of the three antibodies was detected by competitive ELISA. The specific steps were as follows: Nectin-4 protein was diluted to 2 μg/mL with CBS coating solution, 100 μL per well, and incubated at 37° C. for 2 hours; washing was performed once with 300 μL PBST, PBS (2% BSA) was then added, 100 μL per well, and incubation was performed at 37° C. for 2 hours; biotin-labeled Nectin-1-hFc was diluted with PBS (2% BSA) to 20 μg/mL; the antibody to be detected was diluted with PBS (2% BSA), wherein the dilution of 31 HZ and 74 HZ was started from 3.73 μg/mL, 3-fold dilution, and 9 concentration points, the dilution of 56 HZ was started from 1.25 μg/mL, 2-fold dilution, and 10 concentration points; the above two diluted solutions were mixed well in equal volumes, and then added to the corresponding well at 100 μL/well, and incubation was performed at room temperature for 2 hours; washing was performed three times with 300 μL PBST; HRP-streptavidin was diluted with PBS (2% BSA) at a ratio of 1:100%, and added to the corresponding well at 100 μL/well, incubation was performed at room temperature for 1 hour; washing was performed five times with 300 μL of PBST; 100 μL of TMB was added to the corresponding well, color development was performed at room temperature for 10 minutes, and then terminated by adding 50 μL of 2N $H_2SO_4$, and a microplate reader was used for collecting readings at 450 nm.

Figure 7A:
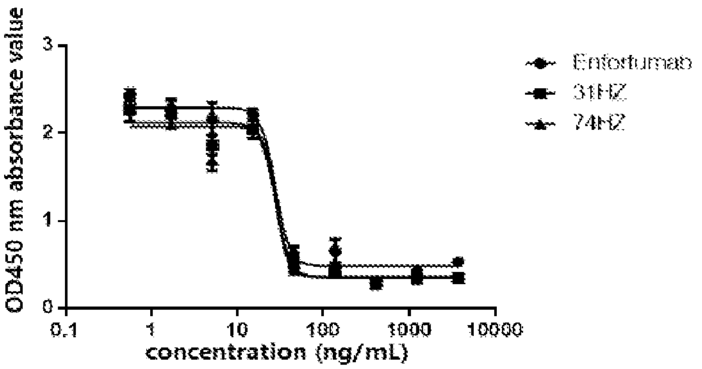
FIG. 7A shows the detection results of competition activity of anti-human Nectin-4 humanized monoclonal antibody 31 HZ and 74 HZ.
Figure 7B:
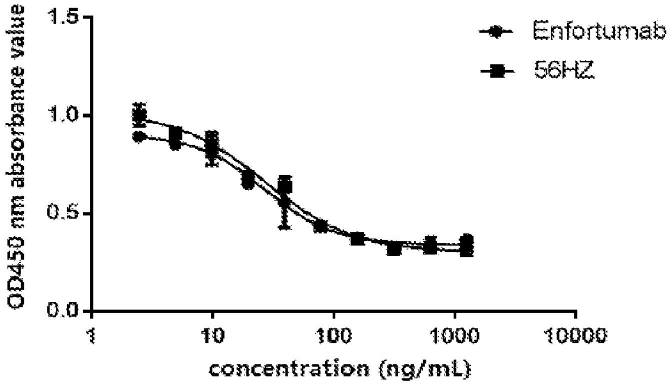
FIG. 7B shows the detection results of competition activity of anti-human Nectin-4 humanized monoclonal antibody 56 HZ.

The experimental results were shown in FIGS. 7A and 7B, indicating that 31 HZ, 56 HZ and 74 HZ could competitively inhibit the binding of human Nectin-4 to human Nectin-1, and their competition $IC_{50}$ values were 27.62 ng/mL, 26.90 ng/mL, and 27.22 ng/mL, respectively, which were comparable to that of Enfortumab (27.11 ng/mL).

Example 6: Detection of Specificity of Anti-Human Nectin-4 Humanized Monoclonal Antibodies The Nectin family includes members of Nectin-1, Nectin-2, Nectin-3 and Nectin-4, and the members share a sequence identity of about 25%, but have similar structure and function. In order to detect whether the anti-human Nectin-4 humanized monoclonal antibodies herein only recognize Nectin-4 and do not recognize Nectin-1, Nectin-2 and Nectin-3, the specificity of the antibodies to be tested were detected by ELISA. The specific steps were as follows: human Nectin-1, Nectin-2, Nectin-3 and Nectin-4 antigens were diluted to 1 μg/mL with CBS coating solution, coated on an ELISA plate at 100 μL per well, and standed overnight at 4° C.; the liquid in the well was discarded on the next day, and washing was performed once with 300 μL of PBS; 100 μL of PBS (containing 2% BSA) was added, and blocking was performed at 37° C. for 2 hours; 31 HZ, 56 HZ, 74 HZ and Enfortumab antibodies were diluted with PBS (containing 2% BSA), 100 μL was taken and added to the corresponding well, incubated at 37° C. for 2 hours; washing was performed 3 times with 300 μL of PBST; HRP-labeled goat anti-human secondary antibody was diluted at a ratio of 1:10000 with PBS (containing 2% BSA), 100 μL was taken and added to the corresponding well, incubation was performed at 37° C. for 1 hour; washing was performed 5 times with 300 μL of PBST; 100 μL of TMB color development solution was added to the corresponding well, and color development was performed at room temperature for 5-20 minutes; 50 μL of 2N $H_2SO_4$ was added for stopping, a microplate reader was used for collecting readings at OD450 nm, and the data were imported into Graphpad Prism for curve fitting.

Figure 8A:
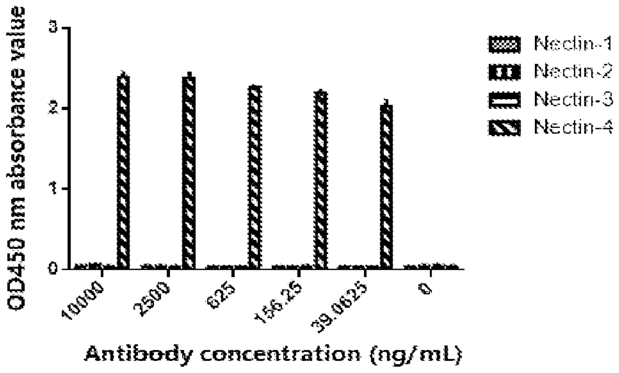
FIG. 8A shows the detection results of specificity of anti-human Nectin-4 humanized monoclonal antibody 31 HZ.
Figure 8B:
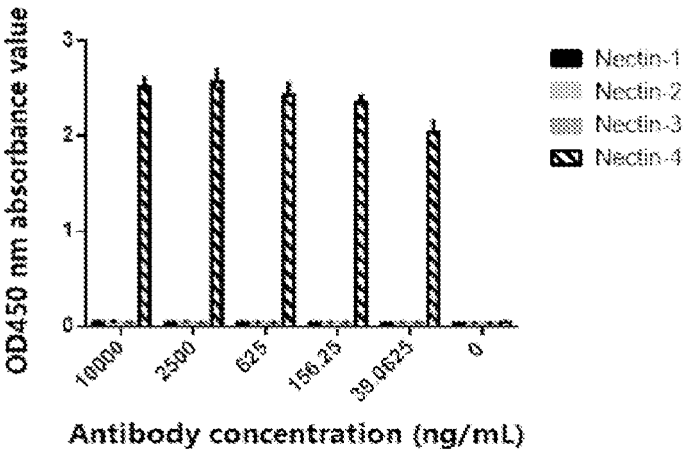
FIG. 8B shows the detection results of specificity of anti-human Nectin-4 humanized monoclonal antibody 74 HZ.
Figure 8C:
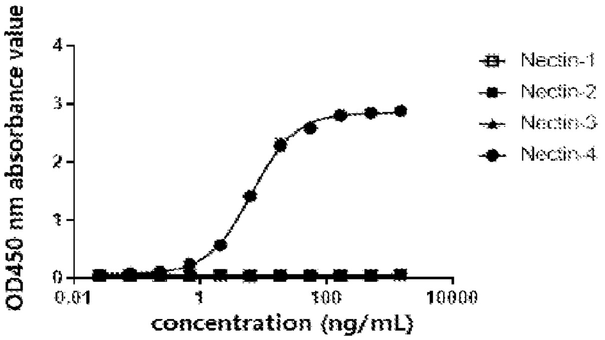
FIG. 8C shows the detection results of specificity of anti-human Nectin-4 humanized monoclonal antibody 56 HZ.

The experimental results were shown in FIGS. 8A, 8B, and 8C, indicating that 31 HZ, 56 HZ and 74 HZ all specifically recognized human Nectin-4, but did not recognize Nectin-1, Nectin-2 and Nectin-3.

Example 7: Preparation of Anti-Human Nectin-4 ADC

The anti-human Nectin-4 ADC was prepared by coupling TL001 with anti-human Nectin-4 humanized monoclonal antibody, wherein the structure of TL001 was shown in Formula (1):

Formula (1)

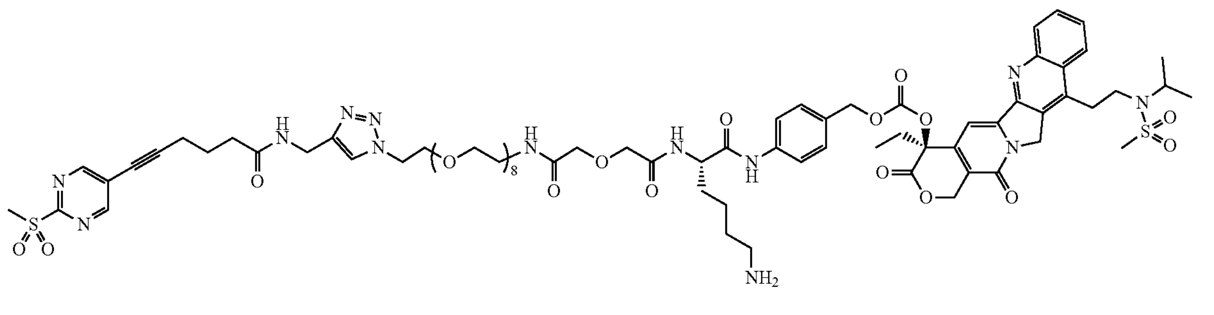

The preparation method of TL001 can be referred to WO2019/114666, the relevant content of which is incorporated herein by reference in its entirety.

The preparation method of anti-human Nectin-4 antibody conjugate (anti-human Nectin-4 ADC) was as follows:

(1) Coupling: 30 mg of anti-human Nectin-4 humanized monoclonal antibody was taken, diluted with a diluent (20 mM PB+105 mM NaCl, pH 7.7), and edetate sodium solution with a final concentration of 5 mM was added, and mixed well; added with TCEP solution (the molar ratio of TCEP to the antibody was 4.4:1), mixed well, standed at room temperature for 30 minutes; TL001 (the molar ratio of TL001 to the antibody was 9:1) dissolved in dimethyl sulfoxide was added to the above solution system, mixed well, and standed at room temperature for 2 hours to obtain the coupled samples, which were named as 31 HZ-TL001, 56 HZ-TL001, 74 HZ-TL001 and Enfortumab-TL001, respectively. The anti-human Nectin-4 ADCs were subjected to buffer exchange and then stored in aliquots at 4° C.

(2) Detection:

Molecular weight of anti-human Nectin-4 ADCs was analyzed by LC-MS under the following conditions:

Chromatography conditions:

Liquid chromatography column: Thermo MAbPac RP 3.0×100 mm;

Mobile phase A: 0.1% FA/98% $H_2O$/2% ACN;

Mobile phase B: 0.1% FA/2% $H_2O$/98% ACN;

Flow rate: 0.25 mL/min; sample chamber temperature: 8° C.; column temperature: 60° C.; sample size: 1 μL;

| Time (min) | 2 | 20 | 22 | 25 | 26 | 30 |
|---|---|---|---|---|---|---|
| Mobile phase A (%) | 75 | 60 | 5 | 5 | 75 | 75 |
| Mobile phase B (%) | 25 | 40 | 95 | 95 | 25 | 25 |

Switching valve: 0-3 min to waste, 3-22 min to MS, 22-30 min to waste

Mass spectrometry conditions:

Mass spectrometer model: AB Sciex Triple TOF 5600+;

Parameters: GS1 35; GS2 35; CUR 30; TEM 350; ISVF 5500; DP 200; CE 10; m/z 600-4000; Time bins to sum 40.

The theoretical molecular weight and the measured molecular weight of the light chain and heavy chain of the coupled anti-human 31 HZ-TL001 (the heavy chain was calculated by the main glycoform GOF) were shown in the following table:

| | Peptide chain | mAb | DAR1 | DAR2 | DAR3 | DAR4 |
|---|---|---|---|---|---|---|
| LC | Theoretical value (Da) | 23987.65 | 25538.39 | / | / | / |
| | Measured value (Da) | 23987.38 | 25539.03 | / | / | / |
| HC | Theoretical value (Da) | 50679.13 | 52529.15 | 54078.89 | 55628.62 | 57179.37 |
| | Measured value (Da) | N/D | 52529.13 | 54079.31 | 55629.57 | 57180.06 |

The light chain of 31 HZ-TL001 coupled with 0 to 1 toxin (the proportions of LC and DAR1 were 0.1% and 99.9%, respectively), and the heavy chain coupled with 0 to 4 toxins (the proportions of HC, DAR1, DAR2, DAR3 and DAR4 were 0.0%, 2.0%, 10.2%, 86.1%, 1.8%, respectively), the drug-antibody ratio (DAR) of toxin to antibody was therefore calculated to be 7.75, according to the calculation formula: DAR=light chain DAR1×2+heavy chain (DAR1×1+DAR2×2+DAR3×3+DAR4×4)×2.

By using the same method, the detected DAR values of 56 HZ-TL001, 74 HZ-TL001 and Enfortumab-TL001 were 7.71, 7.98 and 8.01, respectively.

According to the above analysis results of mass spectrometry, the structure of anti-human Nectin-4 ADC should be determined as:

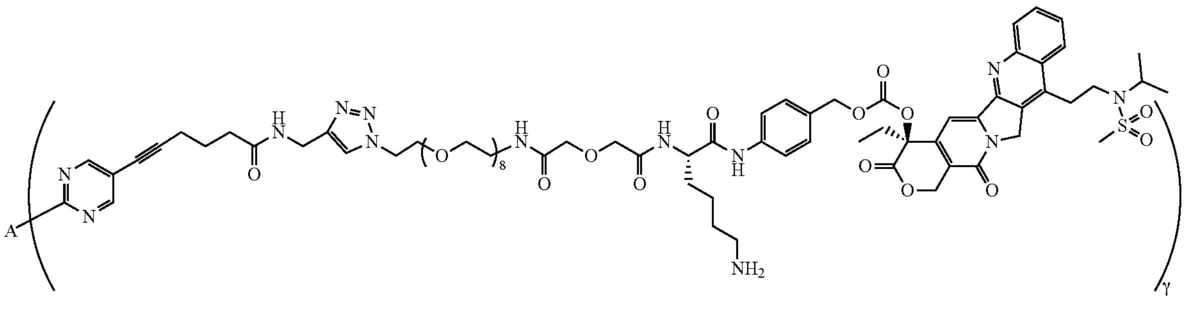

wherein A represents an anti-human Nectin-4 humanized monoclonal antibody; γ refers to the number of TL001 linked to A by forming thioether bond with the thiol group of A, and is an integer of 1 to 10.

Enfortumab-VC-MMAE was prepared by coupling VC-MMAE with Enfortumab. The preparation and detection methods were as described above, and the molar ratio of antibody to VC-MMAE was 1:5. The DAR value of this batch of Enfortumab-VC-MMAE was: 5.09.

Example 8: Detection of Killing Activity of Anti-Human Nectin-4 ADCs on Tumor Cell Line with High Expression of Human Nectin-4

A549-Nectin-4 stable cell line was selected to detect the killing activity of 31 HZ-TL001, 74 HZ-TL001 and Enfortumab-TL001 on cell lines with high expression of human Nectin-4. The specific experimental steps were as follows: A549-Nectin-4 cells were digested, the cells were collected by centrifugation, resuspended to 100,000/mL with DMEM+4% FBS medium, and spreaded at 100 μL/well cells into a 96-well plate; ADC molecules were diluted by gradient with DMEM basal medium, starting from a final concentration of 150 μg/mL, 4-fold dilution, 11 concentration points, and added to corresponding wells, 100 μL per well, and the final serum concentration was 2%; incubation was performed in a 37° C., 5% $CO_2$ incubator for 72 hours; CCK8 (Rhinogen) was added, 20 μL/well, and incubated for 0.5-2.5 hours in a 37° C., 5% $CO_2$ incubator, OD450 nm readings were obtained on a microplate reader (MD) every half an hour and imported into Graphpad Prism for curve fitting.

Figure 9A:
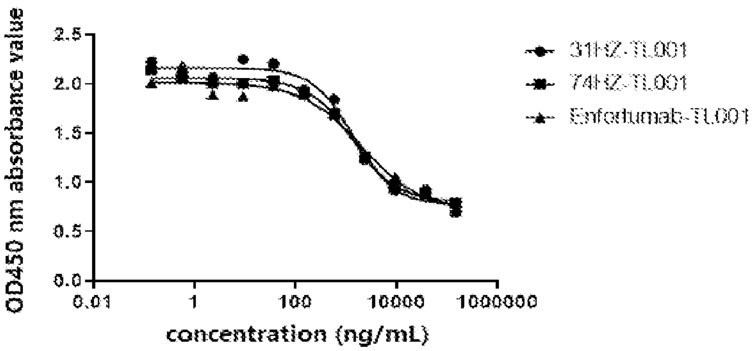
FIG. 9A shows the results of anti-human Nectin-4 ADCs 31 HZ-TL001 and 74 HZ-TL001 killing A549-Nectin-4 cells.
Figure 9B:
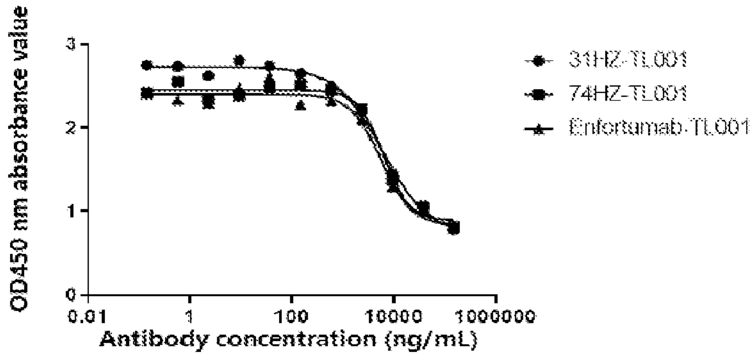
FIG. 9B shows the results of anti-human Nectin-4 ADC 31 HZ-TL001 and 74 HZ-TL001 killing A549 cells.

The experimental results were shown in FIGS. 9A and 9B, indicating that 31 HZ-TL001, 74 HZ-TL001 and Enfortumab-TL001 all could effectively kill A549-Nectin-4 cells, with $EC_{50}$ values of 1390 ng/mL, 1364 ng/mL and 2049 ng/mL, respectively, it showed that the killing activities of 31 HZ-TL001 and 74 HZ-TL001 on tumor cell lines with high expression of human Nectin-4 were better than that of Enfortumab-TL001; meanwhile, the killing activity $EC_{50}$ values of 31 HZ-TL001, 74 HZ-TL001 and Enfortumab-TL001 on A549 cells without overexpressing human Nectin-4 were 5982 ng/mL, 6251 ng/mL and 5604 ng/mL, respectively. Overall, in terms of killing activity on A549-Nectin-4 cells and A549 cells, 31 HZ-TL001, 74 HZ-TL001 and Enfortumab-TL001 are Nectin-4 specific.

Figure 9C:
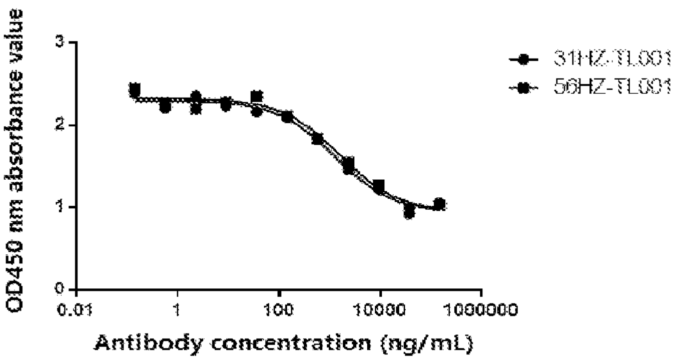
FIG. 9C shows the results of anti-human Nectin-4 ADCs 31 HZ-TL001 and 56 HZ-TL001 killing T24-Nectin-4 cells.
Figure 9D:
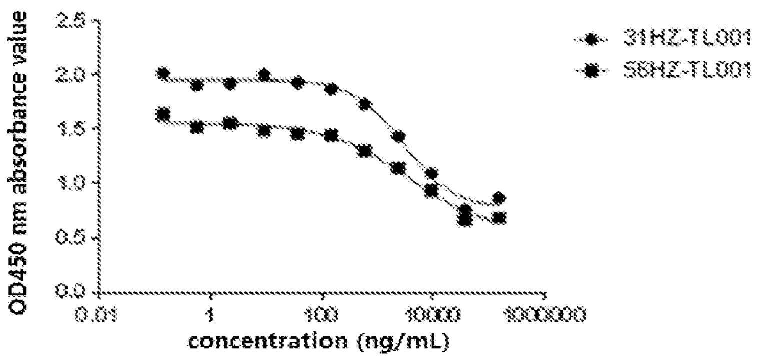
FIG. 9D shows the results of anti-human Nectin-4 ADC 31 HZ-TL001 and 56 HZ-TL001 killing T24 cells.

The killing activities of 31 HZ-TL001 and 56 HZ-TL001 on T24-Nectin-4 cell line with high expression of human Nectin-4 were detected by the same experimental method described above. The experimental results were shown in FIGS. 9C and 9D, which showed that both 31 HZ-TL001 and 56 HZ-TL001 could effectively kill T24-Nectin-4 cells, and their $EC_{50}$ values were 1277 ng/mL and 1568 ng/mL, respectively, indicating that the killing activities of the two ADCs were substantially equivalent; the killing activity $EC_{50}$ values of 31 HZ-TL001 and 56 HZ-TL001 on T24 cells without overexpressing human Nectin-4 were 2884 ng/mL and 3665 ng/mL, respectively, and these killing activities were significantly weaker than those on T24-Nectin-4 cells, indicating that the killing effect of both was Nectin-4 specific.

Example 9: Detection of Killing Activity of Anti-Human Nectin-4 ADC on Tumor Cell Line Endogenously Expressing Human Nectin-4

T47D tumor cell line was selected to detect the killing activity of 31 HZ-TL001, 74 HZ-TL001 and Enfortumab-TL001 on tumor cell line endogenously expressing human Nectin-4. The specific experimental steps were as follows: T47D cells were digested, the cells were collected by centrifugation, resuspended to 100,000/mL in 1640+4% FBS medium, and spreaded at 100 μL/well cells into a 96-well plate; ADC molecules were diluted by gradient with 1640 basal medium, starting at a final concentration of 150 μg/mL, 4-fold dilution, 11 concentration points, and added to the corresponding wells, 100 μL per well, the final serum concentration was 2%; the incubation was performed in a 37° C., 5% $CO_2$ incubator for 72 hours; CCK8 (Rhinogen) was added, 20 μL/well, and incubated for 0.5-2.5 hours in a 37° C., 5% $CO_2$ incubator, OD450 nm readings were collected on a microplate reader (MD) every half an hour and imported into Graphpad Prism for curve fitting.

Figure 10A:
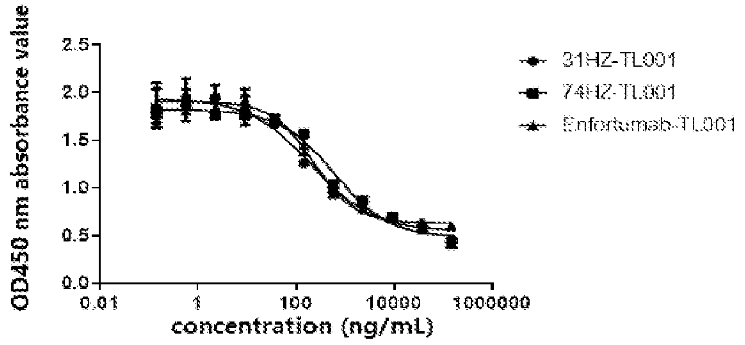
FIG. 10A shows the results of anti-human Nectin-4 ADC 31 HZ-TL001 and 74 HZ-TL001 killing T47D cells.

The experimental results were shown in FIG. 10A, indicating that 31 HZ-TL001, 74 HZ-TL001 and Enfortumab-TL001 could effectively kill T47D cells, with $EC_{50}$ values of 206.1 ng/mL, 611.3 ng/mL and 229.2 ng/mL, respectively, it showed that the killing activity of 31 HZ-TL001 on T47D cells was comparable to that of Enfortumab-TL001.

Figure 10B:
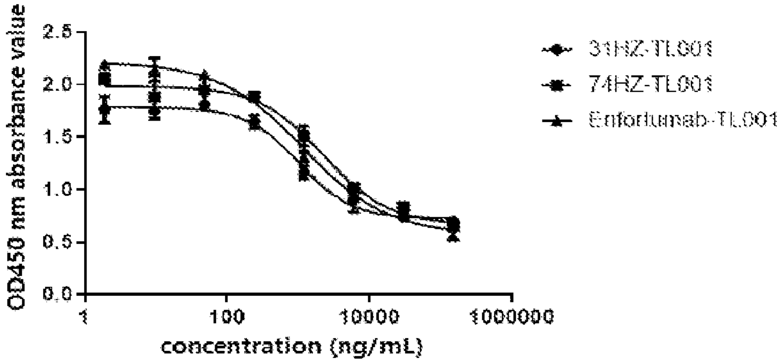
FIG. 10B shows the results of anti-human Nectin-4 ADC 31 HZ-TL001 and 74 HZ-TL001 killing MDA-MB-468 cells.

The killing activity of 31 HZ-TL001, 74 HZ-TL001 and Enfortumab-TL001 on tumor cell line MDA-MB-468 endogenously expressing human Nectin-4 was detected by the same experimental method described above. The experimental results were shown in FIG. 10B, which showed that 31 HZ-TL001, 74 HZ-TL001 and Enfortumab-TL001 could effectively kill MDA-MB-468 cells, and their $EC_{50}$ values were 1030 ng/mL, 2277 ng/mL and 1190 ng/mL, respectively, indicating that the killing activity of 31 HZ-TL001 on MDA-MB-468 cells was comparable to that of Enfortumab-TL001.

Figure 10C:
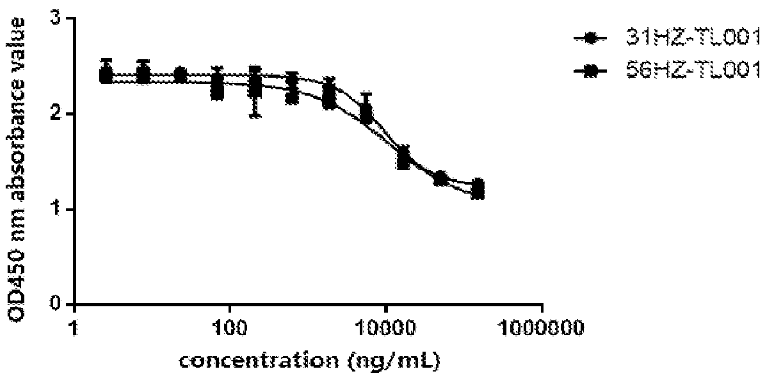
FIG. 10C shows the results of anti-human Nectin-4 ADC 31 HZ-TL001 and 56 HZ-TL001 killing NCI-N87 cells.

The killing activity of 31 HZ-TL001 and 56 HZ-TL001 on tumor cell line NCI-N87 endogenously expressing human Nectin-4 was detected by the same experimental method as described above. The experimental results were shown in FIG. 10C, which showed that both 31 HZ-TL001 and 56 HZ-TL001 could effectively kill NCI-N87 cells, and their $EC_{50}$ values were 9376 ng/mL and 10935 ng/mL, respectively, indicating that the killing activities of the two were substantially equivalent.

In conclusion, the killing activities of 31 HZ-TL001 and 56 HZ-TL001 on tumor cell lines endogenously expressing human Nectin-4 were substantially equivalent to those of Enfortumab-TL001.

Example 10: In Vivo Pharmacodynamic of Anti-Human Nectin-4 ADC in CDX Model

The anti-tumor effect of ADC molecules was evaluated by constructing a CDX model of human non-small cell lung cancer cell line NCI-H322M. The specific steps were as follows: NCI-H322M cells were cultured with RPMI1640 medium containing 10% fetal bovine serum (FBS) at 37° C. and 5% $CO_2$. The cells in exponential growth phase were collected, resuspended in PBS, and inoculated subcutaneously into female NOD/SCID mice (Biocytogen Jiangsu Gene Biotechnology Co., Ltd.) at $1\times10^7$/mouse (suspended in 0.1 mL of PBS) to establish subcutaneous xenograft tumor model. When the average tumor volume reached 70-100 $mm^3$, the mice were randomized according to tumor volume, and 5 mice in each group. The day of grouping was recorded as Day 0, and the groups included vehicle group (normal saline) (negative control), 31 HZ-TL001 groups (3 mg/kg and 10 mg/kg), 56 HZ-TL001 groups (3 mg/kg and 10 mg/kg), Enfortumab-TL001 group (10 mg/kg) and Enfortumab-VC-MMAE group (10 mg/kg). All samples were administered via tail vein injection twice a week for a total of 6 doses.

Tumor diameters were measured by a vernier caliper twice a week after administration, and tumor volume was calculated according to the following formula: $V=0.5a\times b^2$, wherein a and b represent the long and short diameters of the tumor, respectively. Animal deaths were observed and recorded daily.

The following formula was used to calculate the tumor growth inhibition rate TGI (%), which was used to evaluate the tumor inhibition efficacy:

$$TGI\ (\%)=[1-(V_{T\text{-}end}-V_{T\text{-}start})/(V_{C\text{-}end}-V_{C\text{-}start})]*100\%$$

wherein $V_{T\text{-}end}$: mean tumor volume of the treatment group at the end of the experiment;

$V_{T\text{-}start}$: mean tumor volume of the treatment group at the start of the administration;

$V_{c\text{-}end}$: mean tumor volume of the negative control group at the end of the experiment;

$V_{c\text{-}start}$: mean tumor volume of the negative control group at the start of the administration.

Figure 11:
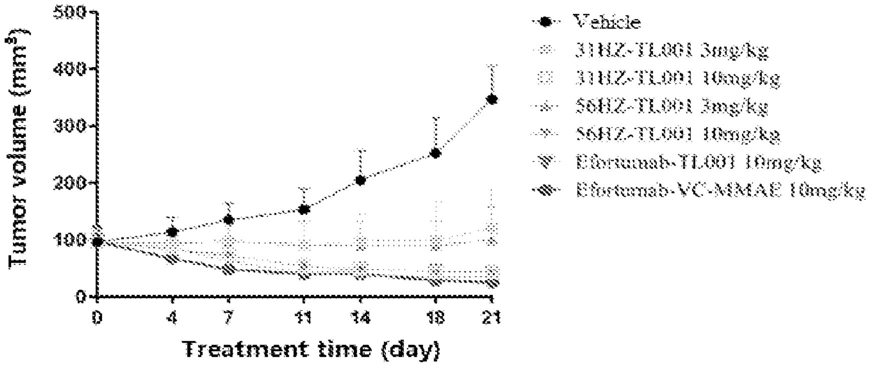
FIG. 11 shows the changes of tumor volume of each group of mice over time in the subcutaneous NCI-H322M cell xenograft tumor model of NOD/SCID mice.
Figure 12:
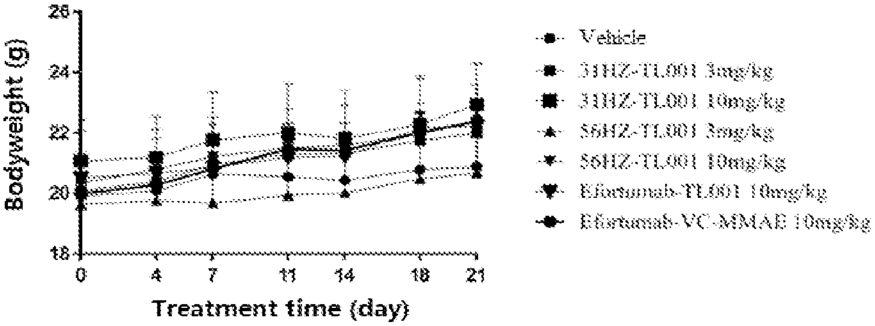
FIG. 12 shows the changes of body weight of each group of mice over time in the subcutaneous NCI-H322M cell xenograft tumor model of NOD/SCID mice.

The experimental results were shown in Table 9 and FIGS. 11 and 12, which showed that 31 HZ-TL001, 56 HZ-TL001, Enfortumab-TL001 and Enfortumab-VC-MMAE had significant inhibitory effects on the tumor growth in the NCI-H322M xenograft tumor model, in a dose-dependent manner. After 6 doses (Day 21), compared to the negative control group, at the 10 mg/kg dose level, the TGI values of 31 HZ-TL001, 56 HZ-TL001, Enfortumab-TL001 and Enfortumab-VC-MMAE were 155.79%, 163.56%, 156.31% and 173.79%, respectively. There was no significant body weight loss in all treatment groups during the observation period, indicating the well-tolerated of the animals to the ADCs.

TABLE 9

| NCI-H322M + NOD/SCID mouse CDX model | | | | | |
|---|---|---|---|---|---|
| | | Day 21 | | | |
| Group | Dose (mg/kg) | Tumor volume ($mm^3$) ($\bar{x}$ ± SEM) | TGI (%) | Tumor regression (PR/CR) | P value |
| Vehicle | 10 | 347.06 ± 25.84 | / | (0/0) | / |
| 31HZ-TL001 | 3 | 119.96 ± 32.99 | 90.61 | (1/0) | <0.001 |
| 31HZ-TL001 | 10 | 42.92 ± 3.00 | 155.79 | (5/0) | <0.001 |
| 56HZ-TL001 | 3 | 100.12 ± 25.64 | 98.33 | (4/0) | <0.001 |
| 56HZ-TL001 | 10 | 35.53 ± 2.12 | 163.56 | (5/0) | <0.001 |
| Enfortumab-TL001 | 10 | 42.62 ± 5.38 | 156.31 | (5/0) | <0.001 |
| Enfortumab-VC-MMAE | 10 | 25.47 ± 4.70 | 173.79 | (5/0) | <0.001 |

Note:

TGI: tumor growth inhibition rate; PR: partial regression of tumor; CR: complete regression of tumor. P value was a result compared with the vehicle group.

The above results indicated that, in view of the TGI values of 31 HZ-TL001 and 56 HZ-TL001 at the dose levels of 3 mg/kg and 10 mg/kg, both 31 HZ-TL001 and 56 HZ-TL001 could effectively inhibit tumor growth in a dose-dependent manner. At the dose level of 10 mg/kg, both 31 HZ-TL001 and 56 HZ-TL001 could partially regress tumors of all the 5 mice in the group, and the efficacy was basically equivalent to those of Enfortumab-TL001 and Enfortumab-VC-MMAE. In addition, 31 HZ-TL001 and 56 HZ-TL001 were well tolerated by tumor-bearing mice.

Example 11: In Vivo Pharmacodynamic of Anti-Human Nectin-4 ADC in PDX Model

Tumor tissue was collected from HuPrime® bladder cancer xenograft model BL9200 (Crown Bioscience (Taicang) Co., Ltd., with high expression of Nectin-4, derived from a 63-year-old male patient) tumor-bearing mice, cut into pieces with a diameter of 3×3×3 mm, and inoculated subcutaneously at right anterior scapula of NOD/SCID mice (Jiangsu Jicui Yaokang Biotechnology Co., Ltd.). When the average tumor volume of tumor-bearing mice reached about 150-250 $mm^3$, the mice were randomly divided into groups according to tumor size, 7 mice in each group, and the day of grouping was defined as Day 0. There were 4 groups: Human IgG1 isotype control antibody group (IgG1 3 mg/kg, negative control), Human IgG1-TL001 group (abbreviated as IgG1-TL001, 3 mg/kg; see Example 7 for the preparation method), 1 mg/kg group and 3 mg/kg group for 56 HZ-TL001. All samples were administered via tail vein injection twice a week for a total of 6 doses. After administration, the tumor volume and body weight of the mice were observed and periodically measured, and the measurement and calculation methods were as described in Example 10.

Figure 13:
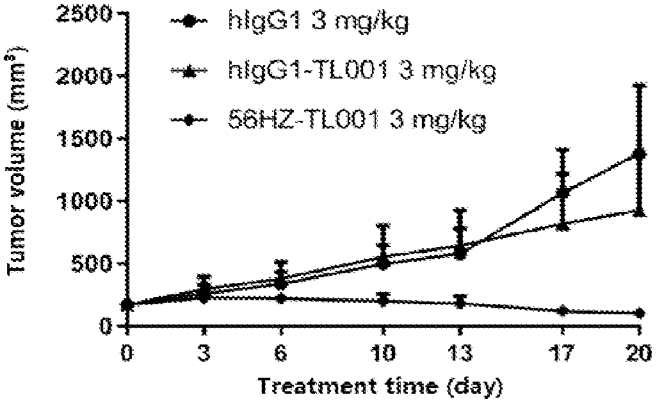
FIG. 13 shows the changes of tumor volume of each group of mice over time in the subcutaneous HuPrime® gastric cancer BL9200 PDX model of NOD/SCID mice.
Figure 14:
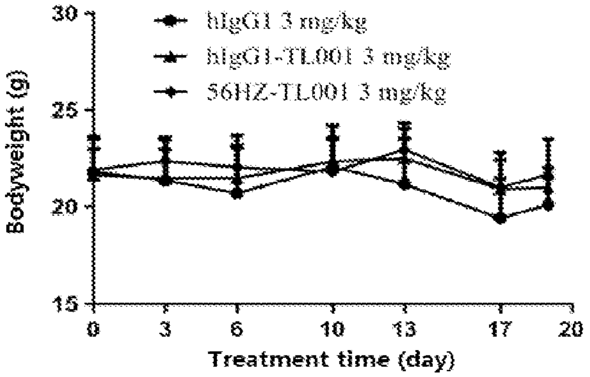
FIG. 14 shows the changes of body weight of each group of mice over time in the subcutaneous HuPrime® gastric cancer BL9200 PDX model of NOD/SCID mice.

The experimental results were shown in Table 10 and FIGS. 13 and 14. After 6 doses (Day 20), compared to the 3 mg/kg Human IgG1 (hIgG1) negative control group, 56 HZ-TL001 at 3 mg/kg showed an inhibitory TGI of 105.55% ($P<0.05$) for tumor growth, and partial regression of tumors was observed in 4 mice of this group; 56 HZ-TL001 at 3 mg/kg showed significantly improved inhibitory effect on tumor growth than the isotype control ADC (hIgG1-TL001 at 3 mg/kg) ($P<0.001$) at the same dose. One mouse died in the hIgG1 group, and no death was observed in other groups with normal activities. During the administration period, the body weight of the mice in each group decreased slightly, among which the body weight of the IgG1 group decreased the most due to the lack of effective treatment, indicating that the tumor-bearing mice were well tolerated to the ADCs.

The above results showed that 56 HZ-TL001 showed significant inhibitory effect on the tumor growth of the BL9200 bladder cancer PDX xenograft model. In addition, the tumor-bearing mice were well tolerated to 56 HZ-TL001.

TABLE 10

| HuPrime ® bladder cancer + NOD/SCID mouse PDX model | | | | | | |
|---|---|---|---|---|---|---|
| | | Day 20 | | | | |
| Group | Dose (mg/kg) | Tumor volume ($mm^3$) ($\bar{x}$ ± SEM) | TGI (%) | Tumor regression (PR/CR) | P value (relative to hIgG1) | P value (relative to hIgG1-TL001) |
| hIgG1 | 3 | 1379.58 ± 221.96 | / | 0/0 | / | / |
| hIgG1-TL001 | 3 | 926.31 ± 163.85 | 37.47 | 0/0 | >0.05 | / |
| 56HZ-TL001 | 3 | 101.71 ± 16.78 | 105.55 | 4/0 | <0.001 | <0.001 |

Note:
TGI: tumor growth inhibition rate; PR: partial regression of tumor; CR: complete regression of tumor; /: not applicable.

Although specific embodiments of the present invention have been described in detail, those skilled in the art will appreciate that various modifications and variants can be made to the details in light of all the teachings that have been disclosed, and that these changes are all within the scope of the present invention. The scope of the present invention is given by the appended claims and any equivalents thereof.

List of sequences

| SEQ ID NO: | Description | Amino acid sequence |
|---|---|---|
| 1 | 31# VH | EVQLQQPGADLVRPGASVKLSCKASGYTFTD YWMNWVKLRPGQGLEWIGMIHPSDSETRLNQ KFKDKATLTVDKSSSTAYMQLSSPTSEDSAV YYCARWDFRIYYAMDYWGQGTSVTVSS |
| 2 | 31# VL | DVVITQSPSSLAMSVGQKVTMSCKSSQSLLN TNSQKNYLAWYQQKPGQSPKLLVYFASTRES GVPDRFIGSGSGTDFTLTITSVQAEDLADYF CQQHYSTPLTFGAGTKLEIK |
| 3 | Chothia 31#/31HZ CDR-H1 | GYTFTDY |
| 4 | Chothia 31#/31HZ CDR-H2 | HPSDSE |
| 5 | Chothia/Abm/Kabat 31#/ 31HZ CDR-H3 | WDFRIYYAMDY |
| 6 | Chothia/Abm/Kabat 31#/ 31HZ CDR-L1 | KSSQSLLNTNSQKNYLA |
| 7 | Chothia/Abm/Kabat 31#/ 31HZ CDR-L2 | FASTRES |
| 8 | Chothia/Abm/Kabat/IMGT 31#/31HZ/74#/74HZ CDR-L3 | QQHYSTPLT |
| 9 | Abm 31#/31HZ CDR-H1 | GYTFTDYWMN |
| 10 | Abm 31#/31HZ CDR-H2 | MIHPSDSETR |
| 11 | Kabat 31#/31HZ CDR-H1 | DYWMN |
| 12 | Kabat 31# CDR-H2 | MIHPSDSETRLNQKFKD |
| 13 | IMGT 31#/31HZ CDR-H1 | GYTFTDYW |
| 14 | IMGT 31#/31HZ CDR-H2 | IHPSDSET |
| 15 | IMGT 31#/31HZ CDR-H3 | ARWDFRIYYAMDY |
| 16 | IMGT 31#/31HZ CDR-L1 | QSLLNTNSQKNY |
| 17 | IMGT 31#/31HZ CDR-L2 | FAS |
| 18 | Chothia 56HZ CDR-H1 | GYFNSITSDY |
| 19 | 56# VH | QVQLKESGPGLVKPSQSLSLTCTVTGYSITS DYDWHWIRHFPGNMLEWMGYISFSGRTYYNP SLKSRISITHDTSKNHFFLRLNSVTTEDTAT YYCARGNYDGFDYWGQGTTLTVSS |

-continued

| List of sequences | | |
|---|---|---|
| SEQ ID NO: | Description | Amino acid sequence |
| 20 | 56# VL | DIQLTQSPAILSVSPGERVSFSCRASQNIGT SIHWYQHRTNGSPRLLIKFASESISGIPSRF SGSGSGTDFTLSINSVESEDIADYYCQQSKS WPTYTFGGGTKLEIK |
| 21 | Chothia 56# CDR-H1 | GYSITSDY |
| 22 | Chothia 56#/56HZ CDR-H2 | SFSGR |
| 23 | Chothia/Abm/Kabat 56#/ 56HZ CDR-H3 | GNYDGFDY |
| 24 | Chothia/Abm/Kabat 56#/ 56HZ CDR-L1 | RASQNIGTSIH |
| 25 | Chothia/Abm/Kabat 56#/ 56HZ CDR-L2 | FASESIS |
| 26 | Chothia/Abm/Kabat/IMGT 56#/56HZ CDR-L3 | QQSKSWPTYT |
| 27 | Abm 56# CDR-H1 | GYSITSDYDWH |
| 28 | Abm 56#/56HZ CDR-H2 | YISFSGRTY |
| 29 | Kabat 56# CDR-H1 | SDYDWH |
| 30 | Kabat 56#/56HZ CDR-H2 | YISFSGRTYYNPSLKS |
| 31 | IMGT 56# CDR-H1 | GYSITSDYD |
| 32 | IMGT 56#/56HZ CDR-H2 | ISFSGRT |
| 33 | IMGT 56#/56HZ CDR-H3 | ARGNYDGFDY |
| 34 | IMGT 56#/56HZ CDR-L1 | QNIGTS |
| 35 | IMGT 56#/56HZ CDR-L2 | FAS |
| 36 | Abm 56HZ CDR-H1 | GYFNSITSDYDWH |
| 37 | 74# VH | EVQLQQPGAELVRPGASVKLSCKASGYTFIN YWMNWVKQRPGQGLEWIGMIHPSDSATRLNQ KFKDKATLTVDKSSSTAYMQLSSPTSEDSAV YYCARWGNFYTVNAWYYFDYWGHGTTLTVSS |
| 38 | 74# VL | DIVITQSPSSLAMSVGQKVTMSCKSSQTLLN SNTQKNYLAWYQQKPGQSPKLLFYFASTRES GVPDRFIGSGSGTNFTLTISSVQAEDLADYF CQQHYSTPLTFGAGTKLEIK |
| 39 | Chothia 74#/74HZ CDR-H1 | GYTFINY |
| 40 | Chothia 74#/74HZ CDR-H2 | HPSDSA |
| 41 | Chothia/Abm/Kabat 74#/ 74HZ CDR-H3 | WGNFYTVNAWYYFDY |
| 42 | Chothia/Abm/Kabat 74#/ 74HZ CDR-L1 | KSSQTLLNSNTQKNYLA |
| 43 | Chothia/Abm/Kabat 74#/ 74HZ CDR-L2 | FASTRES |
| 44 | Kabat 56HZ CDR-H1 | ITSDYDWH |
| 45 | Abm 74#/74HZ CDR-H1 | GYTFINYWMN |
| 46 | Abm 74#/74HZ CDR-H2 | MIHPSDSATR |
| 47 | Kabat 74#/74HZ CDR-H1 | NYWMN |

-continued

List of sequences

| SEQ ID NO: | Description | Amino acid sequence |
|---|---|---|
| 48 | Kabat 74#CDR-H2 | MIHPSDSATRLNQKFKD |
| 49 | IMGT 74#/74HZ CDR-H1 | GYTFINYW |
| 50 | IMGT 74#/74HZ CDR-H2 | IHPSDSAT |
| 51 | IMGT 74#/74HZ CDR-H3 | ARWGNFYTVNAWYYFDY |
| 52 | IMGT 74#/74HZ CDR-L1 | QTLLNSNTQKNY |
| 53 | IMGT 74#/74HZ CDR-L2 | FAS |
| 54 | IMGT 56HZ CDR-H1 | GYFNSITSDYD |
| 55 | 31HZ VH | QVQLVQSGAEVKKPGSSVKVSCKASGYTFTD YWMNWVRLAPGQGLEWIGMIHPSDSETRLNQ KFQGRVTLTVDKSTSTAYMELSSLRSEDTAV YYCARWDFRIYYAMDYWGQGTLVTVSS |
| 56 | 31HZ VL | DVVITQSPDSLAVSLGERATINCKSSQSLLN TNSQKNYLAWYQQKPGQSPKLLVYFASTRES GVPDRFSGSGSGTDFTLTISSLQAEDVAVYF CQQHYSTPLTFGGGTKVEIK |
| 57 | 56HZ VH | QVQLQESGPGLVKPSQTLSLTCTVSGYFNSI TSDYDWHWIRHHPGKGLEWMGYISFSGRTYY NPSLKSRVTISHDTSKNQFSLKLSSVTAADT AVYYCARGNYDGFDYWGQGTLVTVSS |
| 58 | 56HZ VL | DIVLTQSPATLSLSPGERATLSCRASQNIGT SIHWYQHKPGQSPRLLIKFASESISGIPARF SGSGSGTDFTLTISSLEPEDFAVYYCQQSKS WPTYTFGGGTKVEIK |
| 59 | 74HZ VH | QVQLVQSGAEVKKPGSSVKVSCKASGYTFIN YWMNWVRQAPGQGLEWIGMIHPSDSATRLNQ SFQGRVTLTVDKSTSTAYMELSSLRSEDTAV YYCARWGNFYTVNAWYYFDYWGQGTLVTVSS |
| 60 | 74HZ VL | DIVITQSPDSLAVSLGERATINCKSSQTLLN SNTQKNYLAWYQQKPGQSPKLLFYFASTRES GVPDRFSGSGSGTDFTLTISSLQAEDVAVYF CQQHYSTPLTFGQGTKLEIK |
| 61 | IgG1 heavy chain constant region | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVHNAKTKPREEQYNSTYRVV SVLTVLHQDWLNGKEYKCKVSNKALPAPIEK TISKAKGQPREPQVYTLPPSRDELTKNQVSL TCLVKGFYPSDIAVEWESNGQPENNYKTTPP VLDSDGSFFLYSKLTVDKSRWQQGNVFSCSV MHEALHNHYTQKSLSLSPGK |
| 62 | Kappa light chain constant region | RTVAAPSVFIFPPSDEQLKSGTASVVCLLNN FYPREAKVQWKVDNALQSGNSQESVTEQDSK DSTYSLSSTLTLSKADYEKHKVYACEVTHQG LSSPVTKSFNRGEC |
| 63 | Kabat 31HZ CDR-H2 | MIHPSDSETRLNQKFQG |
| 64 | Kabat 74HZ CDR-H2 | MIHPSDSATRLNQSFQG |

What is claimed is:

1. An antibody or antigen-binding fragment thereof that specifically binds to Nectin-4, comprising:

(1a)

the following three heavy chain CDRs:

CDR-H1 comprising the sequence as set forth in SEQ ID NO: 3,

CDR-H2 comprising the sequence as set forth in SEQ ID NO: 4,

CDR-H3 comprising the sequence as set forth in SEQ ID NO: 5; and the following three light chain CDRs:

CDR-L1 comprising the sequence as set forth in SEQ ID NO: 6,

CDR-L2 comprising the sequence as set forth in SEQ ID NO: 7,

CDR-L3 comprising the sequence as set forth in SEQ ID NO: 8; or (1b)

the following three heavy chain CDRs:

CDR-H1 comprising the sequence as set forth in SEQ ID NO: 9,

CDR-H2 comprising the sequence as set forth in SEQ ID NO: 10,

CDR-H3 comprising the sequence as set forth in SEQ ID NO: 5; and
the following three light chain CDRs:
CDR-L1 comprising the sequence as set forth in SEQ ID NO: 6,
CDR-L2 comprising the sequence as set forth in SEQ ID NO: 7,
CDR-L3 comprising the sequence as set forth in SEQ ID NO: 8; or
(1c)
the following three heavy chain CDRs:
CDR-H1 comprising the sequence as set forth in SEQ ID NO: 11,
CDR-H2 comprising the sequence as set forth in SEQ ID NO: 12 or 63,
CDR-H3 comprising the sequence as set forth in SEQ ID NO: 5; and
the following three light chain CDRs:
CDR-L1 comprising the sequence as set forth in SEQ ID NO: 6,
CDR-L2 comprising the sequence as set forth in SEQ ID NO: 7,
CDR-L3 comprising the sequence as set forth in SEQ ID NO: 8; or
(1d)
the following three heavy chain CDRs:
CDR-H1 comprising the sequence as set forth in SEQ ID NO: 13,
CDR-H2 comprising the sequence as set forth in SEQ ID NO: 14,
CDR-H3 comprising the sequence as set forth in SEQ ID NO: 15; and
the following three light chain CDRs:
CDR-L1 comprising the sequence as set forth in SEQ ID NO: 16,
CDR-L2 comprising the sequence as set forth in SEQ ID NO: 17,
CDR-L3 comprising the sequence as set forth in SEQ ID NO: 8; or
(2a)
the following three heavy chain CDRs:
CDR-H1 comprising the sequence as set forth in SEQ ID NO: 21 or 18,
CDR-H2 comprising the sequence as set forth in SEQ ID NO: 22,
CDR-H3 comprising the sequence as set forth in SEQ ID NO: 23; and
the following three light chain CDRs:
CDR-L1 comprising the sequence as set forth in SEQ ID NO: 24,
CDR-L2 comprising the sequence as set forth in SEQ ID NO: 25,
CDR-L3 comprising the sequence as set forth in SEQ ID NO: 26; or
(2b)
the following three heavy chain CDRs:
CDR-H1 comprising the sequence as set forth in SEQ ID NO: 27 or 36,
CDR-H2 comprising the sequence as set forth in SEQ ID NO: 28,
CDR-H3 comprising the sequence as set forth in SEQ ID NO: 23; and
the following three light chain CDRs:
CDR-L1 comprising the sequence as set forth in SEQ ID NO: 24,
CDR-L2 comprising the sequence as set forth in SEQ ID NO: 25,
CDR-L3 comprising the sequence as set forth in SEQ ID NO: 26; or
(2c)
the following three heavy chain CDRs:
CDR-H1 comprising the sequence as set forth in SEQ ID NO: 29 or 44,
CDR-H2 comprising the sequence as set forth in SEQ ID NO: 30,
CDR-H3 comprising the sequence as set forth in SEQ ID NO: 23; and
the following three light chain CDRs:
CDR-L1 comprising the sequence as set forth in SEQ ID NO: 24,
CDR-L2 comprising the sequence as set forth in SEQ ID NO: 25,
CDR-L3 comprising the sequence as set forth in SEQ ID NO: 26; or
(2d)
the following three heavy chain CDRs:
CDR-H1 comprising the sequence as set forth in SEQ ID NO: 31 or 54,
CDR-H2 comprising the sequence as set forth in SEQ ID NO: 32,
CDR-H3 comprising the sequence as set forth in SEQ ID NO: 33; and
the following three light chain CDRs:
CDR-L1 comprising the sequence as set forth in SEQ ID NO: 34,
CDR-L2 comprising the sequence as set forth in SEQ ID NO: 35,
CDR-L3 comprising the sequence as set forth in SEQ ID NO: 26; or
(3a)
the following three heavy chain CDRs:
CDR-H1 comprising the sequence as set forth in SEQ ID NO: 39,
CDR-H2 comprising the sequence as set forth in SEQ ID NO: 40,
CDR-H3 comprising the sequence as set forth in SEQ ID NO: 41; and
the following three light chain CDRs:
CDR-L1 comprising the sequence as set forth in SEQ ID NO: 42,
CDR-L2 comprising the sequence as set forth in SEQ ID NO: 43,
CDR-L3 comprising the sequence as set forth in SEQ ID NO: 8; or
(3b)
the following three heavy chain CDRs:
CDR-H1 comprising the sequence as set forth in SEQ ID NO: 45,
CDR-H2 comprising the sequence as set forth in SEQ ID NO: 46,
CDR-H3 comprising the sequence as set forth in SEQ ID NO: 41; and
the following three light chain CDRs:
CDR-L1 comprising the sequence as set forth in SEQ ID NO: 42,
CDR-L2 comprising the sequence as set forth in SEQ ID NO: 43,
CDR-L3 comprising the sequence as set forth in SEQ ID NO: 8; or
(3c)
the following three heavy chain CDRs:
CDR-H1 comprising the sequence as set forth in NO: 47,
CDR-H2 comprising the sequence as set forth in SEQ ID NO: 48 or 64, CDR-H3 comprising the sequence as set forth in SEQ ID NO: 41; and the following three light chain CDRs:

CDR-L1 comprising the sequence as set forth in SEQ ID NO: 42,

CDR-L2 comprising the sequence as set forth in SEQ ID NO: 43,

CDR-L3 comprising the sequence as set forth in SEQ ID NO: 8; or (3d)

the following three heavy chain CDRs:

CDR-H1 comprising the sequence as set forth in SEQ ID NO: 49,

CDR-H2 comprising the sequence as set forth in SEQ ID NO: 50,

CDR-H3 comprising the sequence as set forth in SEQ ID NO: 51; and the following three light chain CDRs:

CDR-L1 comprising the sequence as set forth in SEQ ID NO: 52,

CDR-L2 comprising the sequence as set forth in SEQ ID NO: 53,

CDR-L3 comprising the sequence as set forth in SEQ ID NO: 8.

2. The antibody or antigen-binding fragment thereof according to claim 1, comprising:

(a) the following six CDRs for heavy and light chains:

CDR-H1 comprising the sequence as set forth in SEQ ID NO: 3,

CDR-H2 comprising the sequence as set forth in SEQ ID NO: 4,

CDR-H3 comprising the sequence as set forth in SEQ ID NO: 5,

CDR-L1 comprising the sequence as set forth in SEQ ID NO: 6,

CDR-L2 comprising the sequence as set forth in SEQ ID NO: 7,

CDR-L3 comprising the sequence as set forth in SEQ ID NO: 8; or (b) the following six CDRs for heavy and light chains:

CDR-H1 comprising the sequence as set forth in SEQ ID NO: 9,

CDR-H2 comprising the sequence as set forth in SEQ ID NO: 10,

CDR-H3 comprising the sequence as set forth in SEQ ID NO: 5,

CDR-L1 comprising the sequence as set forth in SEQ ID NO: 6,

CDR-L2 comprising the sequence as set forth in SEQ ID NO: 7,

CDR-L3 comprising the sequence as set forth in SEQ ID NO: 8; or (c) the following six CDRs for heavy and light chains:

CDR-H1 comprising the sequence as set forth in SEQ ID NO: 11,

CDR-H2 comprising the sequence as set forth in SEQ ID NO: 12 or 63,

CDR-H3 comprising the sequence as set forth in SEQ ID NO: 5,

CDR-L1 comprising the sequence as set forth in SEQ ID NO: 6,

CDR-L2 comprising the sequence as set forth in SEQ ID NO: 7,

CDR-L3 comprising the sequence as set forth in SEQ ID NO: 8; or (d) the following six CDRs for heavy and light chains:

CDR-H1 comprising the sequence as set forth in SEQ ID NO: 13,

CDR-H2 comprising the sequence as set forth in SEQ ID NO: 14,

CDR-H3 comprising the sequence as set forth in SEQ ID NO: 15,

CDR-L1 comprising the sequence as set forth in SEQ ID NO: 16,

CDR-L2 comprising the sequence as set forth in SEQ ID NO: 17,

CDR-L3 comprising the sequence as set forth in SEQ ID NO: 8.

3. The antibody or antigen-binding fragment thereof according to claim 1, comprising:

(a) the following six CDRs for heavy and light chains:

CDR-H1 comprising the sequence as set forth in SEQ ID NO: 21 or 18,

CDR-H2 comprising the sequence as set forth in SEQ ID NO: 22,

CDR-H3 comprising the sequence as set forth in SEQ ID NO: 23,

CDR-L1 comprising the sequence as set forth in SEQ ID NO: 24,

CDR-L2 comprising the sequence as set forth in SEQ ID NO: 25,

CDR-L3 comprising the sequence as set forth in SEQ ID NO: 26; or (b) the following six CDRs for heavy and light chains:

CDR-H1 comprising the sequence as set forth in SEQ ID NO: 27 or 36,

CDR-H2 comprising the sequence as set forth in SEQ ID NO: 28,

CDR-H3 comprising the sequence as set forth in SEQ ID NO: 23,

CDR-L1 comprising the sequence as set forth in SEQ ID NO: 24,

CDR-L2 comprising the sequence as set forth in SEQ ID NO: 25,

CDR-L3 comprising the sequence as set forth in SEQ ID NO: 26; or (c) the following six CDRs for heavy and light chains:

CDR-H1 comprising the sequence as set forth in SEQ ID NO: 29 or 44,

CDR-H2 comprising the sequence as set forth in SEQ ID NO: 30,

CDR-H3 comprising the sequence as set forth in SEQ ID NO: 23,

CDR-L1 comprising the sequence as set forth in SEQ ID NO: 24,

CDR-L2 comprising the sequence as set forth in SEQ ID NO: 25,

CDR-L3 comprising the sequence as set forth in SEQ ID NO: 26; or (d) the following six CDRs for heavy and light chains:

CDR-H1 comprising the sequence as set forth in SEQ ID NO: 31 or 54,

CDR-H2 comprising the sequence as set forth in SEQ ID NO: 32,

CDR-H3 comprising the sequence as set forth in SEQ ID NO: 33,

CDR-L1 comprising the sequence as set forth in SEQ ID NO: 34,

CDR-L2 comprising the sequence as set forth in SEQ ID NO: 35,

CDR-L3 comprising the sequence as set forth in SEQ ID NO: 26.

4. The antibody or antigen-binding fragment thereof according to claim 1, comprising:
(a) the following six CDRs for heavy and light chains:
CDR-H1 comprising the sequence as set forth in SEQ ID NO: 39,
CDR-H2 comprising the sequence as set forth in SEQ ID NO: 40,
CDR-H3 comprising the sequence as set forth in SEQ ID NO: 41,
CDR-L1 comprising the sequence as set forth in SEQ ID NO: 42,
CDR-L2 comprising the sequence as set forth in SEQ ID NO: 43,
CDR-L3 comprising the sequence as set forth in SEQ ID NO: 8; or
(b) the following six CDRs for heavy and light chains:
CDR-H1 comprising the sequence as set forth in SEQ ID NO: 45,
CDR-H2 comprising the sequence as set forth in SEQ ID NO: 46,
CDR-H3 comprising the sequence as set forth in SEQ ID NO: 41,
CDR-L1 comprising the sequence as set forth in SEQ ID NO: 42,
CDR-L2 comprising the sequence as set forth in SEQ ID NO: 43,
CDR-L3 comprising the sequence as set forth in SEQ ID NO: 8; or
(c) the following six CDRs for heavy and light chains:
CDR-H1 comprising the sequence as set forth in SEQ ID NO: 47,
CDR-H2 comprising the sequence as set forth in SEQ ID NO: 48 or 64,
CDR-H3 comprising the sequence as set forth in SEQ ID NO: 41,
CDR-L1 comprising the sequence as set forth in SEQ ID NO: 42,
CDR-L2 comprising the sequence as set forth in SEQ ID NO: 43,
CDR-L3 comprising the sequence as set forth in SEQ ID NO: 8; or
(d) the following six CDRs for heavy and light chains:
CDR-H1 comprising the sequence as set forth in SEQ ID NO: 49,
CDR-H2 comprising the sequence as set forth in SEQ ID NO: 50,
CDR-H3 comprising the sequence as set forth in SEQ ID NO: 51,
CDR-L1 comprising the sequence as set forth in SEQ ID NO: 52,
CDR-L2 comprising the sequence as set forth in SEQ ID NO: 53,
CDR-L3 comprising the sequence as set forth in SEQ ID NO: 8.

5. The antibody or antigen-binding fragment thereof according to claim 1, comprising:
a VH having the sequence as set forth in SEQ ID NO: 1 or SEQ ID NO: 55 or a variant thereof and a VL having the sequence as set forth in SEQ ID NO: 2 or SEQ ID NO: 56 or a variant thereof; or
a VH having the sequence as set forth in SEQ ID NO: 19 or SEQ ID NO: 57 or a variant thereof and a VL having the sequence as set forth in SEQ ID NO: 20 or SEQ ID NO: 58 or a variant thereof; or
a VH having the sequence as set forth in SEQ ID NO: 37 or SEQ ID NO: 59 or a variant thereof and a VL having the sequence as set forth in SEQ ID NO: 38 or SEQ ID NO: 60 or a variant thereof;
wherein the variant has a sequence identity of at least 90% as compared to the sequence from which it is derived.

6. The antibody or antigen-binding fragment thereof according to claim 5, wherein the variant has a sequence identity of at least 99% as compared to the sequence from which it is derived.

7. The antibody or antigen-binding fragment thereof according to claim 1, further comprising:
a human immunoglobulin heavy chain constant region or a variant thereof, and a light chain constant region or a variant thereof, wherein the variant has a substitution, deletion or addition of one or more amino acids compared to the wild-type sequence from which it is derived;
wherein the heavy chain constant region has the sequence as set forth in SEQ ID NO: 61; the light chain constant region is a κ light chain constant region; and
the light chain constant region has the sequence as set forth in SEQ ID NO: 62.

8. The antibody or antigen-binding fragment thereof according to claim 1, comprising a heavy chain and a light chain, wherein:
(a) the heavy chain comprises: a VH having the sequence as set forth in SEQ ID NO: 1, and a heavy chain constant region having the sequence as set forth in SEQ ID NO: 61, and the light chain comprises: a VL having the sequence as set forth in SEQ ID NO: 2, and a light chain constant region having the sequence as set forth in SEQ ID NO: 62; or
(b) the heavy chain comprises: a VH having the sequence as set forth in SEQ ID NO: 19, and a heavy chain constant region having the sequence as set forth in SEQ ID NO: 61, and the light chain comprises: a VL having the sequence as set forth in SEQ ID NO: 20, and a light chain constant region having the sequence as set forth in SEQ ID NO: 62; or
(c) the heavy chain comprises: a VH having the sequence as set forth in SEQ ID NO: 37, and a heavy chain constant region having the sequence as set forth in SEQ ID NO: 61, and the light chain comprises: a VL having the sequence as set forth in SEQ ID NO: 38, and a light chain constant region having the sequence as set forth in SEQ ID NO: 62; or
(d) the heavy chain comprises: a VH having the sequence as set forth in SEQ ID NO: 55, and a heavy chain constant region having the sequence as set forth in SEQ ID NO: 61, and the light chain comprises: a VL having the sequence as set forth in SEQ ID NO: 56, and a light chain constant region having the sequence as set forth in SEQ ID NO: 62; or
(e) the heavy chain comprises: a VH having the sequence as set forth in SEQ ID NO: 57, and a heavy chain constant region having the sequence as set forth in SEQ ID NO: 61, and the light chain comprises: a VL having the sequence as set forth in SEQ ID NO: 58, and a light chain constant region having the sequence as set forth in SEQ ID NO: 62; or
(f) the heavy chain comprises: a VH having the sequence as set forth in SEQ ID NO: 59, and a heavy chain constant region having the sequence as set forth in SEQ ID NO: 61, and the light chain comprises: a VL having the sequence as set forth in SEQ ID NO: 60, and a light chain constant region having the sequence as set forth in SEQ ID NO:62.

9. An antibody-drug conjugate, comprising the antibody or antigen-binding fragment thereof according to claim 1 and at least one therapeutic agent.

10. The antibody-drug conjugate according to claim 9, which has the structure shown in Formula (I), $$A\text{-}(L\text{-}D)_{\gamma} \quad (I);$$

wherein, A represents the antibody or antigen-binding fragment thereof according to claim 1;

L is selected from Val, Cit, Phe, Lys, D-Val, Leu, Gly, Ala, Asn,

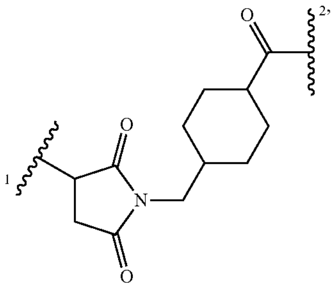

,

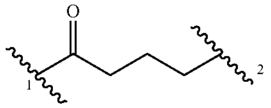

,

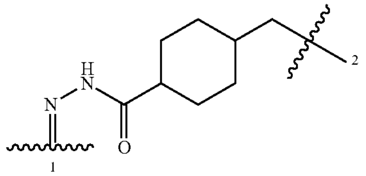

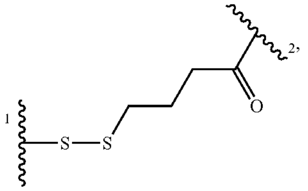

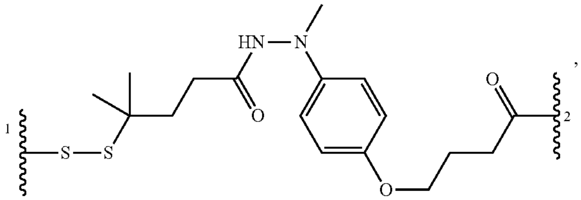

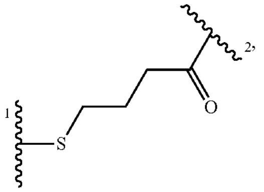

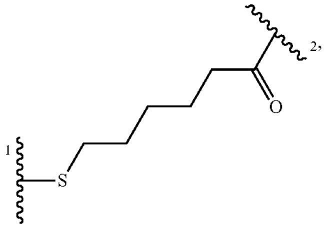

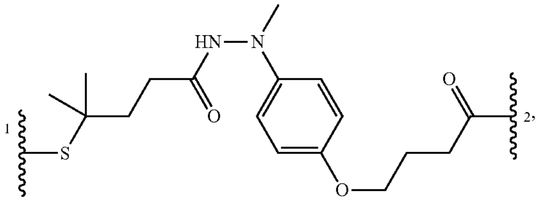

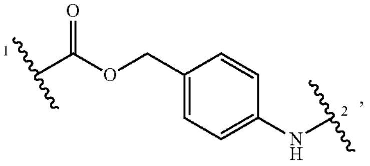

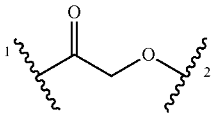

and

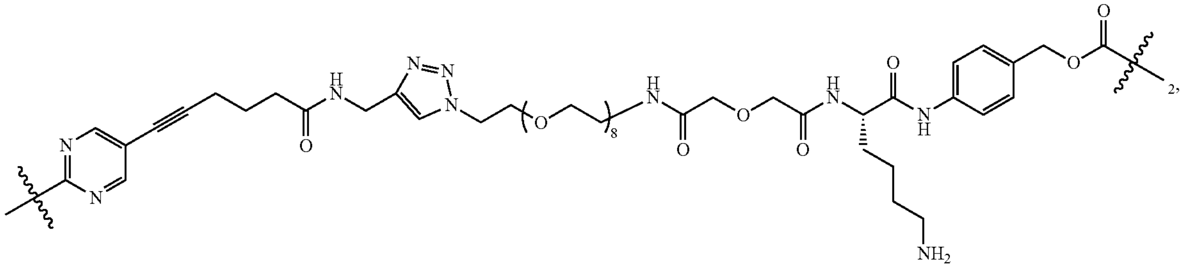

wherein, one of position 1 and position 2 represents the position where L and A are connected, and the other represents the position where L and D are connected;

D is selected from the group consisting of cytotoxic agents, therapeutic antibodies, radioisotopes, oligonucleotides and analogs thereof, biologically active peptides, protein toxins and enzymes; and γ is an integer of 1 to 10.

11. The antibody-drug conjugate according to claim 10, wherein the (L-D) moiety has the structure of Formula (1), which is connected by forming a thioether bond with a sulfhydryl group of A, Formula (1)

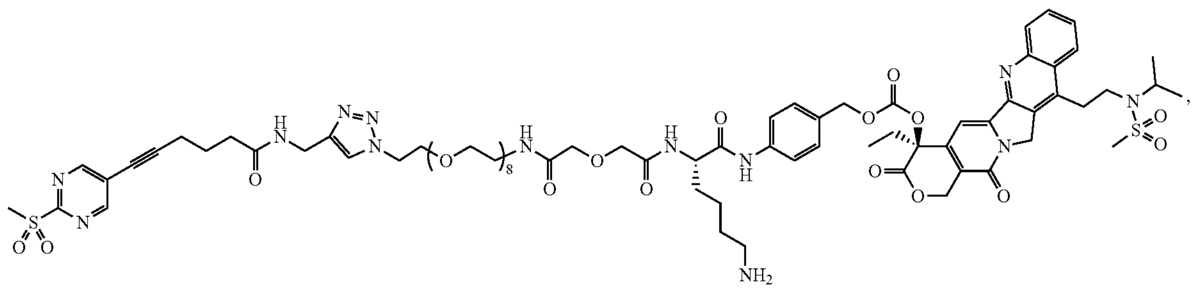

the antibody-drug conjugate has the structure of Formula (2):

Formula (2)

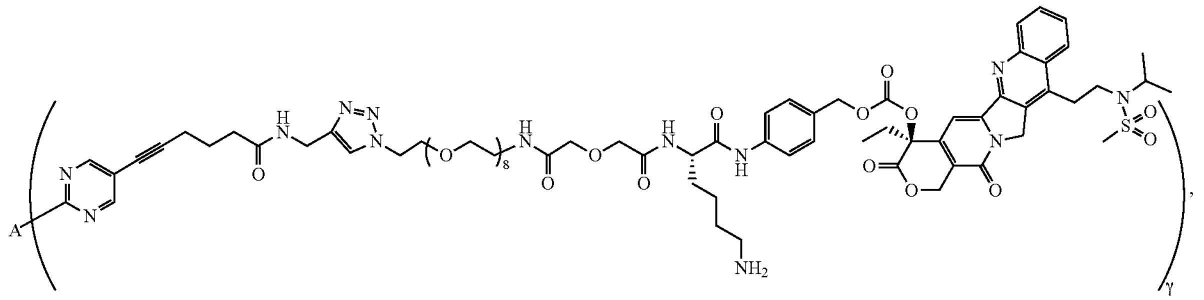

wherein γ is an integer from 1 to 10, and A represents the antibody or antigen-binding fragment thereof according to claim 1.

12. A composition, comprising the antibody-drug conjugate according to claim 9, wherein the molar ratio of therapeutic agent to the antibody or antigen-binding fragment thereof in the composition is a decimal or integer between 1 and 10.

13. A pharmaceutical composition, comprising the antibody-drug conjugate according to claim 9, and a pharmaceutically acceptable excipient.

14. A method of treating cancer, wherein the method comprises administering to a subject in need thereof an effective amount of the antibody or antigen binding fragment thereof of claim 1.

15. A method of treating cancer, wherein the method comprises administering to a subject in need thereof an effective amount of the antibody-drug conjugate of claim 9.

16. The method of claim 15, wherein the method further comprises administering a treatment regiment selected from the group consisting of: surgery, radiotherapy, chemotherapy, targeted therapy, immunotherapy, hormone therapy, angiogenesis inhibition, and palliative care.

17. The method of claim 15, wherein the method further comprises administering one or more therapeutic agents selected from the group consisting of: chemotherapeutic agents, radioisotopes, immune checkpoint inhibitors, antibody targeting other antigens, and other anti-tumor drugs.

18. The method of claim 15, wherein the method inhibits tumor cell survival and proliferation by preventing inhibition of anoikis and preventing activation of the PI3K-AKT signaling pathway.

19. A chimeric antigen receptor (CAR), comprising the antibody or antigen-binding fragment thereof according to claim 1, a transmembrane domain, and one or more intracellular T cell signaling domains.

20. An immune effector cell, expressing the CAR according to claim 19 on its surface.

21. A nucleic acid molecule, encoding the antibody or antigen-binding fragment thereof according to claim 1.

22. An expression vector, comprising the nucleic acid molecule according to claim 21.

23. A host cell, comprising the expression vector according to claim 22.

24. A multispecific antibody, comprising the antibody or antigen-binding fragment thereof according to claim 1 and at least one other antibody or antigen-binding fragment thereof or an antibody analog, so that the multispecific antibody is capable of binding to Nectin-4 and at least one other antigen.

25. A fusion protein, comprising the antibody or antigen-binding fragment thereof according to claim 1, and an additional biologically active polypeptide.

26. A pharmaceutical composition, comprising the antibody or antigen-binding fragment thereof according to claim 1, and a pharmaceutically acceptable excipient.

27. An antibody-drug conjugate, which is:

Formula (2)

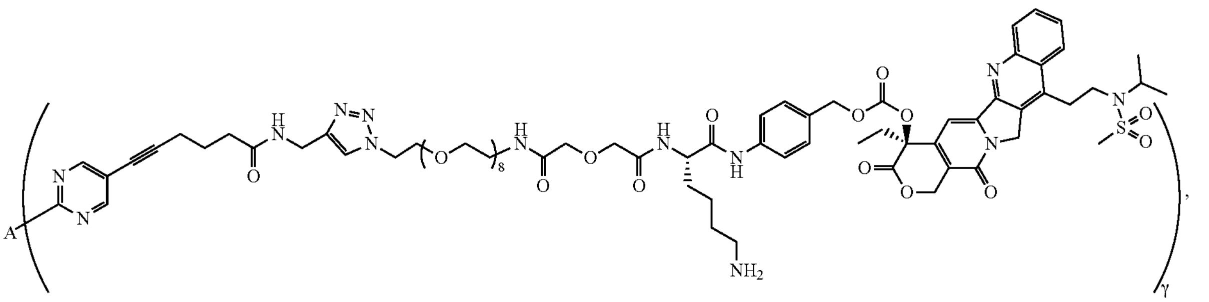

wherein A is an anti-human Nectin-4 humanized monoclonal antibody comprising the following six CDRs for heavy and light chains:

CDR-H1 comprising the sequence as set forth in SEQ ID NO: 18,

CDR-H2 comprising the sequence as set forth in SEQ ID NO: 22,

CDR-H3 comprising the sequence as set forth in SEQ ID NO: 23;

CDR-L1 comprising the sequence as set forth in SEQ ID NO: 24,

CDR-L2 comprising the sequence as set forth in SEQ ID NO: 25, and

CDR-L3 comprising the sequence as set forth in SEQ ID NO: 26;

wherein the anti-human Nectin-4 humanized monoclonal antibody is linked to the rest of the conjugate via one or more thiol group(s) of the antibody, and γ is an integer from 1 to 10.

28. The antibody-drug conjugate of claim 27, wherein the anti-human Nectin-4 humanized monoclonal antibody comprises a VH sequence as set forth in SEQ ID NO: 57, and a VL sequence as set forth in SEQ ID NO: 58.

29. The antibody-drug conjugate of claim 27, wherein γ is an integer from 6 to 8.

30. The antibody-drug conjugate of claim 27, wherein each light chain of the anti-human Nectin-4 humanized monoclonal antibody is conjugated to 0 to 1, and each heavy chain of the anti-human Nectin-4 humanized monoclonal antibody is conjugated to 0 to 4 of the following structure:

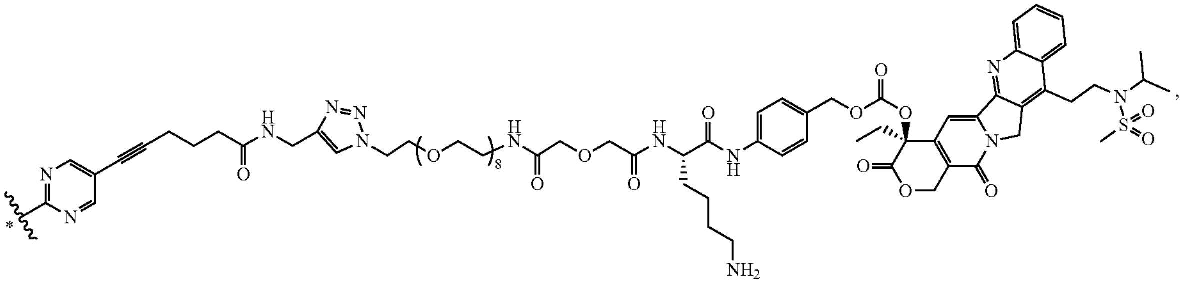

wherein * is the point of attachment to a thiol group of the anti-human Nectin-4 humanized monoclonal antibody.

31. A pharmaceutical composition, comprising the antibody-drug conjugate of claim 27, and one or more pharmaceutical excipients.

32. The pharmaceutical composition of claim 31, which has a drug-to-antibody ratio ("DAR") of from 7.0 to 8.0.

33. The pharmaceutical composition of claim 31, which has a DAR of 7.71.

34. A method of treating cancer, wherein the method comprises administering to a subject in need thereof an effective amount of the pharmaceutical composition of claim 31.

35. An antibody-drug conjugate, which is:

Formula (2)

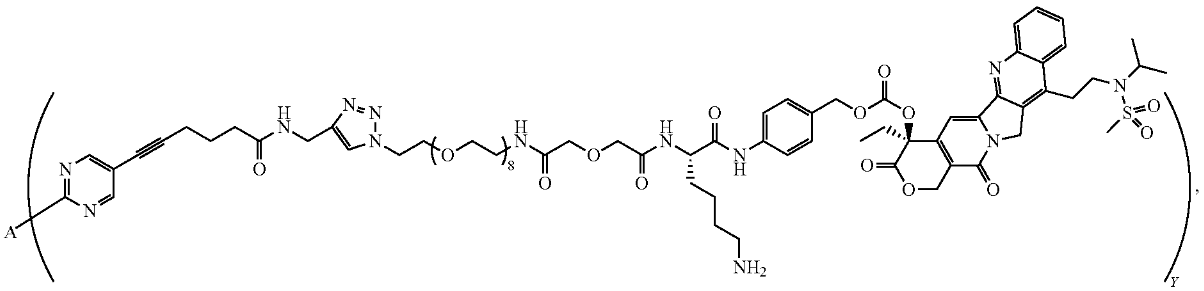

wherein A is an anti-human Nectin-4 humanized monoclonal antibody comprising a heavy chain and a light chain, wherein the heavy chain comprises: a VH having the sequence as set forth in SEQ ID NO: 57, and a heavy chain constant region having the sequence as set forth in SEQ ID NO: 61, and the light chain comprises: a VL having the sequence as set forth in SEQ ID NO: 58, and a light chain constant region having the sequence as set forth in SEQ ID NO: 62, and wherein the anti-human Nectin-4 humanized monoclonal antibody is linked to the rest of the conjugate via one or more thiol group(s) of the antibody, and y is an integer from 1 to 8.

* * * * *

SEQUENCE LISTING

<160> NUMBER OF SEQ ID NOS: 64

<210> SEQ ID NO 1
<211> LENGTH: 120
<212> TYPE: PRT
<213> ORGANISM: Artificial Sequence
<220> FEATURE:
<223> OTHER INFORMATION: 31#VH

<400> SEQUENCE: 1

```
Glu Val Gln Leu Gln Gln Pro Gly Ala Asp Leu Val Arg Pro Gly Ala
1               5                   10                  15

Ser Val Lys Leu Ser Cys Lys Ala Ser Gly Tyr Thr Phe Thr Asp Tyr
            20                  25                  30

Trp Met Asn Trp Val Lys Leu Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Trp Asp Phe Arg Ile Tyr Tyr Ala Met Asp Tyr Trp Gly Gln
            100                 105                 110

Gly Thr Ser Val Thr Val Ser Ser
        115                 120
```

<210> SEQ ID NO 2
<211> LENGTH: 113
<212> TYPE: PRT
<213> ORGANISM: Artificial Sequence
<220> FEATURE:
<223> OTHER INFORMATION: 31#VL

<400> SEQUENCE: 2

```
Asp Val Val Ile Thr Gln Ser Pro Ser Ser Leu Ala Met Ser Val Gly
1               5                   10                  15

Gln Lys Val Thr Met Ser Cys Lys Ser Ser Gln Ser Leu Leu Asn Thr
            20                  25                  30

Asn Ser Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Thr Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Ile
            100                 105                 110

Lys
```

<210> SEQ ID NO 3
<211> LENGTH: 7
<212> TYPE: PRT
<213> ORGANISM: Artificial Sequence
<220> FEATURE:
<223> OTHER INFORMATION: Chothia 31#/31HZ CDR-H1

<400> SEQUENCE: 3

-continued

Gly Tyr Thr Phe Thr Asp Tyr
1 5

<210> SEQ ID NO 4
<211> LENGTH: 6
<212> TYPE: PRT
<213> ORGANISM: Artificial Sequence
<220> FEATURE:
<223> OTHER INFORMATION: Chothia 31# /31HZ CDR-H2

<400> SEQUENCE: 4

His Pro Ser Asp Ser Glu
1 5

<210> SEQ ID NO 5
<211> LENGTH: 11
<212> TYPE: PRT
<213> ORGANISM: Artificial Sequence
<220> FEATURE:
<223> OTHER INFORMATION: Chothia/Abm/ Kabat 31# /31HZ CDR-H3

<400> SEQUENCE: 5

Trp Asp Phe Arg Ile Tyr Tyr Ala Met Asp Tyr
1 5 10

<210> SEQ ID NO 6
<211> LENGTH: 17
<212> TYPE: PRT
<213> ORGANISM: Artificial Sequence
<220> FEATURE:
<223> OTHER INFORMATION: Chothia/Abm/ Kabat 31# /31HZ CDR-L1

<400> SEQUENCE: 6

Lys Ser Ser Gln Ser Leu Leu Asn Thr Asn Ser Gln Lys Asn Tyr Leu
1 5 10 15

Ala

<210> SEQ ID NO 7
<211> LENGTH: 7
<212> TYPE: PRT
<213> ORGANISM: Artificial Sequence
<220> FEATURE:
<223> OTHER INFORMATION: Chothia/Abm/ Kabat 31# /31HZ CDR-L2

<400> SEQUENCE: 7

Phe Ala Ser Thr Arg Glu Ser
1 5

<210> SEQ ID NO 8
<211> LENGTH: 9
<212> TYPE: PRT
<213> ORGANISM: Artificial Sequence
<220> FEATURE:
<223> OTHER INFORMATION: Chothia/Abm/ Kabat/IMGT 31#/31HZ/74#/74HZ
CDR-L3

<400> SEQUENCE: 8

Gln Gln His Tyr Ser Thr Pro Leu Thr
1 5

<210> SEQ ID NO 9
<211> LENGTH: 10
<212> TYPE: PRT
<213> ORGANISM: Artificial Sequence
<220> FEATURE:
<223> OTHER INFORMATION: Abm 31#/31HZ CDR-H1

<400> SEQUENCE: 9

Gly Tyr Thr Phe Thr Asp Tyr Trp Met Asn
1 5 10

<210> SEQ ID NO 10
<211> LENGTH: 10
<212> TYPE: PRT
<213> ORGANISM: Artificial Sequence
<220> FEATURE:
<223> OTHER INFORMATION: Abm 31# /31HZ CDR-H2

<400> SEQUENCE: 10

Met Ile His Pro Ser Asp Ser Glu Thr Arg
1 5 10

<210> SEQ ID NO 11
<211> LENGTH: 5
<212> TYPE: PRT
<213> ORGANISM: Artificial Sequence
<220> FEATURE:
<223> OTHER INFORMATION: Kabat 31# /31HZ CDR-H1

<400> SEQUENCE: 11

Asp Tyr Trp Met Asn
1 5

<210> SEQ ID NO 12
<211> LENGTH: 17
<212> TYPE: PRT
<213> ORGANISM: Artificial Sequence
<220> FEATURE:
<223> OTHER INFORMATION: Kabat 31# CDR-H2

<400> SEQUENCE: 12

Met Ile His Pro Ser Asp Ser Glu Thr Arg Leu Asn Gln Lys Phe Lys
1 5 10 15

Asp

<210> SEQ ID NO 13
<211> LENGTH: 8
<212> TYPE: PRT
<213> ORGANISM: Artificial Sequence
<220> FEATURE:
<223> OTHER INFORMATION: IMGT 31# /31HZ CDR-H1

<400> SEQUENCE: 13

Gly Tyr Thr Phe Thr Asp Tyr Trp
1 5

<210> SEQ ID NO 14
<211> LENGTH: 8
<212> TYPE: PRT
<213> ORGANISM: Artificial Sequence
<220> FEATURE:
<223> OTHER INFORMATION: IMGT 31#/31HZ CDR-H2

<400> SEQUENCE: 14

Ile His Pro Ser Asp Ser Glu Thr
1 5

<210> SEQ ID NO 15
<211> LENGTH: 13
<212> TYPE: PRT
<213> ORGANISM: Artificial Sequence
<220> FEATURE:
<223> OTHER INFORMATION: IMGT 31# /31HZ CDR-H3

<400> SEQUENCE: 15

Ala Arg Trp Asp Phe Arg Ile Tyr Tyr Ala Met Asp Tyr
1 5 10

<210> SEQ ID NO 16
<211> LENGTH: 12
<212> TYPE: PRT
<213> ORGANISM: Artificial Sequence
<220> FEATURE:
<223> OTHER INFORMATION: IMGT 31# /31HZ CDR-L1

<400> SEQUENCE: 16

Gln Ser Leu Leu Asn Thr Asn Ser Gln Lys Asn Tyr
1 5 10

<210> SEQ ID NO 17
<211> LENGTH: 3
<212> TYPE: PRT
<213> ORGANISM: Artificial Sequence
<220> FEATURE:
<223> OTHER INFORMATION: IMGT 31# /31HZ CDR-L2

<400> SEQUENCE: 17

Phe Ala Ser
1

<210> SEQ ID NO 18
<211> LENGTH: 10
<212> TYPE: PRT
<213> ORGANISM: Artificial Sequence
<220> FEATURE:
<223> OTHER INFORMATION: Chothia 56HZ CDR-H1

<400> SEQUENCE: 18

Gly Tyr Phe Asn Ser Ile Thr Ser Asp Tyr
1 5 10

<210> SEQ ID NO 19
<211> LENGTH: 117
<212> TYPE: PRT
<213> ORGANISM: Artificial Sequence
<220> FEATURE:
<223> OTHER INFORMATION: 56#VH

<400> SEQUENCE: 19

Gln Val Gln Leu Lys Glu Ser Gly Pro Gly Leu Val Lys Pro Ser Gln
1 5 10 15

Ser Leu Ser Leu Thr Cys Thr Val Thr Gly Tyr Ser Ile Thr Ser Asp
20 25 30

Tyr Asp Trp His Trp Ile Arg His Phe Pro Gly Asn Met Leu Glu Trp
35 40 45

Met Gly Tyr Ile Ser Phe Ser Gly Arg Thr Tyr Tyr Asn Pro Ser Leu
50 55 60

Lys Ser Arg Ile Ser Ile Thr His Asp Thr Ser Lys Asn His Phe Phe
65 70 75 80

Leu Arg Leu Asn Ser Val Thr Thr Glu Asp Thr Ala Thr Tyr Tyr Cys
85 90 95

Ala Arg Gly Asn Tyr Asp Gly Phe Asp Tyr Trp Gly Gln Gly Thr Thr
100 105 110

Leu Thr Val Ser Ser
115

<210> SEQ ID NO 20
<211> LENGTH: 108
<212> TYPE: PRT
<213> ORGANISM: Artificial Sequence
<220> FEATURE:
<223> OTHER INFORMATION: 56#VL

<400> SEQUENCE: 20

```
Asp Ile Gln Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile His Trp Tyr Gln His Arg Thr Asn Gly Ser Pro Arg Leu Leu Ile
        35                  40                  45

Lys Phe Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Lys Ser Trp Pro Thr
                85                  90                  95

Tyr Thr Phe Gly Gly Gly Thr Lys Leu Glu Ile Lys
            100                 105
```

<210> SEQ ID NO 21
<211> LENGTH: 8
<212> TYPE: PRT
<213> ORGANISM: Artificial Sequence
<220> FEATURE:
<223> OTHER INFORMATION: Chothia 56# CDR-H1

<400> SEQUENCE: 21

```
Gly Tyr Ser Ile Thr Ser Asp Tyr
1               5
```

<210> SEQ ID NO 22
<211> LENGTH: 5
<212> TYPE: PRT
<213> ORGANISM: Artificial Sequence
<220> FEATURE:
<223> OTHER INFORMATION: Chothia 56#/56HZ CDR-H2

<400> SEQUENCE: 22

```
Ser Phe Ser Gly Arg
1               5
```

<210> SEQ ID NO 23
<211> LENGTH: 8
<212> TYPE: PRT
<213> ORGANISM: Artificial Sequence
<220> FEATURE:
<223> OTHER INFORMATION: Chothia/Abm/ Kabat 56# /56HZ CDR-H3

<400> SEQUENCE: 23

```
Gly Asn Tyr Asp Gly Phe Asp Tyr
1               5
```

<210> SEQ ID NO 24
<211> LENGTH: 11
<212> TYPE: PRT
<213> ORGANISM: Artificial Sequence
<220> FEATURE:
<223> OTHER INFORMATION: Chothia/Abm/ Kabat 56# /56HZ CDR-L1

<400> SEQUENCE: 24

Arg Ala Ser Gln Asn Ile Gly Thr Ser Ile His
1 5 10

<210> SEQ ID NO 25
<211> LENGTH: 7
<212> TYPE: PRT
<213> ORGANISM: Artificial Sequence
<220> FEATURE:
<223> OTHER INFORMATION: Chothia/Abm/ Kabat 56# /56HZ CDR-L2

<400> SEQUENCE: 25

Phe Ala Ser Glu Ser Ile Ser
1 5

<210> SEQ ID NO 26
<211> LENGTH: 10
<212> TYPE: PRT
<213> ORGANISM: Artificial Sequence
<220> FEATURE:
<223> OTHER INFORMATION: Chothia/Abm/ Kabat/IMGT 56#/56HZ CDR-L3

<400> SEQUENCE: 26

Gln Gln Ser Lys Ser Trp Pro Thr Tyr Thr
1 5 10

<210> SEQ ID NO 27
<211> LENGTH: 11
<212> TYPE: PRT
<213> ORGANISM: Artificial Sequence
<220> FEATURE:
<223> OTHER INFORMATION: Abm 56# CDR-H1

<400> SEQUENCE: 27

Gly Tyr Ser Ile Thr Ser Asp Tyr Asp Trp His
1 5 10

<210> SEQ ID NO 28
<211> LENGTH: 9
<212> TYPE: PRT
<213> ORGANISM: Artificial Sequence
<220> FEATURE:
<223> OTHER INFORMATION: Abm 56# /56HZ CDR-H2

<400> SEQUENCE: 28

Tyr Ile Ser Phe Ser Gly Arg Thr Tyr
1 5

<210> SEQ ID NO 29
<211> LENGTH: 6
<212> TYPE: PRT
<213> ORGANISM: Artificial Sequence
<220> FEATURE:
<223> OTHER INFORMATION: Kabat 56# CDR-H1

<400> SEQUENCE: 29

Ser Asp Tyr Asp Trp His
1 5

<210> SEQ ID NO 30
<211> LENGTH: 16
<212> TYPE: PRT
<213> ORGANISM: Artificial Sequence
<220> FEATURE:
<223> OTHER INFORMATION: Kabat 56#/56HZ CDR-H2

<400> SEQUENCE: 30

```
Tyr Ile Ser Phe Ser Gly Arg Thr Tyr Tyr Asn Pro Ser Leu Lys Ser
1               5                   10                  15


<210> SEQ ID NO 31
<211> LENGTH: 9
<212> TYPE: PRT
<213> ORGANISM: Artificial Sequence
<220> FEATURE:
<223> OTHER INFORMATION: IMGT  56# CDR-H1

<400> SEQUENCE: 31

Gly Tyr Ser Ile Thr Ser Asp Tyr Asp
1               5


<210> SEQ ID NO 32
<211> LENGTH: 7
<212> TYPE: PRT
<213> ORGANISM: Artificial Sequence
<220> FEATURE:
<223> OTHER INFORMATION: IMGT  56#/56HZ   CDR-H2

<400> SEQUENCE: 32

Ile Ser Phe Ser Gly Arg Thr
1               5


<210> SEQ ID NO 33
<211> LENGTH: 10
<212> TYPE: PRT
<213> ORGANISM: Artificial Sequence
<220> FEATURE:
<223> OTHER INFORMATION: IMGT  56# /56HZ   CDR-H3

<400> SEQUENCE: 33

Ala Arg Gly Asn Tyr Asp Gly Phe Asp Tyr
1               5                   10


<210> SEQ ID NO 34
<211> LENGTH: 6
<212> TYPE: PRT
<213> ORGANISM: Artificial Sequence
<220> FEATURE:
<223> OTHER INFORMATION: IMGT  56# /56HZ  CDR-L1

<400> SEQUENCE: 34

Gln Asn Ile Gly Thr Ser
1               5


<210> SEQ ID NO 35
<211> LENGTH: 3
<212> TYPE: PRT
<213> ORGANISM: Artificial Sequence
<220> FEATURE:
<223> OTHER INFORMATION: IMGT  56#/56HZ   CDR-L2

<400> SEQUENCE: 35

Phe Ala Ser
1


<210> SEQ ID NO 36
<211> LENGTH: 13
<212> TYPE: PRT
<213> ORGANISM: Artificial Sequence
<220> FEATURE:
<223> OTHER INFORMATION: Abm  56HZ  CDR-H1

<400> SEQUENCE: 36

Gly Tyr Phe Asn Ser Ile Thr Ser Asp Tyr Asp Trp His
```

-continued 1 5 10

<210> SEQ ID NO 37
<211> LENGTH: 124
<212> TYPE: PRT
<213> ORGANISM: Artificial Sequence
<220> FEATURE:
<223> OTHER INFORMATION: 74#VH

<400> SEQUENCE: 37

Glu Val Gln Leu Gln Gln Pro Gly Ala Glu Leu Val Arg Pro Gly Ala
1 5 10 15

Ser Val Lys Leu Ser Cys Lys Ala Ser Gly Tyr Thr Phe Ile Asn Tyr
20 25 30

Trp Met Asn Trp Val Lys Gln Arg Pro Gly Gln Gly Leu Glu Trp Ile
35 40 45

Gly Met Ile His Pro Ser Asp Ser Ala Thr Arg Leu Asn Gln Lys Phe
50 55 60

Lys Asp Lys Ala Thr Leu Thr Val Asp Lys Ser Ser Ser Thr Ala Tyr
65 70 75 80

Met Gln Leu Ser Ser Pro Thr Ser Glu Asp Ser Ala Val Tyr Tyr Cys
85 90 95

Ala Arg Trp Gly Asn Phe Tyr Thr Val Asn Ala Trp Tyr Tyr Phe Asp
100 105 110

Tyr Trp Gly His Gly Thr Thr Leu Thr Val Ser Ser
115 120

<210> SEQ ID NO 38
<211> LENGTH: 113
<212> TYPE: PRT
<213> ORGANISM: Artificial Sequence
<220> FEATURE:
<223> OTHER INFORMATION: 74#VL

<400> SEQUENCE: 38

Asp Ile Val Ile Thr Gln Ser Pro Ser Ser Leu Ala Met Ser Val Gly
1 5 10 15

Gln Lys Val Thr Met Ser Cys Lys Ser Ser Gln Thr Leu Leu Asn Ser
20 25 30

Asn Thr Gln Lys Asn Tyr Leu Ala Trp Tyr Gln Gln Lys Pro Gly Gln
35 40 45

Ser Pro Lys Leu Leu Phe Tyr Phe Ala Ser Thr Arg Glu Ser Gly Val
50 55 60

Pro Asp Arg Phe Ile Gly Ser Gly Ser Gly Thr Asn Phe Thr Leu Thr
65 70 75 80

Ile Ser Ser Val Gln Ala Glu Asp Leu Ala Asp Tyr Phe Cys Gln Gln
85 90 95

His Tyr Ser Thr Pro Leu Thr Phe Gly Ala Gly Thr Lys Leu Glu Ile
100 105 110

Lys

<210> SEQ ID NO 39
<211> LENGTH: 7
<212> TYPE: PRT
<213> ORGANISM: Artificial Sequence
<220> FEATURE:
<223> OTHER INFORMATION: Chothia 74#/74HZ CDR-H1

<400> SEQUENCE: 39

Gly Tyr Thr Phe Ile Asn Tyr
1 5

<210> SEQ ID NO 40
<211> LENGTH: 6
<212> TYPE: PRT
<213> ORGANISM: Artificial Sequence
<220> FEATURE:
<223> OTHER INFORMATION: Chothia 74#/74HZ CDR-H2

<400> SEQUENCE: 40

His Pro Ser Asp Ser Ala
1 5

<210> SEQ ID NO 41
<211> LENGTH: 15
<212> TYPE: PRT
<213> ORGANISM: Artificial Sequence
<220> FEATURE:
<223> OTHER INFORMATION: Chothia/Abm/ Kabat 74#/74HZ CDR-H3

<400> SEQUENCE: 41

Trp Gly Asn Phe Tyr Thr Val Asn Ala Trp Tyr Tyr Phe Asp Tyr
1 5 10 15

<210> SEQ ID NO 42
<211> LENGTH: 17
<212> TYPE: PRT
<213> ORGANISM: Artificial Sequence
<220> FEATURE:
<223> OTHER INFORMATION: Chothia/Abm/ Kabat 74#/74HZ CDR-L1

<400> SEQUENCE: 42

Lys Ser Ser Gln Thr Leu Leu Asn Ser Asn Thr Gln Lys Asn Tyr Leu
1 5 10 15

Ala

<210> SEQ ID NO 43
<211> LENGTH: 7
<212> TYPE: PRT
<213> ORGANISM: Artificial Sequence
<220> FEATURE:
<223> OTHER INFORMATION: Chothia/Abm/ Kabat 74#/74HZ CDR-L2

<400> SEQUENCE: 43

Phe Ala Ser Thr Arg Glu Ser
1 5

<210> SEQ ID NO 44
<211> LENGTH: 8
<212> TYPE: PRT
<213> ORGANISM: Artificial Sequence
<220> FEATURE:
<223> OTHER INFORMATION: Kabat 56HZ CDR-H1

<400> SEQUENCE: 44

Ile Thr Ser Asp Tyr Asp Trp His
1 5

<210> SEQ ID NO 45
<211> LENGTH: 10
<212> TYPE: PRT
<213> ORGANISM: Artificial Sequence
<220> FEATURE:
<223> OTHER INFORMATION: Abm 74#/74HZ CDR-H1

<400> SEQUENCE: 45

```
Gly Tyr Thr Phe Ile Asn Tyr Trp Met Asn
1               5                   10


<210> SEQ ID NO 46
<211> LENGTH: 10
<212> TYPE: PRT
<213> ORGANISM: Artificial Sequence
<220> FEATURE:
<223> OTHER INFORMATION: Abm  74#/74HZ  CDR-H2

<400> SEQUENCE: 46

Met Ile His Pro Ser Asp Ser Ala Thr Arg
1               5                   10


<210> SEQ ID NO 47
<211> LENGTH: 5
<212> TYPE: PRT
<213> ORGANISM: Artificial Sequence
<220> FEATURE:
<223> OTHER INFORMATION: Kabat  74#  /74HZ CDR-H1

<400> SEQUENCE: 47

Asn Tyr Trp Met Asn
1               5


<210> SEQ ID NO 48
<211> LENGTH: 17
<212> TYPE: PRT
<213> ORGANISM: Artificial Sequence
<220> FEATURE:
<223> OTHER INFORMATION: Kabat  74# CDR-H2

<400> SEQUENCE: 48

Met Ile His Pro Ser Asp Ser Ala Thr Arg Leu Asn Gln Lys Phe Lys
1               5                   10                  15

Asp


<210> SEQ ID NO 49
<211> LENGTH: 8
<212> TYPE: PRT
<213> ORGANISM: Artificial Sequence
<220> FEATURE:
<223> OTHER INFORMATION: IMGT  74#/74HZ  CDR-H1

<400> SEQUENCE: 49

Gly Tyr Thr Phe Ile Asn Tyr Trp
1               5


<210> SEQ ID NO 50
<211> LENGTH: 8
<212> TYPE: PRT
<213> ORGANISM: Artificial Sequence
<220> FEATURE:
<223> OTHER INFORMATION: IMGT  74#/74HZ CDR-H2

<400> SEQUENCE: 50

Ile His Pro Ser Asp Ser Ala Thr
1               5


<210> SEQ ID NO 51
<211> LENGTH: 17
<212> TYPE: PRT
<213> ORGANISM: Artificial Sequence
<220> FEATURE:
<223> OTHER INFORMATION: IMGT  74#/74HZ CDR-H3
```

<400> SEQUENCE: 51

Ala Arg Trp Gly Asn Phe Tyr Thr Val Asn Ala Trp Tyr Tyr Phe Asp
1 5 10 15

Tyr

<210> SEQ ID NO 52
<211> LENGTH: 12
<212> TYPE: PRT
<213> ORGANISM: Artificial Sequence
<220> FEATURE:
<223> OTHER INFORMATION: IMGT 74#/74HZ CDR-L1

<400> SEQUENCE: 52

Gln Thr Leu Leu Asn Ser Asn Thr Gln Lys Asn Tyr
1 5 10

<210> SEQ ID NO 53
<211> LENGTH: 3
<212> TYPE: PRT
<213> ORGANISM: Artificial Sequence
<220> FEATURE:
<223> OTHER INFORMATION: IMGT 74#/74HZ CDR-L2

<400> SEQUENCE: 53

Phe Ala Ser
1

<210> SEQ ID NO 54
<211> LENGTH: 11
<212> TYPE: PRT
<213> ORGANISM: Artificial Sequence
<220> FEATURE:
<223> OTHER INFORMATION: IMGT 56HZ CDR-H1

<400> SEQUENCE: 54

Gly Tyr Phe Asn Ser Ile Thr Ser Asp Tyr Asp
1 5 10

<210> SEQ ID NO 55
<211> LENGTH: 120
<212> TYPE: PRT
<213> ORGANISM: Artificial Sequence
<220> FEATURE:
<223> OTHER INFORMATION: 31HZ VH

<400> SEQUENCE: 55

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Trp Met Asn Trp Val Arg Leu Ala Pro Gly Gln Gly Leu Glu Trp Ile
35 40 45

Gly Met Ile His Pro Ser Asp Ser Glu Thr Arg Leu Asn Gln Lys Phe
50 55 60

Gln Gly Arg Val Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Asp Phe Arg Ile Tyr Tyr Ala Met Asp Tyr Trp Gly Gln
100 105 110

Gly Thr Leu Val Thr Val Ser Ser
115 120

<210> SEQ ID NO 56
<211> LENGTH: 113
<212> TYPE: PRT
<213> ORGANISM: Artificial Sequence
<220> FEATURE:
<223> OTHER INFORMATION: 31HZ VL

<400> SEQUENCE: 56

```
Asp Val Val Ile Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Thr
            20                  25                  30

Asn Ser Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Thr Pro Leu Thr Phe Gly Gly Gly Thr Lys Val Glu Ile
            100                 105                 110

Lys
```

<210> SEQ ID NO 57
<211> LENGTH: 119
<212> TYPE: PRT
<213> ORGANISM: Artificial Sequence
<220> FEATURE:
<223> OTHER INFORMATION: 56HZ VH

<400> SEQUENCE: 57

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Phe Asn Ser Ile Thr
            20                  25                  30

Ser Asp Tyr Asp Trp His Trp Ile Arg His His Pro Gly Lys Gly Leu
        35                  40                  45

Glu Trp Met Gly Tyr Ile Ser Phe Ser Gly Arg Thr Tyr Tyr Asn Pro
    50                  55                  60

Ser Leu Lys Ser Arg Val Thr Ile Ser His Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Asn Tyr Asp Gly Phe Asp Tyr Trp Gly Gln Gly
            100                 105                 110

Thr Leu Val Thr Val Ser Ser
        115
```

<210> SEQ ID NO 58
<211> LENGTH: 108
<212> TYPE: PRT
<213> ORGANISM: Artificial Sequence
<220> FEATURE:
<223> OTHER INFORMATION: 56HZ VL

<400> SEQUENCE: 58

```
Asp Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Gln Asn Ile Gly Thr Ser
            20                  25                  30

Ile His Trp Tyr Gln His Lys Pro Gly Gln Ser Pro Arg Leu Leu Ile
        35                  40                  45

Lys Phe Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Lys Ser Trp Pro Thr
                85                  90                  95

Tyr Thr Phe Gly Gly Gly Thr Lys Val Glu Ile Lys
            100                 105


<210> SEQ ID NO 59
<211> LENGTH: 124
<212> TYPE: PRT
<213> ORGANISM: Artificial Sequence
<220> FEATURE:
<223> OTHER INFORMATION: 74HZ  VH

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ile Asn Tyr
            20                  25                  30

Trp Met Asn Trp Val Arg Gln Ala Pro Gly Gln Gly Leu Glu Trp Ile
        35                  40                  45

Gly Met Ile His Pro Ser Asp Ser Ala Thr Arg Leu Asn Gln Ser Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Asn Phe Tyr Thr Val Asn Ala Trp Tyr Tyr Phe Asp
            100                 105                 110

Tyr Trp Gly Gln Gly Thr Leu Val Thr Val Ser Ser
        115                 120


<210> SEQ ID NO 60
<211> LENGTH: 113
<212> TYPE: PRT
<213> ORGANISM: Artificial Sequence
<220> FEATURE:
<223> OTHER INFORMATION: 74HZ  VL

<400> SEQUENCE: 60

Asp Ile Val Ile Thr Gln Ser Pro Asp Ser Leu Ala Val Ser Leu Gly
1               5                   10                  15

Glu Arg Ala Thr Ile Asn Cys Lys Ser Ser Gln Thr Leu Leu Asn Ser
            20                  25                  30

Asn Thr Gln Lys Asn Tyr Leu Ala Trp Tyr Gln Gln Lys Pro Gly Gln
        35                  40                  45

Ser Pro Lys Leu Leu Phe Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Phe Cys Gln Gln
                85                  90                  95

His Tyr Ser Thr Pro Leu Thr Phe Gly Gln Gly Thr Lys Leu Glu Ile
            100                 105                 110

Lys


<210> SEQ ID NO 61
<211> LENGTH: 330
<212> TYPE: PRT
<213> ORGANISM: Artificial Sequence
<220> FEATURE:
<223> OTHER INFORMATION: IgG1 heavy chain constant region

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

-continued

```
                325                 330


<210> SEQ ID NO 62
<211> LENGTH: 107
<212> TYPE: PRT
<213> ORGANISM: Artificial Sequence
<220> FEATURE:
<223> OTHER INFORMATION: Kappa light chain constant region

<400> SEQUENCE: 62

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 63
<211> LENGTH: 17
<212> TYPE: PRT
<213> ORGANISM: Artificial Sequence
<220> FEATURE:
<223> OTHER INFORMATION: Kabat  31HZ CDR-H2

<400> SEQUENCE: 63

Met Ile His Pro Ser Asp Ser Glu Thr Arg Leu Asn Gln Lys Phe Gln
1               5                   10                  15

Gly


<210> SEQ ID NO 64
<211> LENGTH: 17
<212> TYPE: PRT
<213> ORGANISM: Artificial Sequence
<220> FEATURE:
<223> OTHER INFORMATION: Kabat 74HZ CDR-H2

<400> SEQUENCE: 64

Met Ile His Pro Ser Asp Ser Ala Thr Arg Leu Asn Gln Ser Phe Gln
1               5                   10                  15

Gly
```